United States Patent
Johnson et al.

(10) Patent No.: US 9,393,034 B2
(45) Date of Patent: Jul. 19, 2016

(54) SPIRAL SHAPED FILTER

(71) Applicant: Crux Biomedical, Inc., San Diego, CA (US)

(72) Inventors: Eric Johnson, Woodside, CA (US); Thomas J. Fogarty, Portola Valley, CA (US); Frank Arko, Plano, TX (US); Jeff Elkins, Woodside, CA (US); Martin Seery, San Rafael, CA (US)

(73) Assignee: CRUX BIOMEDICAL, INC., San Diego, CA (US)

( * ) Notice: Subject to any disclaimer, the term of this patent is extended or adjusted under 35 U.S.C. 154(b) by 494 days.

(21) Appl. No.: 13/791,610

(22) Filed: Mar. 8, 2013

(65) Prior Publication Data

US 2013/0184744 A1    Jul. 18, 2013

Related U.S. Application Data

(63) Continuation of application No. 12/862,694, filed on Aug. 24, 2010, now Pat. No. 9,028,524, which is a continuation of application No. 11/325,249, filed on Jan. 3, 2006, now abandoned.

(Continued)

(51) Int. Cl.
*A61B 17/221* (2006.01)
*A61F 2/01* (2006.01)
*A61M 25/00* (2006.01)

(52) U.S. Cl.
CPC ............ *A61B 17/221* (2013.01); *A61F 2/01* (2013.01); *A61F 2002/011* (2013.01); *A61F 2002/016* (2013.01); *A61F 2002/018* (2013.01);

(Continued)

(58) Field of Classification Search
CPC .... A61B 17/221; A61F 2/01; A61F 2002/011; A61F 2002/016; A61F 2002/018; A61F 2230/001; A61F 2/013; A61F 2002/013; A61M 25/0021; A61M 25/007; A61M 2025/0037; A61M 2025/004
USPC ................ 606/200, 113, 114, 110, 198, 159; 604/104–106, 22
See application file for complete search history.

(56) References Cited

U.S. PATENT DOCUMENTS

| 152,652 A | 6/1874 | Knowlton |
|---|---|---|
| 407,971 A | 7/1889 | Siersdorfer |

(Continued)

FOREIGN PATENT DOCUMENTS

| CN | 2635045 Y | 8/2004 |
|---|---|---|
| GB | 1588072 | 4/1981 |

(Continued)

OTHER PUBLICATIONS

Millward, Steven F.; Temporary and retrievable inferior vena cava filters; JVIR; vol. 9; No. 3; pp. 381-387, May/Jun. 1998.

(Continued)

*Primary Examiner* — Katrina Stransky
(74) *Attorney, Agent, or Firm* — Thomas C. Meyers; Brown Rudnick LLP

(57) ABSTRACT

In one embodiment, a filter includes a first spiral support member having a first end and a second end; a second spiral support member positioned adjacent the first spiral support member to form a loop between the first end and the second end; a material covering a portion of the first and the second spiral support members; and a structure attached to the loop.

10 Claims, 50 Drawing Sheets

Related U.S. Application Data

(60) Provisional application No. 60/641,327, filed on Jan. 3, 2005, provisional application No. 60/668,548, filed on Apr. 4, 2005, provisional application No. 60/673,980, filed on Apr. 21, 2005.

(52) U.S. Cl.
CPC ... *A61F2230/001* (2013.01); *A61F 2230/0008* (2013.01); *A61F 2230/0067* (2013.01); *A61F 2230/0095* (2013.01); *A61F 2250/0067* (2013.01); *A61M 25/007* (2013.01); *A61M 25/0021* (2013.01); *A61M 2025/004* (2013.01); *A61M 2025/0037* (2013.01)

(56) References Cited

U.S. PATENT DOCUMENTS

| | | |
|---|---|---|
| 621,937 A | 3/1899 | Niemann |
| 796,910 A | 8/1905 | Hernan |
| 1,950,378 A | 3/1934 | Andrews |
| 2,163,324 A | 6/1939 | Reinhold |
| 4,425,908 A | 1/1984 | Simon |
| 4,619,246 A | 10/1986 | Molgaard-Nielsen et al. |
| 5,098,440 A | 3/1992 | Hillstead |
| 5,234,458 A | 8/1993 | Metais |
| 5,370,657 A | 12/1994 | Irie |
| 5,375,612 A | 12/1994 | Cottenceau et al. |
| 5,601,595 A | 2/1997 | Smith |
| 5,626,605 A | 5/1997 | Irie et al. |
| 5,725,552 A | 3/1998 | Kotula et al. |
| 5,814,064 A | 9/1998 | Daniel et al. |
| RE36,057 E | 1/1999 | Martin |
| 5,925,060 A | 7/1999 | Forber |
| 5,944,738 A | 8/1999 | Amplatz et al. |
| 6,053,925 A | 4/2000 | Barnhart |
| 6,080,182 A | 6/2000 | Shaw et al. |
| 6,099,534 A | 8/2000 | Bates et al. |
| 6,106,476 A | 8/2000 | Corl et al. |
| 6,171,327 B1 | 1/2001 | Daniel et al. |
| 6,231,581 B1 | 5/2001 | Shank et al. |
| 6,346,116 B1 | 2/2002 | Brooks et al. |
| 6,368,338 B1 | 4/2002 | Konya et al. |
| 6,443,972 B1 | 9/2002 | Bosma et al. |
| 6,458,145 B1 | 10/2002 | Ravenscroft et al. |
| 6,468,301 B1 | 10/2002 | Amplatz et al. |
| 6,485,502 B2 | 11/2002 | Don Michael et al. |
| 6,514,273 B1 | 2/2003 | Voss et al. |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,554,849 B1 | 4/2003 | Jones et al. |
| 6,610,077 B1 | 8/2003 | Hancock et al. |
| 6,613,074 B1 | 9/2003 | Mitelberg et al. |
| 6,626,915 B2 | 9/2003 | Leveillee |
| 6,638,294 B1 | 10/2003 | Palmer |
| 6,645,152 B1 | 11/2003 | Jung et al. |
| 6,652,556 B1 | 11/2003 | VanTassel et al. |
| 6,783,538 B2 | 8/2004 | McGuckin, Jr. et al. |
| 6,939,362 B2 | 9/2005 | Boyle et al. |
| 6,958,074 B2 | 10/2005 | Russell |
| 7,282,055 B2 | 10/2007 | Tsuruta |
| 7,582,100 B2 | 9/2009 | Johnson et al. |
| 7,645,292 B2 | 1/2010 | Porter |
| 7,695,484 B2 | 4/2010 | Wallace et al. |
| 7,713,275 B2 | 5/2010 | Greenberg et al. |
| 7,753,918 B2 | 7/2010 | Hartley et al. |
| 7,776,052 B2 | 8/2010 | Greenberg et al. |
| 7,785,343 B2 | 8/2010 | Johnson et al. |
| 7,789,892 B2 | 9/2010 | Johnson et al. |
| 7,806,906 B2 | 10/2010 | Don Michael |
| 7,854,747 B2 | 12/2010 | Johnson et al. |
| 7,875,038 B2 | 1/2011 | Que et al. |
| 8,057,506 B2 | 11/2011 | Gilson et al. |
| 8,226,679 B2 | 7/2012 | Johnson et al. |
| 2001/0039432 A1 | 11/2001 | Whitcher et al. |
| 2002/0095171 A1 | 7/2002 | Belef |
| 2002/0107541 A1 | 8/2002 | Vale et al. |
| 2002/0120287 A1 | 8/2002 | Huter |
| 2002/0183783 A1 | 12/2002 | Shadduck |
| 2003/0040772 A1 | 2/2003 | Hyodoh et al. |
| 2003/0097114 A1 | 5/2003 | Ouriel et al. |
| 2003/0130684 A1 | 7/2003 | Brady et al. |
| 2003/0171774 A1 | 9/2003 | Freudenthal et al. |
| 2003/0171803 A1 | 9/2003 | Shimon |
| 2003/0212429 A1 | 11/2003 | Keegan et al. |
| 2004/0199201 A1 | 10/2004 | Kellett et al. |
| 2004/0220608 A1 | 11/2004 | D'Aquanni et al. |
| 2005/0107822 A1 | 5/2005 | WasDyke |
| 2005/0154416 A1 | 7/2005 | Herweck et al. |
| 2005/0177185 A1 | 8/2005 | Becker et al. |
| 2006/0020286 A1 | 1/2006 | Niermann |
| 2006/0069405 A1 | 3/2006 | Schaeffer et al. |
| 2006/0100658 A1 | 5/2006 | Obana et al. |
| 2006/0241677 A1 | 10/2006 | Johnson et al. |
| 2006/0241678 A1 | 10/2006 | Johnson et al. |
| 2006/0241679 A1 | 10/2006 | Johnson et al. |
| 2007/0123932 A1 | 5/2007 | Gray et al. |
| 2008/0004687 A1 | 1/2008 | Barbut et al. |
| 2008/0021497 A1 | 1/2008 | Johnson et al. |
| 2008/0033482 A1 | 2/2008 | Kusleika |
| 2008/0033534 A1 | 2/2008 | Cook et al. |
| 2008/0147111 A1 | 6/2008 | Johnson et al. |
| 2010/0318115 A1 | 12/2010 | Chanduszko et al. |
| 2010/0324590 A1 | 12/2010 | Johnson et al. |
| 2012/0022638 A1 | 1/2012 | Leewood et al. |
| 2012/0179196 A1 | 7/2012 | Johnson et al. |
| 2013/0012981 A1 | 1/2013 | Johnson et al. |
| 2013/0023981 A1 | 1/2013 | Dierking et al. |
| 2013/0035715 A1 | 2/2013 | Johnson et al. |

FOREIGN PATENT DOCUMENTS

| | | |
|---|---|---|
| JP | 10-509623 | 9/1998 |
| WO | WO 02/02162 A2 | 1/2002 |
| WO | WO 2005/102211 A1 | 11/2005 |
| WO | WO 2006/034233 A1 | 3/2006 |
| WO | WO 2006/074163 A2 | 7/2006 |

OTHER PUBLICATIONS

Siskin, Gary P.; Inferior Vena Cava Filters; eMedicine; Sep. 7, 2004.

Streiff, Michael B.; Vena caval filters; a comprehensive review; Blood; vol. 95; No. 12; pp. 3669-3677; Jun. 15, 2000.

Laroya et al.; U.S. Appl. No. 13/475,819 entitled "Retrieval Snare Device and Method," filed May 18, 2012.

Johnson et al.; U.S. Appl. No. 13/472,417 entitled "Distal Protection Filter," filed May 15, 2012.

Laroya et al.; U.S. Appl. No. 13/739,828 entitled "Retrieval Snare Device and Method," filed Jan. 11, 2013.

Johnson et al.; U.S. Appl. No. 13/791,464 entitled "Coated endoluminal filters," filed Mar. 8, 2013.

Johnson et al.; U.S. Appl. No. 13/791,557 entitled "Methods for providing protection during procedures in the vasculature," filed Mar. 8, 2013.

Johnson et al.; U.S. Appl. No. 13/802,657 entitled "Distal protection device," filed Mar. 13, 2013.

Johnson et al.; U.S. Appl. No. 14/574,203 entitled "Filter support members," filed Dec. 17, 2014.

Johnson et al.; U.S. Appl. No. 14/575,935 entitled "Extended anchor endoluminal filter," filed Dec. 18, 2014.

Johnson et al.; U.S. Appl. No. 14/578,087 entitled "Devices and methods for controlled endoluminal filter deployment," filed Dec. 19, 2015.

Johnson et al.; U.S. Appl. No. 14/581,638 entitled "Treatment structure and methods of use," filed Dec. 23, 2014.

Johnson et al.; U.S. Appl. No. 13/919,630 entitled "Methods for Maintaining a Filtering Device Within a Lumen," filed Jun. 17, 2013.

Johnson et al.; U.S. Appl. No. 13/919,658 entitled "Biodegradable Implant Device," filed Jun. 17, 2013.

(56) References Cited

OTHER PUBLICATIONS

Johnson et al.; U.S. Appl. No. 13/919,680 entitled "Endoluminal Filter," filed Jun. 17, 2013.
Johnson et al.; U.S. Appl. No. 13/919,718 entitled "Endoluminal Filter," filed Jun. 17, 2013.
Johnson et al.; U.S. Appl. No. 13/931,462 entitled "Retrievable Endoluminal Filter" filed Jun. 28, 2013.
Johnson et al.; U.S. Appl. No. 13/931,408 entitled "Endoluminal Filter," filed Jun. 28, 2013.
Johnson et al.; U.S. Appl. No. 13/931,334 entitled "Filter Delivery Methods," filed Jun. 28, 2013.
Johnson et al.; U.S. Appl. No. 13/931,256 entitled "Methods for Maintaining a Filtering Device Within a Lumen," filed Jun. 28, 2013.
Laroya et al.; U.S. Appl. No. 14/458,168 entitled "Retrieval Snare Device and Method," filed Aug. 12, 2014.
Johnson et al.; U.S. Appl. No. 14/372,180 entitled "Endoluminal Filter With Fixation," filed Jul. 14, 2014.

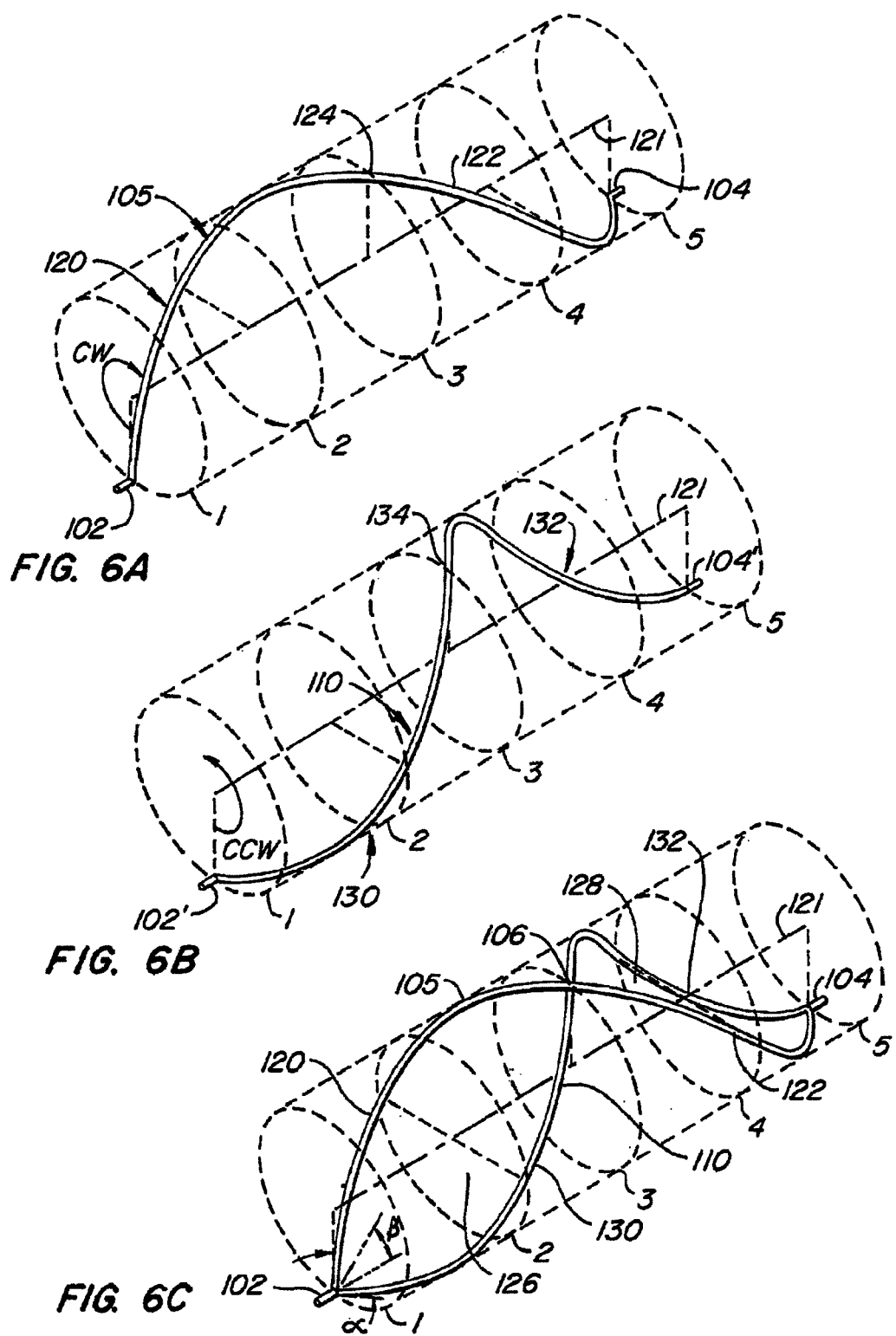

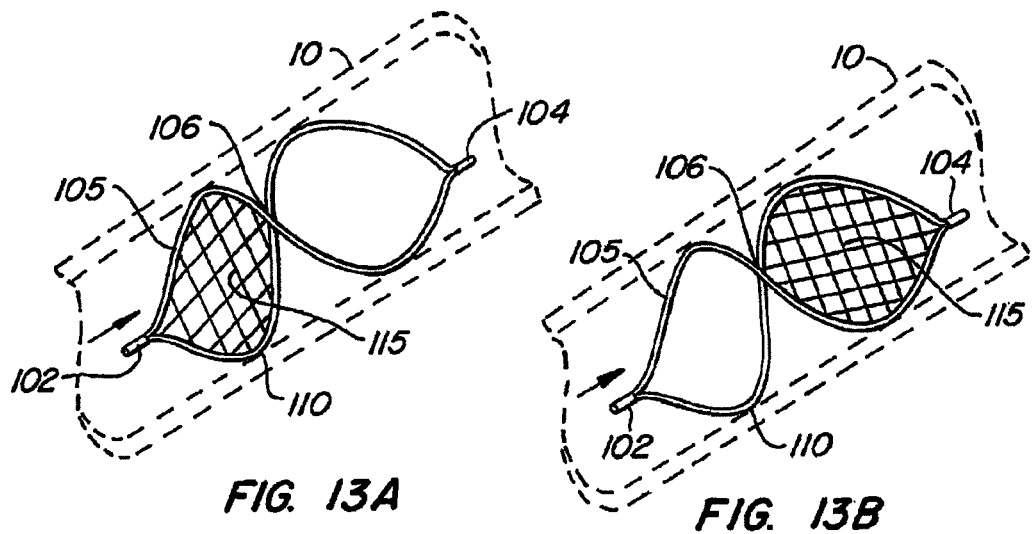
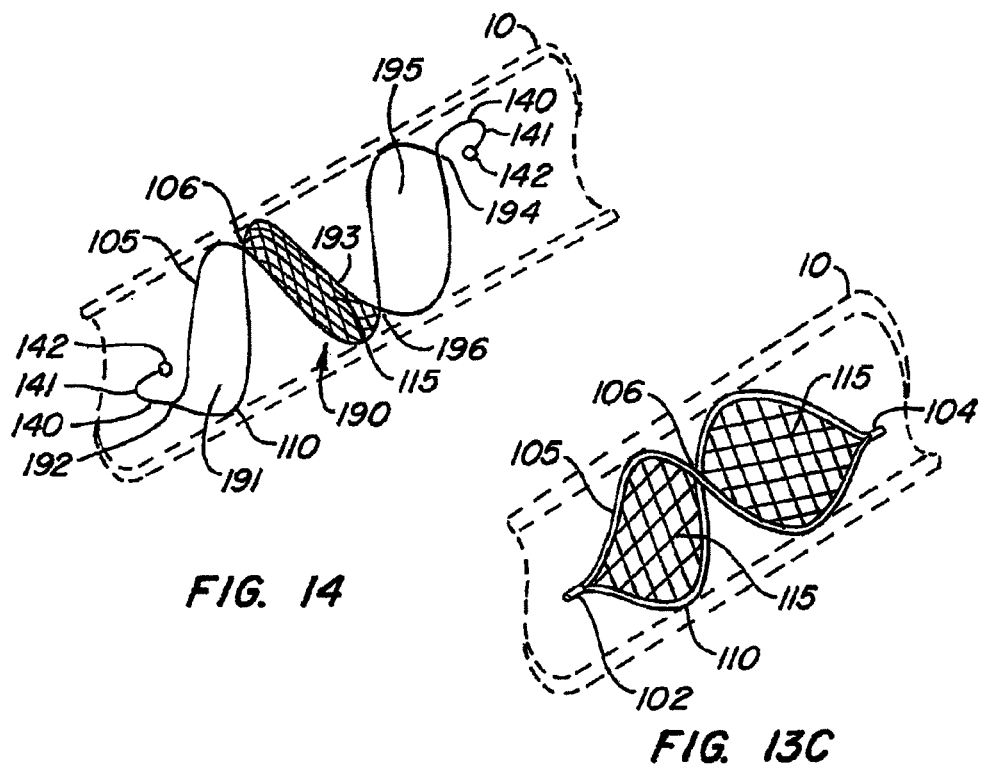

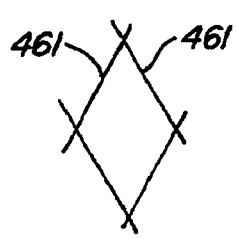 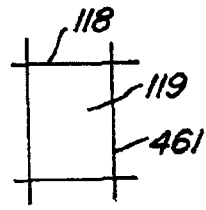 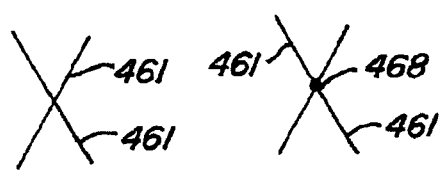
FIG. 54A    FIG. 54B    FIG. 54C    FIG. 55A
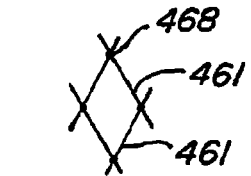 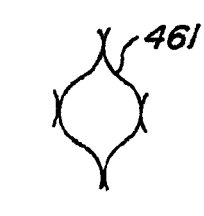 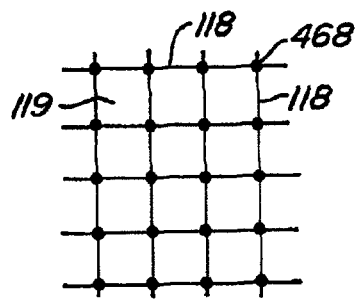
FIG. 55B    FIG. 55C    FIG. 55D
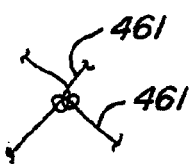  
FIG. 55E    FIG. 60A    FIG. 60B
  
FIG. 60C    FIG. 60D    FIG. 60E

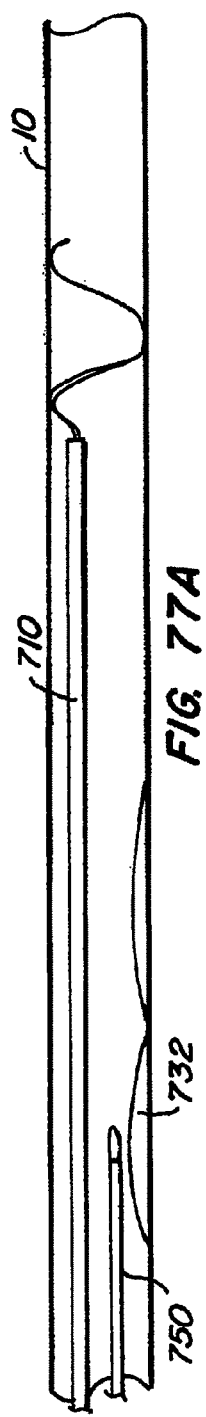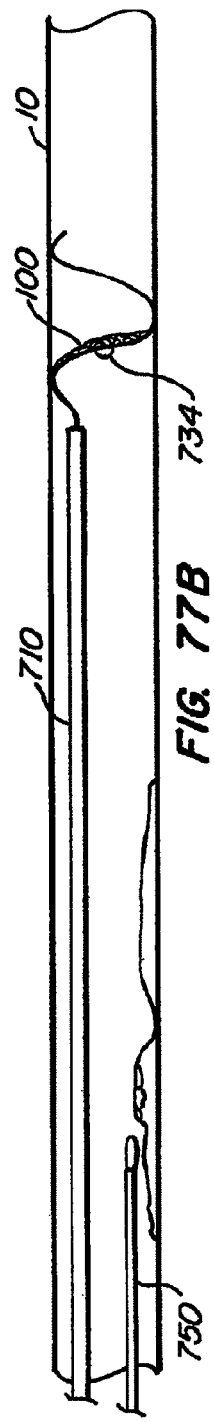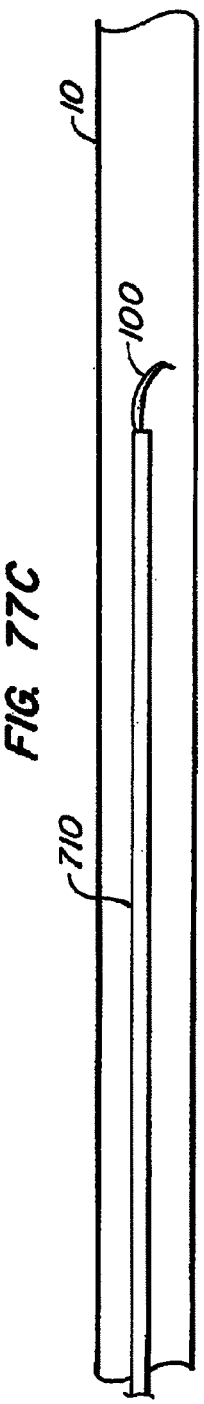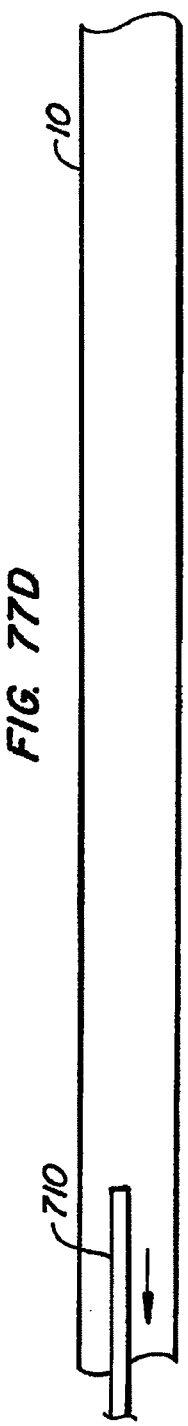

SPIRAL SHAPED FILTER

CROSS-REFERENCE TO RELATED APPLICATIONS

This application claims priority as a continuation of U.S. patent application Ser. No. 12/862,694, filed Aug. 24, 2010, titled "METHODS FOR MAINTAINING A FILTERING DEVICE WITHIN A LUMEN," now U.S. Patent Publication No. 2010-0324590-A1, which is a continuation of U.S. patent application Ser. No. 11/325,249, filed Jan. 3, 2006, titled "METHODS FOR MAINTAINING A FILTERING DEVICE WITHIN A LUMEN," now U.S. Patent Publication No. 2006-0241677-A1, which claims the benefit of U.S. Provisional Application No. 60/641,327, filed Jan. 3, 2005, titled "RETRIEVABLE INFERIOR VENA CAVA FILTER WIRE;" U.S. Provisional Application No. 60/668,548, filed Apr. 4, 2005, titled "WEB-BASED PULMONARY EMBOLI PROTECTION SYSTEM;" and U.S. Provisional Application No. 60/673,980, filed Apr. 21, 2005, titled "HELICAL EMBOLIC PROTECTION DEVICE AND RETRIEVAL METHODS," each of which are incorporated herein by reference in their entirety.

This application is related to the following patent applications: U.S. patent application Ser. No. 11/325,251, filed Jan. 3, 2006, titled "RETRIEVABLE ENDOLUMINAL FILTER," now U.S. Patent Publication No. 2006-0241678-A1; U.S. patent application Ser. No. 11/325,611, filed Jan. 3, 2006, titled "COATED ENDOLUMINAL FILTER," now U.S. Pat. No. 7,785,343; U.S. patent application Ser. No. 11/325,230, filed Jan. 3, 2006, titled "ENDOLUMINAL FILTER," now U.S. Pat. No. 7,854,747; U.S. patent application Ser. No. 11/325,622, filed Jan. 3, 2006, titled "ENDOLUMINAL FILTER," now U.S. Patent Publication No. 2008-0021497-A1; U.S. patent application Ser. No. 11/325,229, filed Jan. 3, 2006, titled "SPIRAL SHAPED FILTER," now U.S. Pat. No. 7,582,100; U.S. patent application Ser. No. 11/325,273, filed Jan. 3, 2006, titled "FILTER DELIVERY METHODS," now U.S. Patent Publication No. 2006-0241679-A1; U.S. patent application Ser. No. 11/325,247, filed Jan. 3, 2006, titled "LUMEN FILTERING METHODS," now U.S. Pat. No. 7,789,892; U.S. patent application Ser. No. 11/969,827, filed Jan. 4, 2008, titled "ENDOLUMINAL FILTER WITH FIXATION," now U.S. Patent Publication No. 2008-0147111-A1; U.S. patent application Ser. No. 12/541,788, filed Aug. 14, 2009, titled "SPIRAL SHAPED FILTER," now U.S. Pat. No. 8,226,679; International Patent Application No. PCT/US2006/000087, filed Jan. 3, 2006, titled "RETRIEVABLE ENDOLUMINAL FILTER," now Publication No. WO2006/074163; and International Patent Application No. PCT/US2008/088606, filed Dec. 31, 2008, titled "ENDOLUMINAL FILTER WITH FIXATION," now Publication No. WO2009/088905, each of the above applications are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

This invention relates generally to devices and methods for providing filtration of debris within a body lumen. More particularly, the invention provides a retrievable filter placed percutaneously in the vasculature of a patient to prevent passage of emboli. Additionally, embodiments of the invention provide a filter that can be atraumatically positioned and subsequently removed percutaneously from a blood vessel using either end of the filter.

Embolic protection is utilized throughout the vasculature to prevent the potentially fatal passage of embolic material in the bloodstream to smaller vessels where it can obstruct blood flow. The dislodgement of embolic material is often associated with procedures which open blood vessels to restore natural blood flow such as stenting, angioplasty, arthrectomy, endarterectomy or thrombectomy. Used as an adjunct to these procedures, embolic protection devices trap debris and provide a means for removal for the body.

One widely used embolic protection application is the placement of filtration means in the vena cava. Vena cava filters (VCF) prevent the passage of thrombus from the deep veins of the legs into the blood stream and ultimately to the lungs. This condition is known as deep vein thrombosis (DVT), which can cause a potentially fatal condition known as pulmonary embolism (PE).

The first surgical treatment for PE, performed by John Hunter in 1874, was femoral vein ligation. The next major advancement, introduced in the 1950's, was the practice of compartmentalizing of the vena cava using clips, suture or staples. While effective at preventing PE, these methods were associated with significant mortality and morbidity (see, e.g., Kinney TB, Update on inferior vena cava filters, JVIR 2003; 14:425-440, incorporated herein by reference).

A major improvement in PE treatment, in which venous blood flow was maintained, was presented by DeWesse in 1955. This method was called the "harp-string" filter, as represented in FIG. 1A and FIG. 1B, in which strands of silk suture 12 were sewn across the vena cava 11 in a tangential plane below the renal veins 13 to trap thrombus. Reported clinical results demonstrated the effectiveness of this method in preventing PE and maintaining caval patency. (see, e.g., DeWeese M S, A vena cava filter for the prevention of pulmonary embolism, Arch of Surg 1963; 86:852-868, incorporated herein by reference). Operative mortality associated with all of these surgical treatments remained high and therefore limited their applicability.

The current generation of inferior vena cava (IVC) filters began in 1967 with the introduction of the Mobin-Uddin umbrella 21 (FIG. 1C) which is described in further detail in U.S. Pat. No. 3,540,431. The Greenfield filter (FIG. 1D) was introduced in 1973 and is described in further detail in U.S. Pat. No. 3,952,747. These conical-shaped devices were placed endoluminaly in the IVC and utilized hooks or barbs 20, 30 to pierce the IVC wall and fix the position of the device. A variety of conical-shaped, percutaneously placed vena cava filters, based upon this concept are now available. For example, the TULIP with a filter structure 41 (FIG. 1E) further described in U.S. Pat. No. 5,133,733; the RECOVERY with a filter structure 51 (FIG. 1F) further described in U.S. Pat. No. 6,258,026; and the TRAPESE with a filter structure 61 (FIG. 1G) further described in U.S. Pat. No. 6,443,972.

The next advancement in filters added the element of recoverability. Retrievable filters were designed to allow removal from the patient subsequent to initial placement. Retrievable filters are generally effective at preventing PE yet they have a number of shortcomings, such as, for example: failure of the device to deploy into the vessel properly, migration, perforation of the vessel wall, support structure fracture, retrievability actually limited to specific circumstances, and formation of thrombosis on or about the device.

Problems associated with retrievable, conical-shaped devices, such as those illustrated in FIG. 1D, FIG. 1E and FIG. 1F, have been reported in the medical literature. These reported problems include tilting which makes it difficult to recapture the device and compromises filtration capacity. Hooks 30, 40, 50, 60 used to secure these devices have been reported to perforate the vessel wall, cause delivery complications, and fracture. A partially retrievable system is described in detail in pending U.S. Patent Publication No. 2004/0186512 (FIG. 1H). In this system, the filter portion 71 can be removed from the support structure 70, but the support structure remains in-vivo. All of these described devices share the common limitation that they can be retrieved from only one end. Each of the above referenced articles, patents and patent application are incorporated herein in its entirety.

In view of the many shortcomings and challenges that remain in the field of endoluminal filtering, there remains a need for improved retrievable, endoluminal filters.

SUMMARY OF THE DISCLOSURE

In general, in one embodiment, a filter can includes a first spiral support member having a first end and a second end; a second spiral support member positioned adjacent the first spiral support member to form a loop between the first end and the second end; a material covering a portion of the first and the second spiral support members; and a structure attached to the loop.

This and other embodiments can include one or more of the following features. In one aspect, structure can be attached to the material. In another aspect, the filter can further include another material between the material and the support members. In another aspect, the another material can be one of ePTFE, PTFE, PET, PFA, or FEP. In yet another aspect, the material can be wrapped around the first and the second spiral support members and the another material. In still another aspect, the another material can cover the portion of the first and the second spiral support members covered by the material. In a further aspect, the material and the another material can be part of a multi-lumen structure. In another aspect, the structure can be attached to the loop by the wrapped material. In an additional aspect, the structure can be attached to one lumen of the multi-lumen structure. In still another aspect, the material can be a multi-lumen structure. In an additional aspect, the multi-lumen structure can be configured to release a pharmacological agent. In another aspect, a lumen of the multi-lumen structure can be at least partially filled with a pharmacological agent.

BRIEF DESCRIPTION OF THE DRAWINGS

A better understanding of the features and advantages of embodiments of the present invention will be appreciated through reference to the following detailed description that sets forth illustrative embodiments and the accompanying drawings of which:

FIGS. 6A-8D illustrate various aspects of the structural members in a filtering device;

FIGS. 11-13C illustrate various aspects of and configurations for material capture structures;

FIGS. 54A-65F illustrate several alternative filtering structures;

FIGS. 75A-78F illustrate several exemplary methods of using a filtering device;

DETAILED DESCRIPTION

Figure 1A:
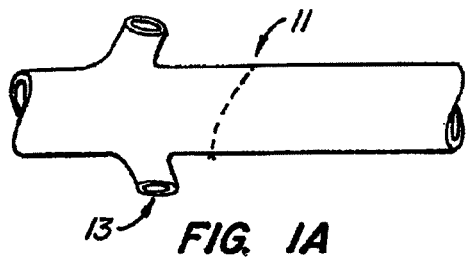
FIGS. 1A-1H illustrate various prior art filters.
Figure 1B:
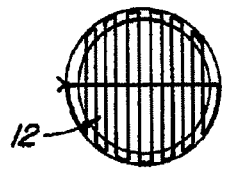
Figure 1C:
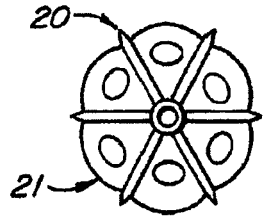
Figure 1D:
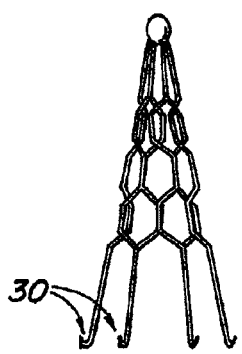
Figure 1E:
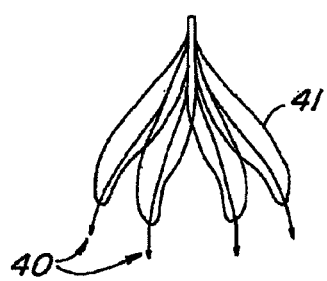
Figure 1F:
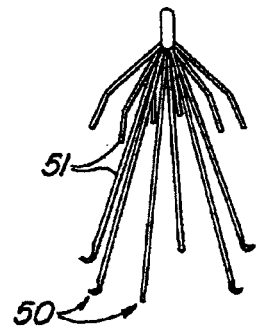
Figure 1G:
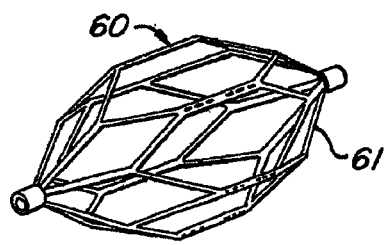
Figure 1H:
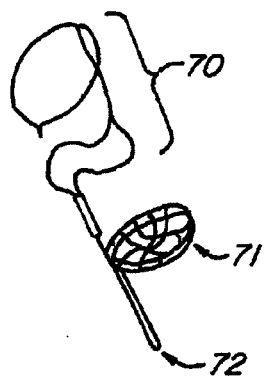

There remains a clinical need for improved endoluminal filter devices and methods. Improved endoluminal filter devices provide effective filtration over a range of lumen sizes and are easy to deploy into and retrieve from a lumen. In addition, improved endoluminal filter devices minimize thrombosis formation or tissue ingrowth on the device and are resistant to migration along the lumen. Improved endoluminal filter devices also minimize device fatigue by eliminating barbs, hooks or other sharp curve design features that can produce stress points that lead to fatigue. Embodiments of the filter devices of the present invention provide many and in some cases all of the features of improved endoluminal filters and have a number of uses such but are not limited to: embolic protection, thrombectomy, vessel occlusion, and tethered or untethered distal protection.

Several embodiments of the present invention provide improved filtration devices that are durable, provide effective and nearly constant filter capacity over a range of lumen sizes and are easily delivered and removed from a lumen via either end of the device. Additionally, embodiments of the present invention can be delivered into and retrieved from a lumen using minimally invasive surgical techniques. One aspect of an embodiment of the present invention is the construction of support structure elements using a shape memory material. The shape memory material may have a pre-shaped form that ensures the support elements are uniformly collapsible and, when deployed, provides a pre-defined range of controllable force against the lumen wall without use of hooks or barbs.

The elongate support structure elements are configured to collapse and expand with natural vessel movements while maintaining constant apposition with the vessel wall. One result is that the support structure shape and size track to vessel movements. As a result, the filter density and capacity of embodiments of the present invention remain relatively independent of changes in vessel size. Moreover, the self centering aspect of the support structure ensures the filtration device provides uniform filtration across the vessel diameter. As such, embodiments of the present invention provide generally constant filtration capacity of the device is maintained across the entire vessel lumen and during vessel contractions and expansions.

Uniform filter capacity is a significant improvement over conventional devices. Conventional devices typically have a filter capacity that varies radially across a lumen. The radial variation in filter capacity usually results from the fact that conventional filtration elements have a generally wider spacing at the periphery of the lumen and closer spacing along the central lumen axis. The result is that larger emboli can escape along the lumen periphery. During vessel expansions and contractions, the radial variations in filter capacity are exacerbated in conventional devices.

Another advantage of some embodiments of the present invention is that when released from a constrained state (i.e., within a delivery sheath), the device assumes a pre-determined form with elongate support members that extend along and self center the device in the vessel. These elongate support members exert atraumatic radial force against the vessel wall to prevent or minimize device migration. Utilizing radial force generated by the elongate support members obviates the need for hooks or barbs to secure the device within the vessel. As a result, embodiments of the present invention produce little or no damage to the vessel wall and lining while producing little or no systemic response from the body. Additionally, when device retrieval is initiated, the uniformly collapsible form of the elongate support members causes the elongate support members to pull away from the vessel wall as the device is being re-sheathed. The movement of the elongate members away from the vessel wall facilitates the atraumatic removal of the device from the vessel wall.

Additional embodiments of the present invention may include a retrieval on one or both ends of the device. The use of retrieval features on both ends of the device allows deployment, repositioning and removal of the device to be accomplished from either end of the device. As a result, the use of retrieval features on both ends of the device enables both antegrade or retrograde approaches to be used with a single device. The retrieval feature may be integral to another structural member or a separate component. In some embodiments, the retrieval feature is collapsible and may have a curved shape or a generally sinusoidal shape. Additional aspects of retrieval features are described below.

General Principals and Construction

Figure 2A:
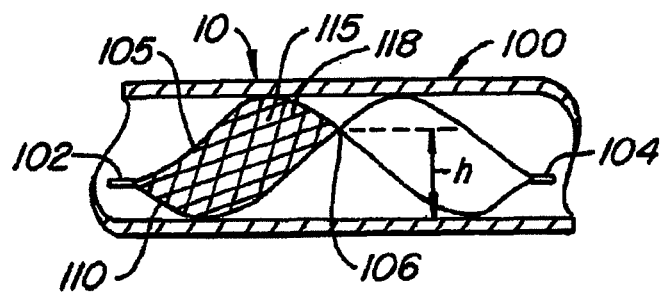
FIGS. 2A-2C illustrate the response of a filtering device to changes in lumen size.

FIG. 2A illustrates an embodiment of a filtering device 100 of the present invention positioned within a lumen 10. The lumen 10 is cut away to show the position of filter 100 deployed into within a lumen and in contact with the lumen wall. The filter 100 includes a first elongate member 105 and a second elongate member 110. The elongate members are joined to form ends 102, 104. The elongate members cross but are not joined to one another at crossover 106. In one embodiment, the elongate members have first and second sections. First sections extend between the end 102 and the crossover 106 and the second sections extend from the crossover 106 to the second end 104. While some embodiments contact the lumen in different ways, the illustrated embodiment has the ends 102, 104 against one side of the lumen interior wall while the crossover 106 contacts the other side of the lumen interior wall with the elongate bodies in constant or nearly constant apposition along the lumen interior wall between the ends 102, 104.

Material (i.e., thrombus, plaque and the like) flowing through the lumen 10 of a size larger than the filtering size of the material capture structure 115 is captured between or cut down by the filaments 118. In the illustrated embodiment of FIG. 2A, the material capture structure 115 is supported by a rounded frame formed by the elongate members 105, 110 formed between the end 102 and the crossover 106. Another rounded frame formed between the crossover 106 and the second end 104 and could also be used to support a material capture structure of the same or different construction and filter capacity of the a material capture structure 115. As such, a material removal structure supported by one rounded frame may be configured to remove material of a first size and the material removal structure supported a the other rounded frame may be configured to remove material of a second size. In one embodiment, the material removal structure in the upstream rounded frame removes larger size debris than material removal structure in the downstream rounded frame. Also illustrated in FIGS. 2A-2C is how the filter cells 119 that make up the material capture structure is 115 maintain their size and shape relatively independent of movement of the first and second structural members 105, 110 over a physiological range of vessel diameters.

Figure 2B:
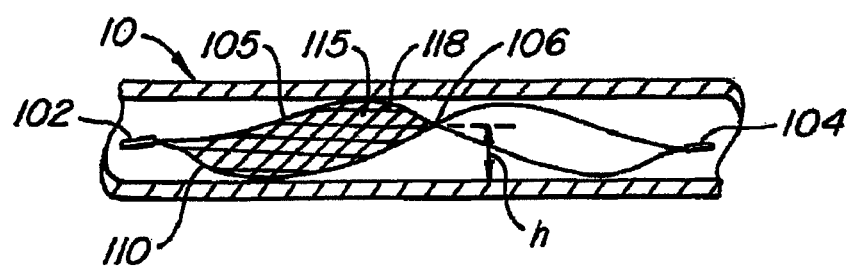
Figure 2C:
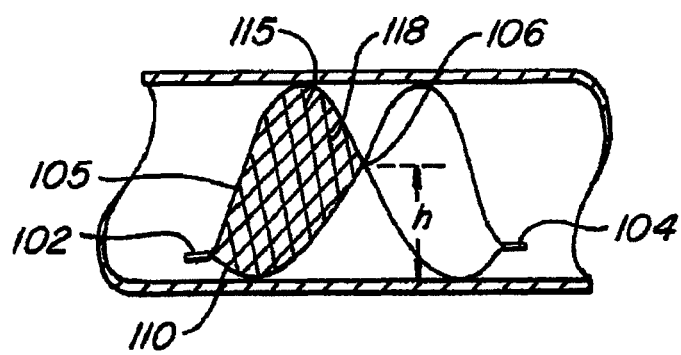

FIGS. 2B and 2C illustrate how the elongate support structure elements of embodiments of the present invention are configured to collapse and expand with natural vessel movements while maintaining constant apposition with the vessel wall. FIGS. 2A, 2B and 2C also illustrate how devices according to embodiments of the present invention are both radially and axially elastic. In response to vessel size changes, ends 102, 104 move out as the vessel size decreases (FIG. 2B) and then move in as the vessel size increases (FIG. 2C). In addition, the device height "h" (measured from the lumen wall in contact with ends 102, 104 to crossover) also changes. Device height "h" changes in direct relation to changes in vessel diameter (i.e., vessel diameter increases will increase device height "h"). As such, device height ("h") in FIG. 2C is greater than device height ("h") in FIG. 2A which is in turn greater than the device height ("h") in FIG. 2B.

FIGS. 2A, 2B and 2C also illustrate how a single sized device can be used to accommodate three different lumen diameters. FIG. 2C illustrates a large lumen, FIG. 2A a medium sized lumen and FIG. 2B a small sized lumen. As these figures make clear, one device can adapt to cover a range of vessel sizes. It is believed that only 3 device sizes are needed to cover the range of human vena cava interior diameters that range from approximately 12-30 mm with an average interior diameter of 20 mm. Also illustrated is the static or nearly static filter capacity of the material capture structure 115. In each different vessel size, the material capture structure 115, the filaments 118 and filter cell 119 maintain the same or nearly the same shape and orientation within the support frame formed by the elongate bodies. These figures also illustrate the dynamic shape changing aspect of the device that may also be used to accommodate and conform to vessel irregularities, tortuosity, flares and tapers and while remaining in apposition to the wall. Because each elongate body may move with a high degree of independence with respect to the other, the loops or support frames formed by the elongate bodies can also independently match the shape/diameter of the lumen section in which it is placed.

Figure 3:
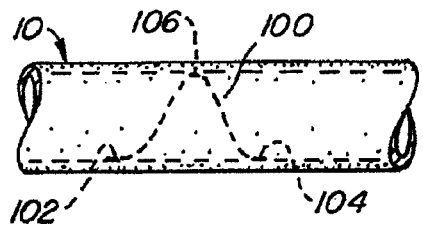
FIGS. 3-5 illustrate the interaction of a structural member with a lumen wall.
Figure 3A:
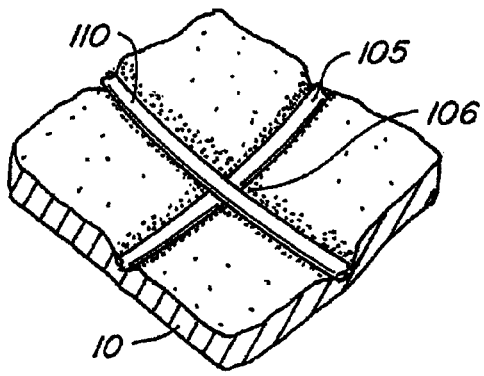
Figure 3B:
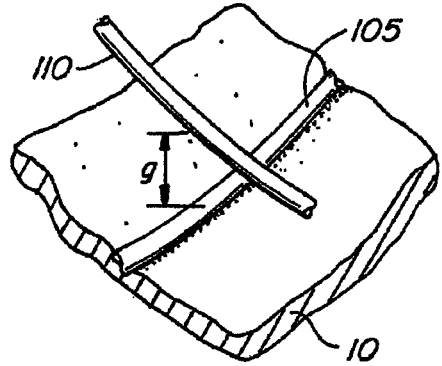

FIGS. 3, 3A and 3B illustrate the device 100 deployed into the lumen 10. As illustrated in FIG. 3, the device 100 is oriented in the lumen with the ends 102, 104 along one side of the interior vessel wall with the crossover 106 on the opposite side. FIG. 3 illustrates an embodiment of a device of the present invention that is shaped to fit within the lumen 10 without distending the lumen. In FIG. 3A the elongate bodies 105, 110 are in contact but are not joined at crossover 106. In FIG. 3B the elongate bodies 105, 110 cross one another at crossover 106 but are separated (i.e., by a gap "g").

Figure 4:
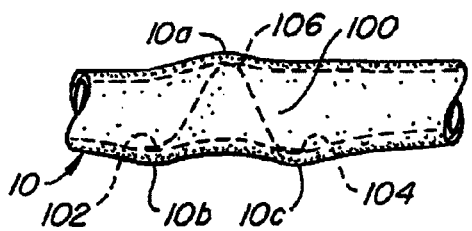
Figure 5:
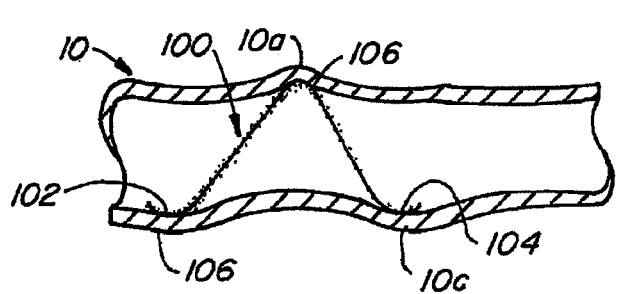

FIGS. 4 and 5 illustrate how aspects of the device design can be modified to increase the radial force applied against the interior wall of lumen 10. Devices having increased fixation force may be useful for some applications, such as vessel occlusion or for distal protection when a large amount of debris is expected. If a device is not intended to be retrieved (i.e., permanently installed into a lumen) then high radial force design devices may be used to ensure the device remains in place and distention may be used to trigger a systemic response (i.e., a tissue growth response) in the lumen to ensure device ingrowth and incorporation with the lumen interior wall.

Filter device embodiments of the present invention having low or atraumatic radial force are particularly useful in retrievable devices. As used herein, atraumatic radial force refer to radial forces produced by a filtering device embodiment that meets one or more of the following: radial forces high enough to hold the device in place with little or no migration and without damaging or overly distending the lumen interior wall; radial forces high enough to hold the device in place but while triggering little or no systemic response for the vessel wall; or forces generated by device operation that trigger reduced systemic response or a systemic response below that of a conventional filter.

In contrast to the device sized in FIG. 3 to minimize vessel distention, FIG. 4 illustrates a device 100 configured to exert greater radial force to a degree to cause lumen wall to distend. FIGS. 4 and 5 illustrate lumen wall distention by the end 102 (distention 10b), by the crossover 106 (distention 10a), and by the end 104 (distention 10c). Although not shown in these figures, the elongate bodies would likely distend the lumen along their length as well.

The radial force of a device may be increased using a number of design factors. Radial force may be increased by increasing the rigidity of the elongate body by, for example, using an elongate body with a larger diameter. Radial force may also be increased when forming the shapes of the elongate bodies (i.e., during the heat treat/set processes for Nitinol devices and the like), as well as in the material composition and configuration.

Additional details of an embodiment of the support members 105, 110 may be appreciated with reference to FIGS. 6A, 6B and 6C. FIGS. 6A, 6B illustrate the support members separately and then assembled together (FIG. 6C) about device axis 121. In general, the device axis 121 is the same as the axis along the central of a lumen into which the device is deployed. For purposes of illustration, the support members 105, 110 will be described with reference to a sectioned lumen shown in phantom having a generally cylindrical shape. The support members may also be thought of as deployed within and/or extending along the surface of an imaginary cylinder.

In the illustrative embodiments of FIGS. 6A, 6B and 6C, the support members 105, 110 are shown in an expanded, pre-defined shape. In one embodiment, the support members are formed from MRI compatible materials. The support members contain no sharp bends or angles to produce stress risers that may lead to fatigue issues, vessel erosion, and facilitate device collapse. In some embodiments, each elongate member is conventionally formed by constraining a shape memory material such as a shape memory metal alloy or shape memory polymer on a cylindrical shaping mandrel that contains pins to constrain the material into the desired shape. It should be noted that due to the low strain rates of the axial members during deployment, other flexible materials and metals can be utilized. These include but are not limited to Stainless Steel, various alloys, and some polymers such as PTFE, Polyamide, PEEK, etc. Thereafter, the material can be subjected to a suitable conventional heat treatment process to set the shape. One or more planes of symmetry (i.e., FIG. 15) may be provided, for example, by forming both elongate members on a single mandrel and at the same time. Other conventional processing techniques may also be used to produce symmetrical filtering device embodiments. Additionally, retrieval features described herein (if present) may be directly formed on the wire ends during support member processing. In addition, multiple devices, in a series on a long mandrel, can be made using these methods.

Examples of suitable shape memory alloy materials include, for example, copper-zinc-aluminium, copper-aluminum-nickel, and nickel-titanium (NiTi or Nitinol) alloys. Nitinol support structures have been used to construct a number of working prototypes of filter devices of the present invention as well as for use in ongoing animal studies (see experimental results discussion below). Shape memory polymers may also be used to form components of the filter device embodiments of the present invention. In general, one component, oligo(e-caprolactone) dimethacrylate, furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored over a wide range. Additional details of shape memory polymers are described in U.S. Pat. No. 6,388,043 which is incorporated herein by reference in its entirety. In addition, shape memory polymers could be designed to degrade. Biodegradable shape memory polymers are described in U.S. Pat. No. 6,160,084 which is incorporated herein by reference in its entirety.

It is believed that biodegradable polymers may also be suited to form components of the filter device embodiments of the present invention. For example, polylactide (PLA), a biodegradable polymer, has been used in a number of medical device applications including, for example, tissue screws, tacks, and suture anchors, as well as systems for meniscus and cartilage repair. A range of synthetic biodegradable polymers are available, including, for example, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene. Additionally, a number of biodegradable polymers derived from natural sources are available such as modified polysaccharides (cellulose, chitin, dextran) or modified proteins (fibrin, casein). The most widely compounds in commercial applications include PGA and PLA, followed by PLGA, poly(e-caprolactone), polydioxanone, trimethylene carbonate, and polyanhydride.

While described as forming the support structures, it is to be appreciated that other portions of the filter device may also be formed from shape memory alloys, shape memory polymers or biodegradable polymers. Other filter device components that may also be formed from shape memory alloys, shape memory polymers or biodegradable polymers include, for example, all or a portion of a retrieval feature, a material capture structure or an attachment between a material capture structure and a support structure.

FIG. 6A illustrates the first support member 105 extending from an end 102 to an end 104 along in a clockwise manner about the lumen interior wall (sectioned phantom lines) and the device axis 121. The support member 105 extends from the end 102 in section 1 at the 6 o'clock position, up to the 9 o'clock position in section 2, the 12 o'clock position in section 3, the 3 o'clock position in section 4 to the end 104 at the 6 o'clock position in section 5. The support member 105 has a two sections 120, 122 on either side of an inflection point 124. The inflection point 124 is positioned at about the 12 o'clock position in section 3. The radius of curvature of the sections 120, 122 may be the same or different. The cross section shape of the support member 105 is generally circular but may have one or more different cross section shapes in alternative embodiments.

FIG. 6B illustrates the second support member 105 extending from an end 102' to an end 104' along in a counter-clockwise manner about the lumen interior wall (sectioned phantom lines) and the device axis 121. The support member 110 extends from the end 102' in section 1 at the 6 o'clock position, up to the 3 o'clock position in section 2, the 12 o'clock position in section 3, 9 o'clock position in section 4 to the end 104' at the 6 o'clock position in section 5. The support member 110 has two sections 130, 132 on either side of an inflection point 134. The inflection point 134 is positioned at about the 12 o'clock position in section 3. The radius of curvature of the sections 120, 122 may be the same or different. The cross section shape of the support member 105 is generally circular but may have one or more different cross section shapes in alternative embodiments.

Figure 7A:
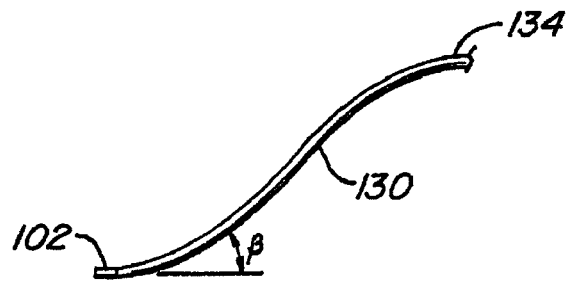
Figure 7B:
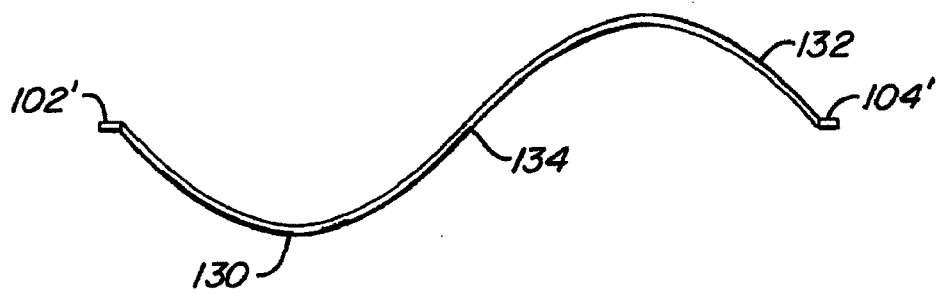
Figure 7C:
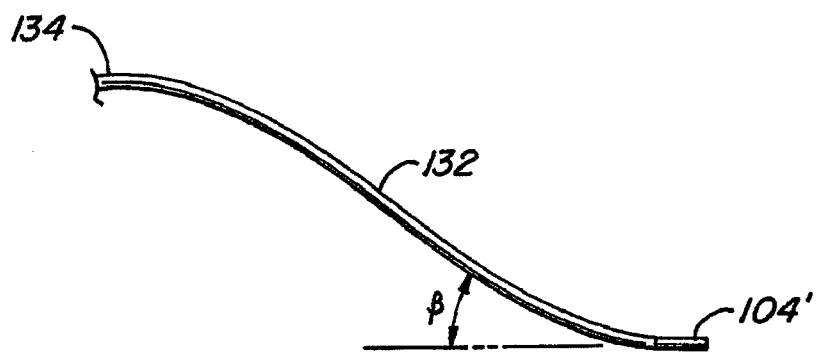

FIG. 6C illustrates the crossover 106 and first and second support members 105, 110 joined together at the ends. The first sections 120, 130 form a rounded frame 126. The angle β is formed by a portion of the lumen wall contacting end 102 and a plane containing the frame 126 and is referred to as the take off angle for the elongate members at end 102. In one alternative, the angle β is formed by a portion of the lumen wall contacting end 102 and a plane containing all or a portion of one or both sections 120, 130. In yet another alternative, the angle β is formed by a portion of the lumen wall contacting end 102 and a plane containing all or a portion of end 102 and all or a portion of the crossover 106. Another angle β is formed on end 104 as discussed above but in the context of end 104, a portion of the lumen wall contacting end 104, sections 122, 132 and the rounded frame 128 as illustrated in FIGS. 7A-7C. An angle formed by the support frames 126, 128 ranges generally between 20 degrees to 160 degrees in some embodiments and generally between 45 degrees to 120 degrees in some other embodiments.

FIG. 7A is a side view of section 130 in FIG. 6B, FIG. 7B is a top down view of FIG. 6B and FIG. 7C is side view of section 132 in FIG. 6B. The angle β ranges generally between 20 degrees to 160 degrees in some embodiments and generally between 45 degrees to 120 degrees in some other embodiments. The angle α is formed by a portion of section 120, a portion of section 130 and the end 102. Alternatively, the angle α is formed by the end 102 and tangents formed with a portion of the sections 120, 130. Another angle α is formed on end 104 as discussed above but in the context of end 104, a portion of the lumen wall contacting end 104 and sections 122, 132. The angle α ranges generally between 40 degrees to 170 degrees in some embodiments and generally between 70 degrees to 140 degrees in some other embodiments.

Figure 7D:
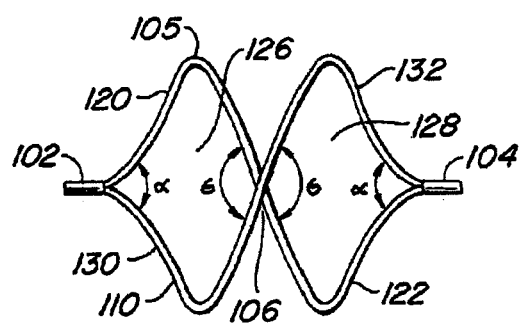
Figure 7E:
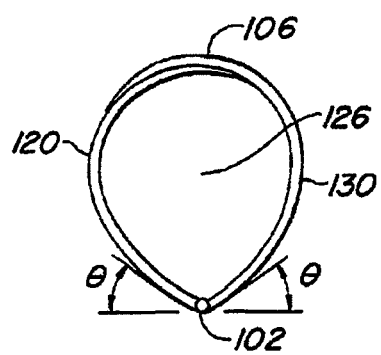

FIG. 7D illustrates a top down view of FIG. 6C. The angle σ is defined as the angle between a portion of section 120 between the inflection point 124 and the end 102 on one side and a portion of section 130 between the inflection point 134 and the end 102' on the other side. The angle σ is also defined as the angle between a portion of section 122 between the inflection point 124 and the end 104 on one side and a portion of section 132 between the inflection point 134 and the end 104' on the other side. The angle σ defined by sections 120, 130 may be the same, larger, or smaller than the angle σ formed by the sections 122, 132. The angle σ ranges generally between 10 degrees to 180 degrees in some embodiments and generally between 45 degrees to 160 degrees in some other embodiments.

FIG. 7D illustrates an end view of FIG. 6C taken from end 102. The angle θ is defined as the angle between a plane tangent to a portion of section 120 and a plane containing the end 102 that is also generally parallel to the device axis 121. An angle θ may also be defined as the angle between a plane tangent to a portion of section 130 and a plane containing the end 102 that is also generally parallel to the device axis 121. The angle θ defined by section 120 may be the same, larger, or smaller than the angle θ formed by the section 130. Similarly, an angle θ may be defined as discussed above and using as the angle between a plane tangent to a portion of section 122 or 132 and a plane containing the end 102 that is also generally parallel to the device axis 121. The angle θ ranges generally between 5 degrees to 70 degrees in some embodiments and generally between 20 degrees to 55 degrees in some other embodiments.

Figure 7F:
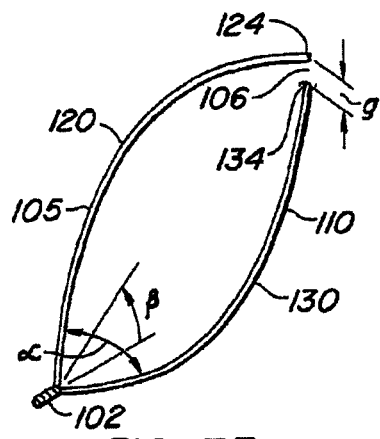
Figure 7G:
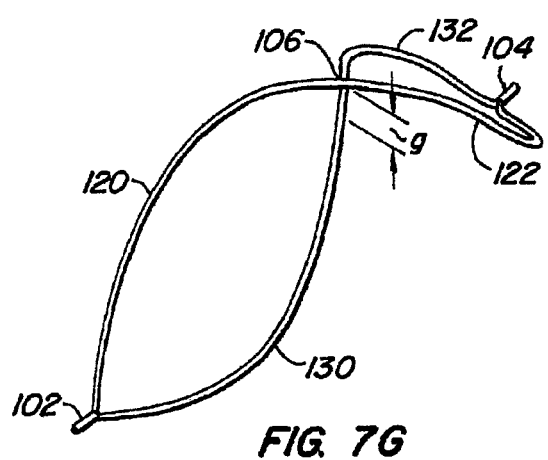

FIGS. 7F and 7G are perspective views of an alternative embodiment of the device illustrated in FIG. 6C. In the embodiment illustrated in FIGS. 7F and 7G, the support member 110 crosses underneath and does not contact the support member 105 at the crossover 106. The gap "g" between the support members is also illustrated in the FIG. 7G.

Figure 8A:
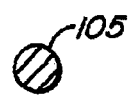
Figure 8B:
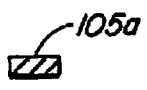
Figure 8C:
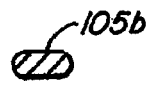
Figure 8D:
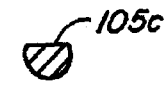

FIG. 8A illustrates the elongate body 105 with a generally circular cross section. However, many other cross section shapes are possible and may be used such as, for example, rectangular elongate body 105a (FIG. 8B), rectangular elongate body with rounded edges (not shown), oval elongate body 105b (FIG. 8C) and circular elongate body with a flattened edge 105c (FIG. 8D). In some embodiments, an elongate body will have the same cross section along its length. In other embodiments, an elongate body will have different cross sections along its length. In another embodiment, an elongate body has a number of segments and each segment has a cross section shape. The segment cross section shapes may be the same or different. The cross section shape of the elongate member is a factor used to obtain the desired radial force along the elongate member. The material used to form the elongate body (i.e., a biocompatible metal alloy such as Nitinol) may be drawn to have a desired cross section shape, or drawn in one cross section shape and then treated using conventional techniques such as grinding, laser cutting and the like to obtain the cross section shape were desired.

Figure 9A:
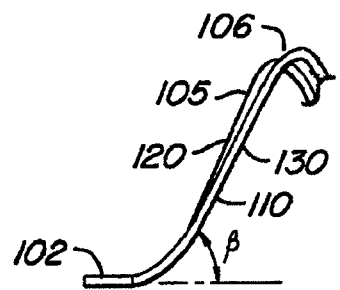
FIGS. 9A and 9B illustrate various aspects of a generally planer support frame.
Figure 9B:
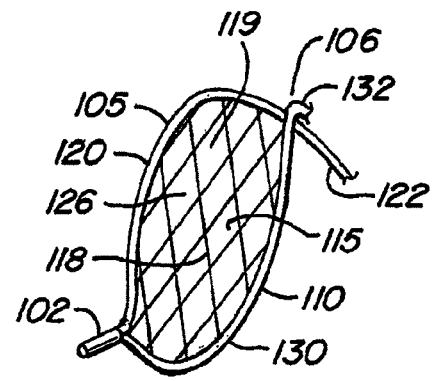

FIGS. 9A, 9B illustrate an embodiment of a material capture structure 115 extended across a generally planar, rounded frame 126 formed by the support members. FIG. 9A is a slight perspective view of a side view of the device. In this embodiment, sections 120, 130 of the support members lie mostly within in a single plane (i.e., in a side view of FIG. 9A section 110 is visible and blocks view of section 120) that also holds the rounded frame 126. FIG. 9B is a perspective view showing the material capture structure 115 extended between and attached to rounded frame 126. In this embodiment, the capture structure 115 extends across and is attached to the first sections 120, 130. In this embodiment, the material capture structure is a plurality of generally rectangular filter cells 119 formed by intersecting filaments 118. Other types of filter structures are described in greater detail below and may also be supported by the support frames formed by the structural members. In some embodiments such as FIGS. 9A and 9B, the angle β may also define the angle between the device axis and a plane containing a material capture structure.

Figure 10A:
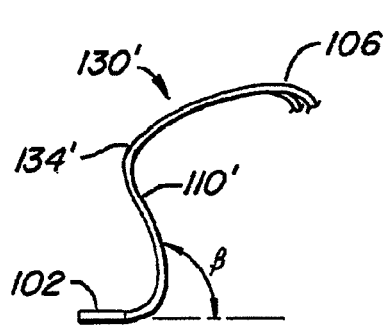
FIGS. 10A and 10B illustrate various aspects of a non-planer support frame.
Figure 10B:
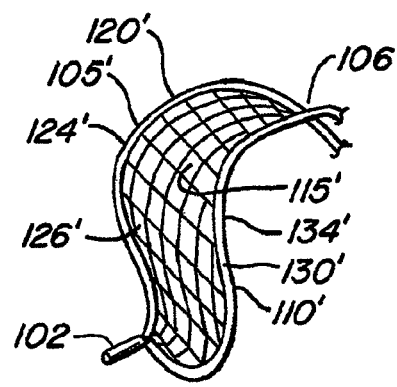

The support frame 126 and the material capture structure 115 is not limited to planar configurations. Non-planar and compound configurations, for example, are also possible as illustrated in FIGS. 10A and 10B. FIG. 10A is a side view of a non-planar structural support 110' having another inflection point 134' between the inflection point 134 and the end 102. The structural support 110' has more than one different radius of curvature between the end 102 and the crossover 106. In some embodiments, there could be more than one radius of curvature between the end 102 and the inflection point 134' as well as be more than one radius of curvature between the inflection point 134' and the inflection point 134. As a result, section 130' is a section possibly having different shapes, a number of different curvatures and at least one inflection point. As seen in FIG. 10B, the support structure 105' is also non-planar with more than one different radius of curvature between the end 102 and the inflection point 124. In some embodiments, there could be more than one radius of curvature between the end 102 and the inflection point 124' as well as be more than one radius of curvature between the inflection point 124' and the inflection point 124. As a result, section 120' is a section having different shapes, a number of different curvatures and one or more inflection points. Similar non-planar configurations may be used on end 104. The material capture structure 115' is adapted to conform to the shape of non-planar frame 126' to produce a non-planar filter support structure.

Figure 11:
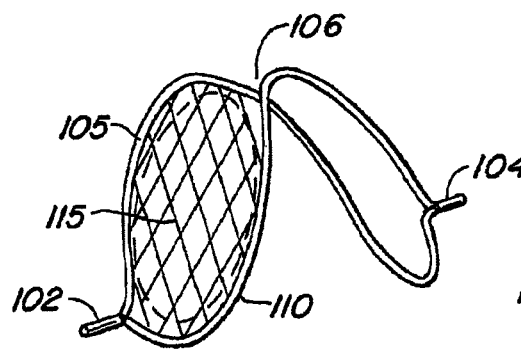
Figure 12A:
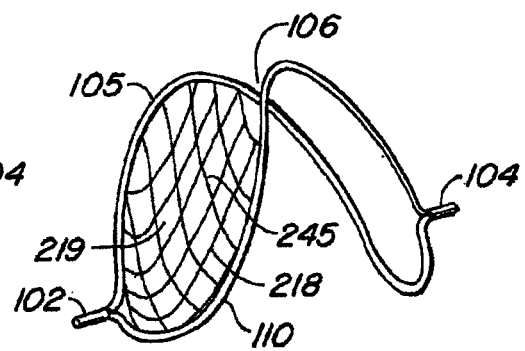
Figure 12B:
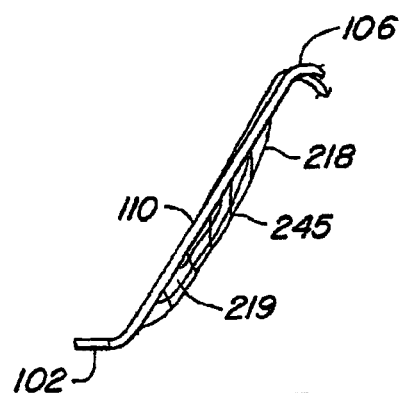

FIG. 11 illustrates a material capture structure 115 that remains in a generally planar arrangement between opposing portions of the support members 105, 110. In addition to FIG. 10B above, other alternative non-planar capture structures are possible even if the support frame is generally planar. FIG. 12A is a perspective view of a non-planar capture structure 245 within a generally planar support frame formed by support members 105, 110. Capture structure 245 is formed by intersecting strands, fibers, filaments or other suitable elongate material 218 to form filter cells 219. The capture structure 245 is slightly larger than the support frame dimensions resulting in a filter structure that is deformed out of the plane formed by the support structure as illustrated in FIG. 12B.

The material capture structure 115 may be in any of a number of different positions and orientations. FIG. 13A illustrates an embodiment of a filter of the present invention having two open loop support frames formed by support members 105, 110. Flow within the lumen 10 is indicated by the arrow. In this embodiment, the material capture structure 115 is placed in the upstream open loop support structure. In contrast, the material capture structure may be positioned in the downstream open loop support structure (FIG. 13B). In another alternative configuration, both the upstream and the downstream support frames contain material capture structures 115. FIG. 13C also illustrates an embodiment where a material capture structure is placed in every support loop in the device.

There are filter device embodiments having equal numbers of support frames with capture structures as support frames without capture structures (e.g., FIGS. 13A and 13B). There are other embodiments having more support frames without capture structures than there are support frames with capture structures. FIG. 14 illustrates a filter embodiment 190 having more support frames without capture structures than support frames with captures structures. The filter device 190 has two support members 105, 110 that are positioned adjacent to one another to form a plurality of support frames that are presented to the flow within the lumen 10. Alternatively, the plurality of support frames positioned to support a material capture structure across the flow axis of the device 190 or the lumen 10. The support members are joined together at end 192 and have two inflection points before being joined at end 194. The support members 105, 110 cross over one another at crossovers 106 and 196. The support frame 191 is between end 192 and crossover 106. The support frame 193 is between the crossovers 106, 196. The support frame 195 is between the cross over 196 and the end 194.

In addition, the filter device 190 has a retrieval feature 140 on each end. The retrieval feature 140 has a curved section 141 ending with a ball 142. The retrieval feature 140 rises up above the lumen wall placing the ball 142 and all or a portion of the curved section 141 into the lumen flow path to simplify the process of snaring the device 190 for retrieval or repositioning. Having a retrieval feature on each end of the device allows the device 190 to be recovered from the upstream or downstream approach to the device in the lumen 10. Various aspects of retrieval feature embodiments of the present invention are described in greater detail below.

Figure 14A:
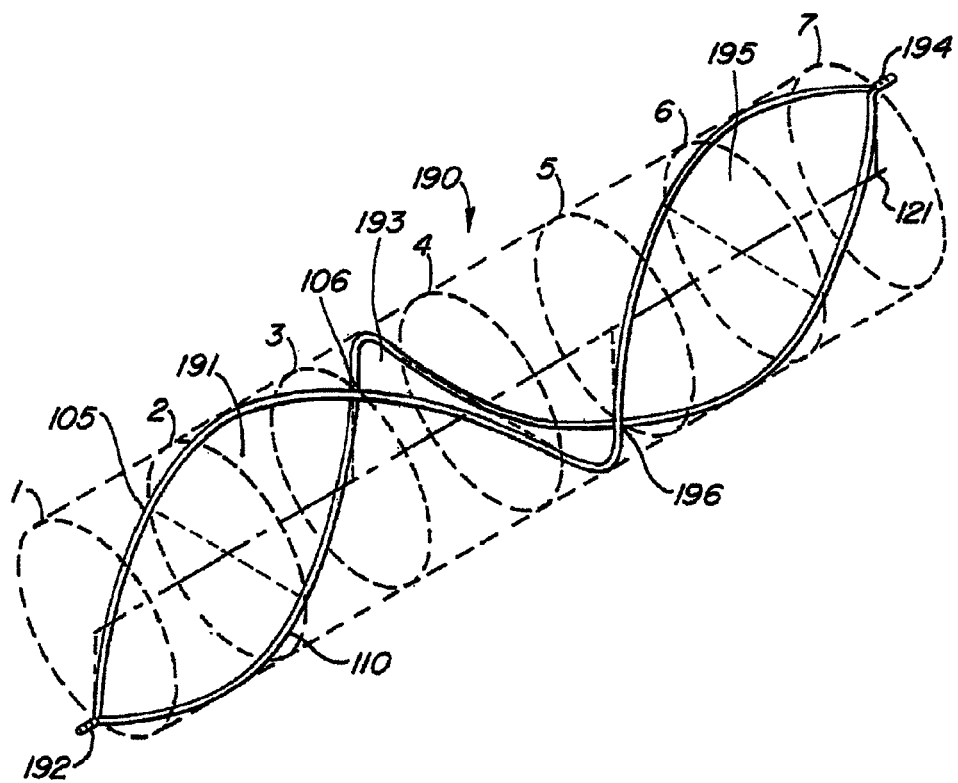
FIGS. 14-14C illustrate various aspects of a filtering device having three support frames.
Figure 14B:
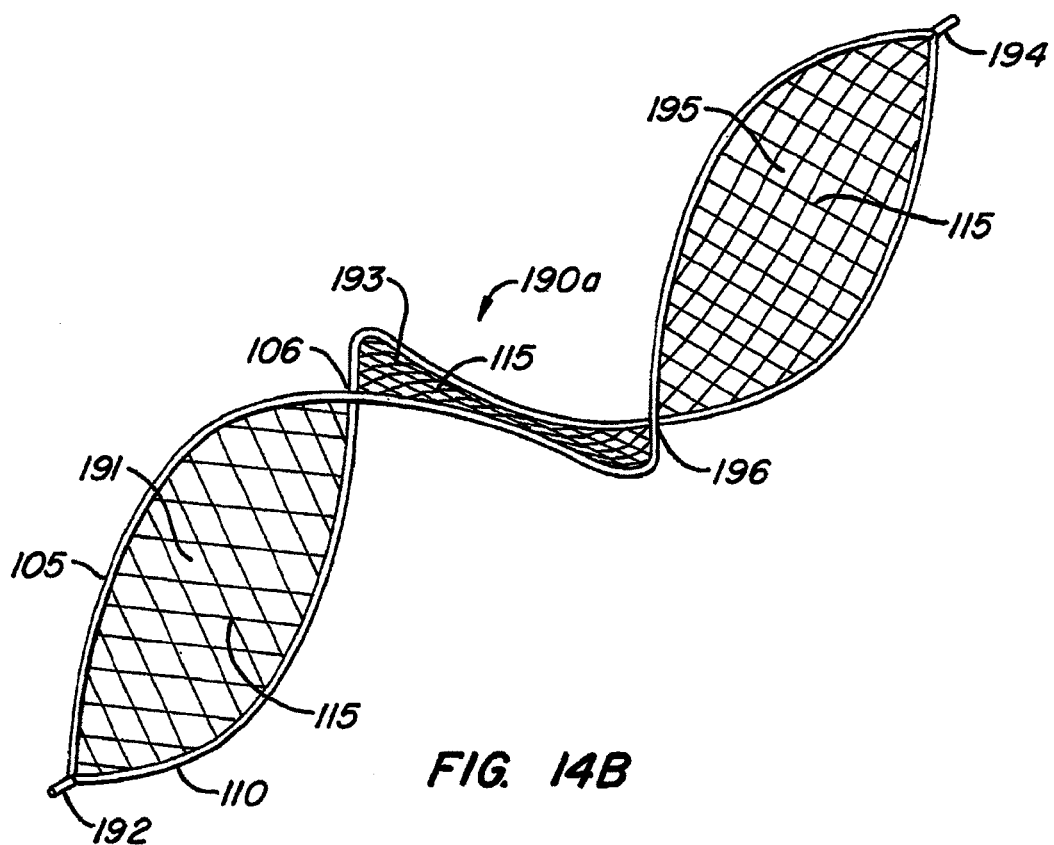

FIG. 14A illustrates the filter 190 imposed on a phantom cylinder having 7 sections. The retrieval features 140 have been omitted for clarity. The first support member 105 extends clock wise from end 192 about and along the axis of the device 121. The first support member 105 crosses section 2 at the 9 o'clock position, section 3 and the crossover 106 at the 12 o'clock position, section 4 at the 3 o'clock position, section 5 and the crossover 196 at the 6 o'clock position, section 6 at the 9 o'clock position and section 7 and the end 194 at the 12 o'clock position. The second support member 110 crosses section 2 at the 3 o'clock position, section 3 and the crossover 106 at the 12 o'clock position, section 4 at the 9 o'clock position, section 5 and the crossover 196 at the 6 o'clock position, section 6 at the 3 o'clock position and section 7 and the end 194 at the 12 o'clock position. FIG. 14B illustrates an alternative device embodiment 190a that is similar to the device 190 except that all support frames formed by the elongate members is used to support a material capture structure. In the illustrated embodiment, frames 191, 193 and 195 each support at material capture structure 115.

Figure 14C:
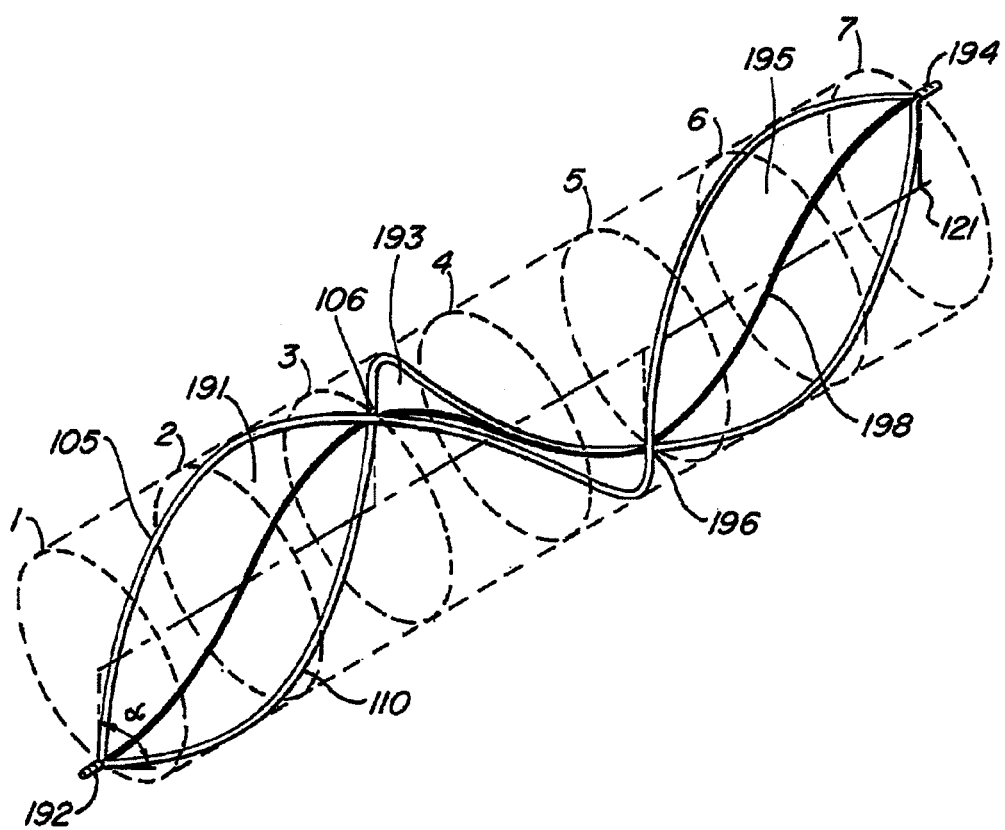

FIG. 14C illustrates an alternative configuration of filter 190. The filter device 190b is similar to device 190 and 190a and includes an additional support member 198 extending along the support member 105. In one embodiment, the additional support member 198 extends along the device axis 121, is positioned between the first and the second support members 105, 110 and is attached to the first end 192 and the second end 194. In the illustrative embodiment, the third support member 198 begins at end 192 and the 6 o'clock position in section 1, crosses section 3 and the crossover 106 at the 12 o'clock position, crosses section 5 and the crossover 196 at the 6 o'clock position, and ends at the 12 o'clock position in section 7 at the end 194.

Figure 15:
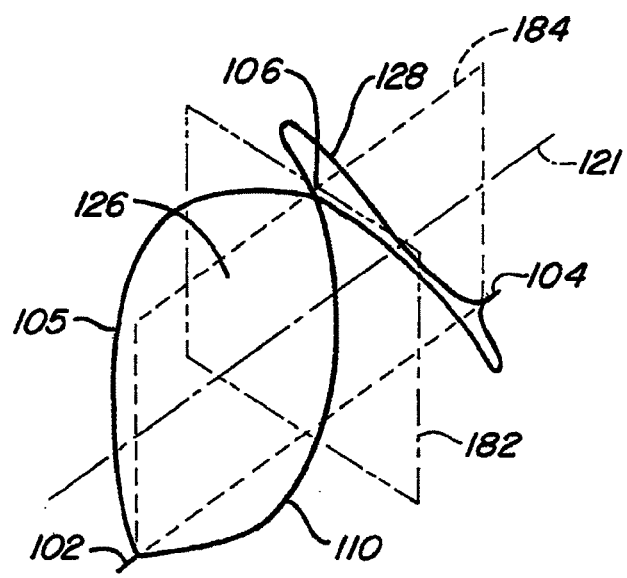
FIG. 15 illustrates planes of symmetry for filtering devices.

FIG. 15 illustrates the planes of symmetry found in some filter device embodiments of the present invention. The filtering structure that would be supported by one or both of the support frames is omitted for clarity. In one aspect, FIG. 15 illustrates an embodiment of an endoluminal filter of the present invention having a support structure that is generally symmetrical about a plane 182 that is orthogonal to the flow direction of the filter or filter axis 121 and contains a crossover point 106 between two structural elements of the support structure 105, 110. In another aspect, FIG. 15 illustrates an embodiment of an endoluminal filter of the present invention having a support structure that is generally symmetrical about a plane 184 that is parallel to the flow direction of the filter (i.e., axis 121) and contains both ends of the support structure 102, 104. It is to be appreciated that some filter device embodiments of the present invention may have either or both of the above described symmetrical attributes. It is to be appreciated that the above described symmetrical attributes are also applicable to the construction of embodiments of the material capture structures alone or as installed in a filter.

Figure 16A:
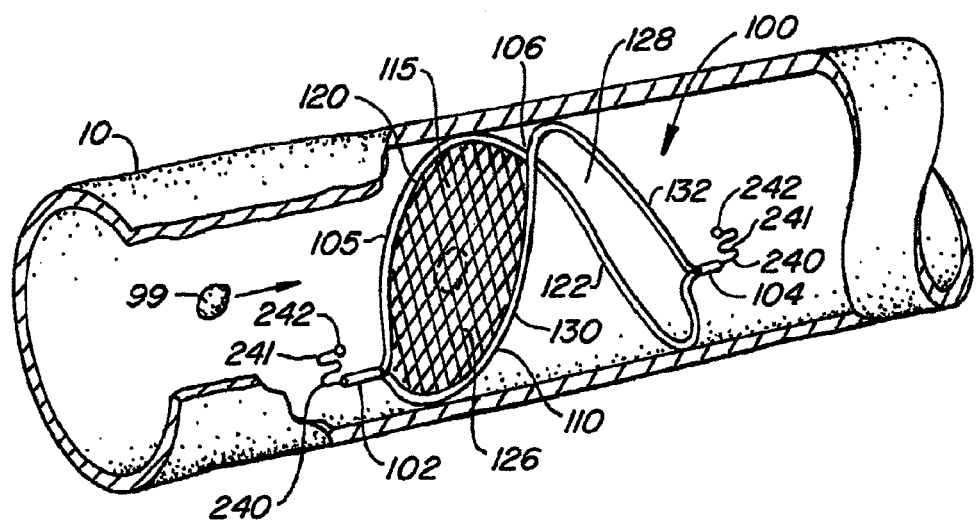
FIGS. 16A and 16B illustrate the response of a filtering device when contacted by debris flowing in a lumen.
Figure 16B:
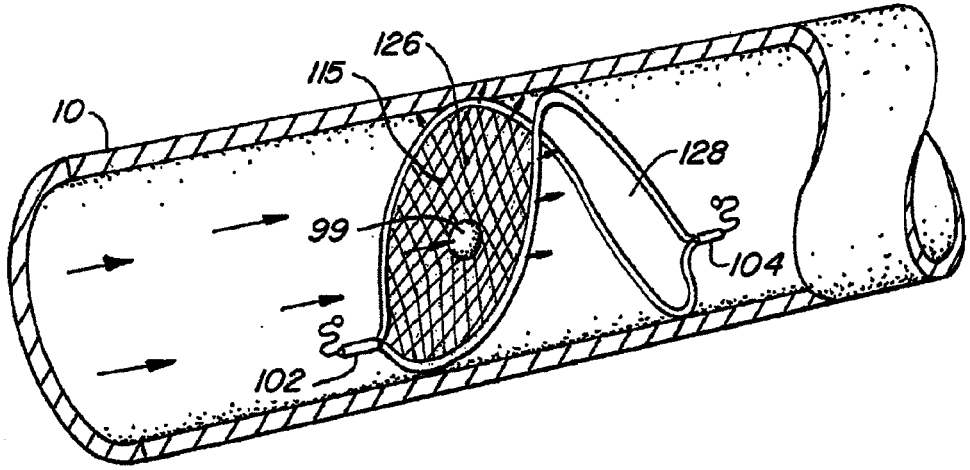

FIGS. 16A and 16B illustrate the response of a filter device 200 in response to a piece of clot material 99 contacting the material capture structure 115. The direction of flow and movement of the clot material 99 within lumen 10 is indicated by the arrows. The filter device 200 is similar to the embodiments described above with regard to FIGS. 6A-7G with the addition of the retrieval features 240 added to the ends 102, 104. The retrieval feature 240 has a curved section with multiple curves 141 that terminate with an atraumatic end 242. The multiple curves 141 are advantageously configured to collapse about a retrieval device (i.e, a snare in FIGS. 71A, 71B) to facilitate device 100 capture during retrieval. In this illustrative embodiment the multiple curves are generally shaped like a sinusoid and the end 242 is shaped like a ball or a rounded tip.

It is believed that upon embolic entrapment, the force fluid flow acting on clot material 99 is transmitted from the capture structure 115 to support frame 126 securing the capture structure 115. The force acting on the support frame 126 and in turn the support members 105, 110 urges the end 104 into the lumen wall. This action effectively fixes the second support frame 128. The force acting on the support frame 126 causes the angle β associated with the support frame 126 to increase the support frame 126 wedges further into the lumen wall.

Figure 17:
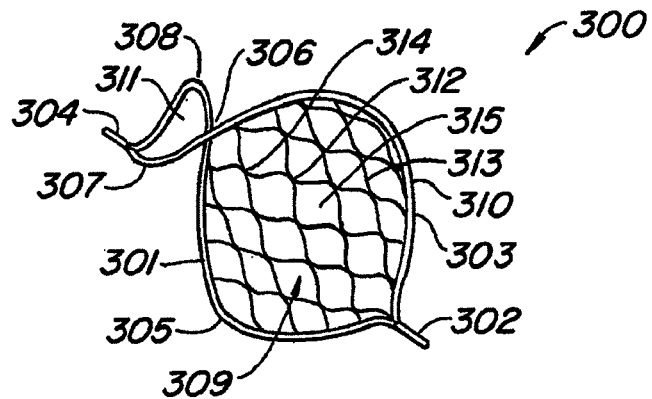
FIGS. 17-19 illustrate alternative filtering device aspects having different sized support frames and structural member lengths.
Figure 18:
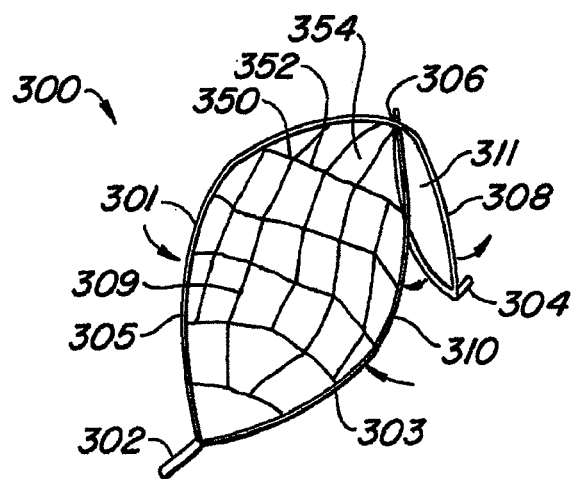
Figure 19:
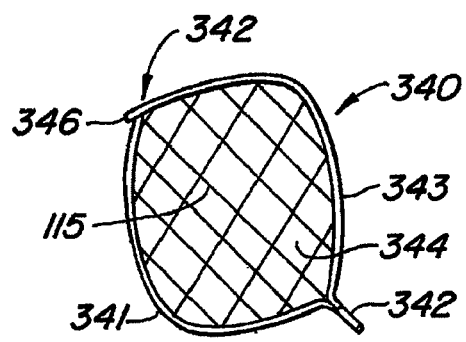

FIGS. 17, 18, and 19 illustrate various alternative filter device embodiments with support structures of different size and that may not be in contact with the lumen wall. FIG. 17 illustrates a perspective view of a filter device 300 according to one embodiment of the present invention. In this embodiment, elongate members 305, 310 are joined at ends 302, 304, to form frame 309 from end 302, sections 301, 303 and crossover 306 and frame 311 from end 304, sections 307, 308 and cross over 306. The frame 309 supports another embodiment of a material capture according to the present invention. The illustrated material capture structure 312 includes a plurality of strands 313 joined 314 to form a plurality of filter cells 315. The strands 313 may be joined using processes described below (e.g., FIG. 53A-53D) or may be formed by extruding the desired shape and size filter cell 315 from a material (e.g., FIG. 56).

FIG. 17 illustrates a so-called capacitor design because the elongate members that form frame 311 are configured to expand and contract the size and shape of frame 311 in response to changes in frame 309. This design feature allows an embodiment of the present invention to accommodate a large range of sizing and diameter changes. FIG. 18 illustrates an embodiment of the filter device 300 having a capture structure 350 having filter cells 354 formed by intersecting strands 352. FIG. 18 illustrates how inward movement of the frame 309 (indicated by the arrows) is corresponds to outward movement (indicated by the arrows) in the frame 308.

FIG. 19 illustrates an alternative filter device embodiment where the second frame is not closed. The filter device 340 includes support members 341, 343 that form a rounded support frame 344 to support the material capture device 115. The support members 341, 343 extend some distance beyond the cross over 342 but are not joined to form another end. A portion 346 of the support member 343 is shown extending beyond the cross over 342. The support members 341, 343 may extend for some distance along the device axis after the cross over 342 and may follow the same or a different shape as the shape of the support members in frame 309. The support members may extend along the device axis similar to earlier described two loop embodiments but stop short of being joined at a second end (e.g., FIG. 87).

Figure 20:
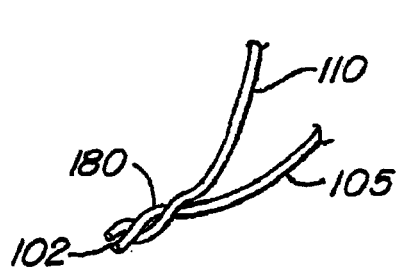
FIGS. 20-24 illustrate various alternative filtering device ends and structural member joining techniques.
Figure 21:
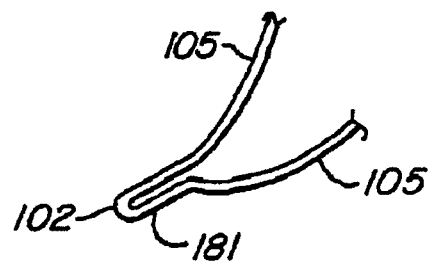
Figure 22:
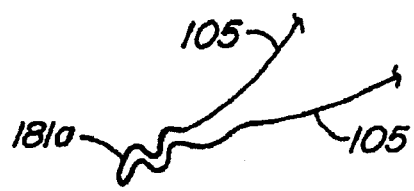
Figure 23:
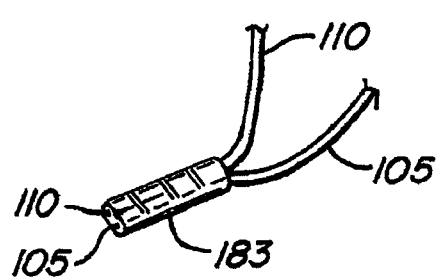
Figure 24:
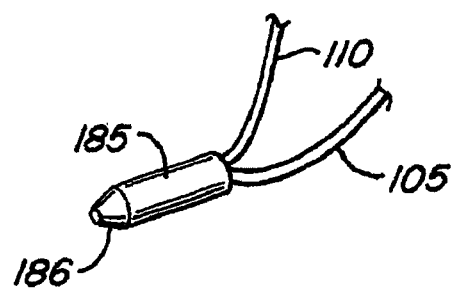

The ends of the filter devices of the present invention may be formed in a number of ways. A portion of the support structures 105, 110 may be wound 180 around one another (FIG. 20). In the illustrated embodiment, the wound portion 180 is used to form the end 102. In another alternative, the filtering device is formed from a single support member 105 that loops back on itself. In the illustrative embodiment of FIG. 21, support member 105 is formed into loop 181 to form the end 102. In an alternative to loop 181, the loop may contain a plurality of undulations (i.e., loop 181a in FIG. 22) or be formed into the shape of a retrieval feature or other component of the filter device. In yet another alternative, a cover is used to clamp, to join or otherwise bond the structural members together. In the illustrative example of FIG. 23, a generally cylindrical cover 183 is used to join together members 105, 110. The cover 183 may use any conventional joining method to secure the support members together such as adhesive, welding, crimping and the like. An alternative tapered cover 185 is illustrated in the embodiment of FIG. 24. The tapered cover 185 has a cylindrical shape and a tapered end 186. The tapered end 186 around the end having the tapered cover 185 and facilitates deployment and retrieval of the device. In one embodiment, the cover 185 is made of the same material as the structural member and/or the retrieval feature.

Some filter device embodiments of the present invention may include one or more retrieval features to assist recapturing and partially or fully recovering a deployed filter device. Retrieval features may be placed in any of a number of positions on the device depending upon the specific filter device design. In one embodiment, the retrieval device is positioned not only for ease of device recovery but also attached to the device in such a way that pulling on the retrieval device actually facilities removal of the device. In one embodiment, pulling on the retrieval device pulls the structural members away from the lumen wall. These and other aspects of the cooperative operation of the retrieval features during deployment and recapture will be described below with regard to FIGS. 72A-73D.

Figure 25:
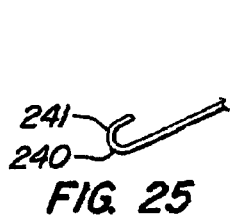
FIGS. 25-27C illustrate various alternative retrieval features.
Figure 26:
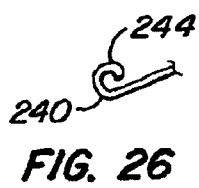
Figure 27A:
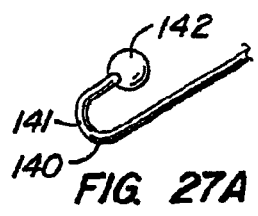
Figure 27B:
Figure 27C:
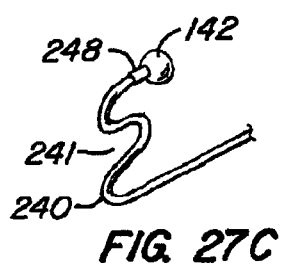

Several alternative embodiments of retrieval devices of the present invention are illustrated in FIGS. 25-27C. FIG. 25 illustrates a retrieval device 240 with a simple curve 241 formed in the end. FIG. 26 illustrates a retrieval device 240 with a curve 244 that is has a sharper radius of curvature than the curve 241 in FIG. 25. FIG. 27A illustrates a retrieval feature 140 having a curved section 141 with an atraumatic end 142. In the illustrative embodiment, the atraumatic end 142 is a ball than may be added to the end of curve 141 or formed on the end of the member used to form the feature 140. A ball 142 may be formed by exposing the end of the curved section 141 to a laser to melt the end into a ball. FIG. 27B illustrates a retrieval feature with a plurality of curved sections 241. In one embodiment, the curved sections 241 have a generally sinusoidal shape. In another embodiment, the curved sections 241 are configured to collapse when pulled on by a retrieval device like a snare (i.e., FIGS. 71A, 71B) FIG. 27C illustrates a retrieval feature 240 having a plurality of curved sections 241 and a ball 142 formed on the end. In additional embodiments, retrieval features of the present invention may include markers or other features to help increase the visibility or image quality of the filter device using medical imaging. In the illustrative embodiment of FIG. 27C, a radio opaque marker 248 is placed on the curved section 241. The marker 248 may be made from any suitable material such as platinum, tantalum or gold.

Figure 28A:
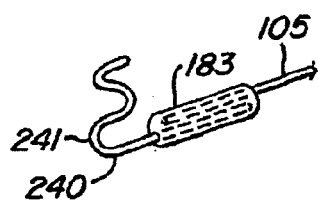
FIGS. 28A-28C illustrate various techniques of joining or forming retrieval features.
Figure 28B:
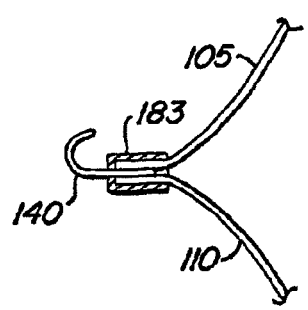
Figure 28C:
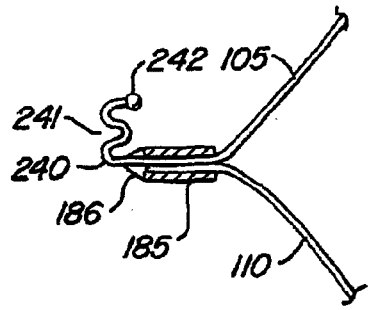

A cover placed about the ends may also be used to join a retrieval feature to an end or two support members. A cover 183 may be used to join a retrieval feature 240 to a support member 105 (FIG. 28A). In this illustrative embodiment, the support structure 105 and the retrieval feature 240 are separate pieces. A cover 183 may also be used to join together two members 110, 105 to a retrieval feature 140 (FIG. 28B). In another alternative embodiment, the retrieval feature is formed from a support member that is joined to the other support member. In the illustrative embodiment of FIG. 28C, the support member 105 extends through the tapered cover 185 and is used to form a retrieval feature 240. The tapered cover 185 is used to join the first support member and second support member 105, 110. In one alternative of the embodiment illustrated in FIG. 28C, the diameter of the support member 105 is greater than the diameter of the retrieval feature 240. In another embodiment, the diameter of the retrieval feature 240 is less than diameter of the support member 105 and is formed by processing the end of the support member down to a smaller diameter and is then shaped to form the retrieval feature 240. In another embodiment, the ball 242 or other atraumatic end is formed on the end of the retrieval feature.

Figure 29:
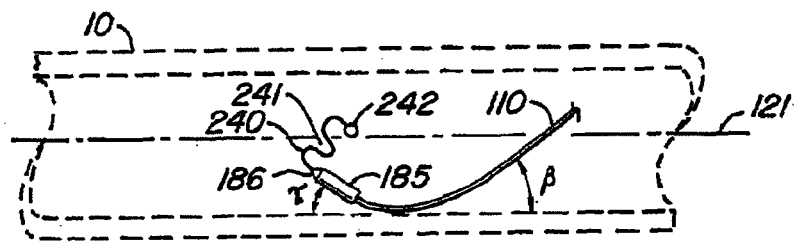
FIG. 29 illustrates a filtering device with a retrieval feature positioned within a lumen.

FIG. 29 illustrates a partial side view of a filter device in a lumen 10. This figure illustrates the retrieval feature angle τ formed by the retrieval feature and the interior lumen wall. The retrieval feature angle τ is useful in adjusting the height and orientation of the retrieval curves 241 and ball 242 within the lumen to improve the retrievability of the device. Generally, retrievably improves as the retrieval feature moves closer to the device axis 121 (i.e., central to the lumen axis as well). Additional curves may be added to the support members 110, 105 as needed to provide the desired range of retrieval feature angles. In one embodiment, τ ranges from −20 degrees to 90 degrees. In another embodiment, τ ranges from 0 degrees to 30 degrees.

Figure 30:
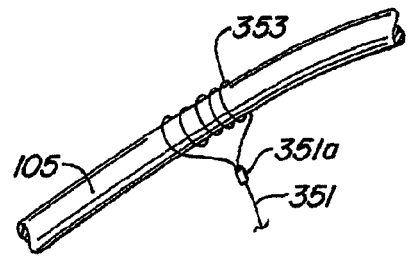
FIGS. 30-53D illustrate several alternatives techniques for joining material capture structures to support frames and forming filtering structures.
Figure 31:
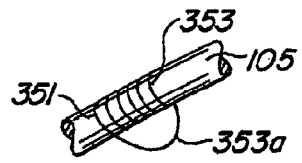
Figure 32:
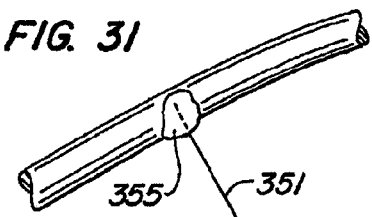
Figure 34A:
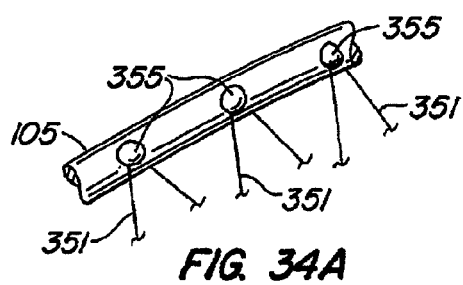
Figure 36:
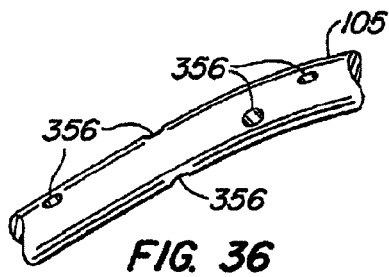

Attachment of Material Capture and Other Filtering Structures to Support Structures A number of different techniques may be used to attach material capture structures to support members. For clarity, the material capture structure has been omitted from the illustrations that follow but would be suitably secured using the line 351 or a loop. In FIG. 30 illustrates a line 351 with a number of turns 353 about a support member 105. The line 351 is secured back onto itself using a clip 351a. FIG. 31 illustrates a line 351 with a number of turns 353 about the support member 105 to secure a loop 353a that may be used to tie off or otherwise secure a material capture structure. A line 351 may also be glued 355 to a support 105 (FIG. 32). In another alternative embodiment, holes 356 formed in the support member are used to secure one or more lines 351 that are used in turn to secure a material capture structure. In an alternative to the linear arrangement of holes 356, FIG. 36 illustrates how holes 356 may be provided in a number of different orientations to assist in securing a material capture to the support structure 105. Alternatively, the line 351 may be glued 355 into the hole 356 (FIG. 34A and in section view 34B).

Figure 34C:
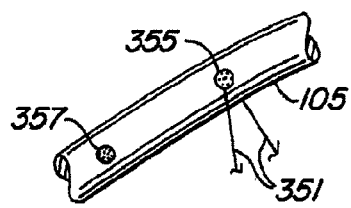
Figure 34B:
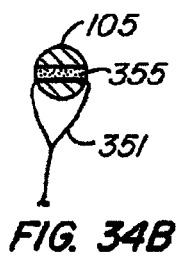
Figure 35:
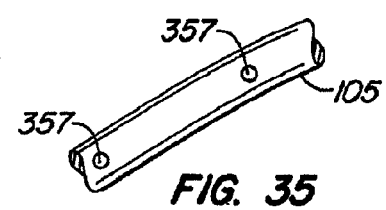
Figure 37:
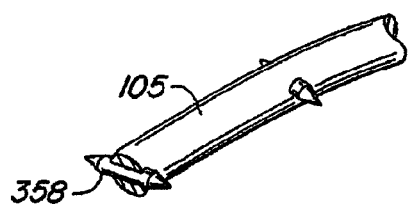

In other alternative embodiments, the holes 356 are used to secure lines 351 as well as provide a cavity for another material to be incorporated into the support structure 105. Other materials that may be incorporated into the support structure 105 include, for example, a pharmacological agent or a radio opaque material. The use of a radio opaque marker may be useful, for example, when the support structure is formed from a material with low imaging visibility such as, for example, shape memory polymers or biodegradable polymers. FIG. 34C illustrates an embodiment where one hole 356 is used to secure a line 351 and the other is filled with material or compound 357. In another alternative, some or all of the holes 356 may be filled with another material as in FIG. 35. In yet another alternative, the holes 356 are filled with small barbs 358 that may be used to secure the device to the lumen wall. The illustrative embodiment of FIG. 37 the barbs 358 are only long enough to break the surface of the lumen interior wall and not pierce through the lumen wall. While each of the above has been described with regard to the support member 105, it is to be appreciated that these same techniques could be applied to the support member 110 or other structure used to support a material capture structure.

Figure 38A:
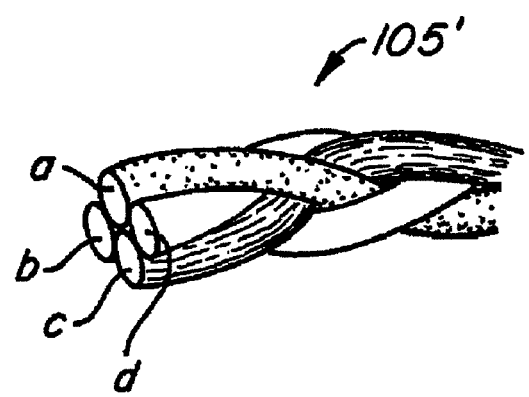
Figure 38B:
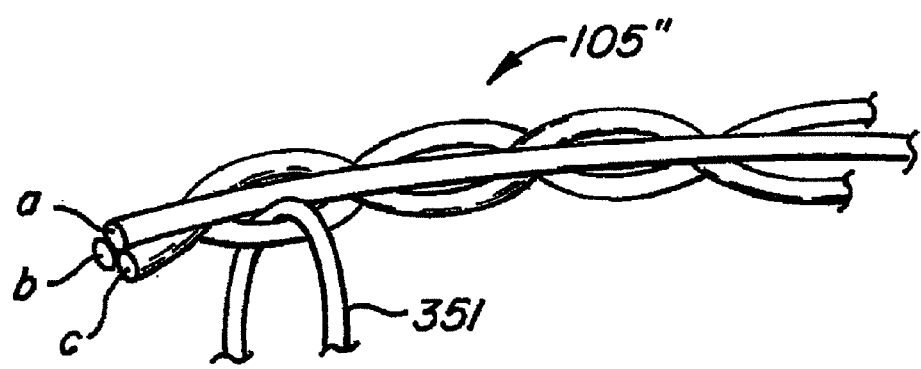

It is to be appreciated that the support structure embodiments are not limited to single member constructions. FIG. 38A illustrates an alternative braided support member 105'. Braided support structure 105' is formed by 4 strands a, b, c, and d. FIG. 38B illustrates another alternative braided support member 105". Braided support structure 105" is formed by 3 strands a, b, and c. FIG. 38B also illustrates how the braid structure may be used to secure a line 351. As can be seen in this embodiment, by using the line 351a material capture structure (not shown) is secured to at least one strand within the braided structure 105".

Figure 39:
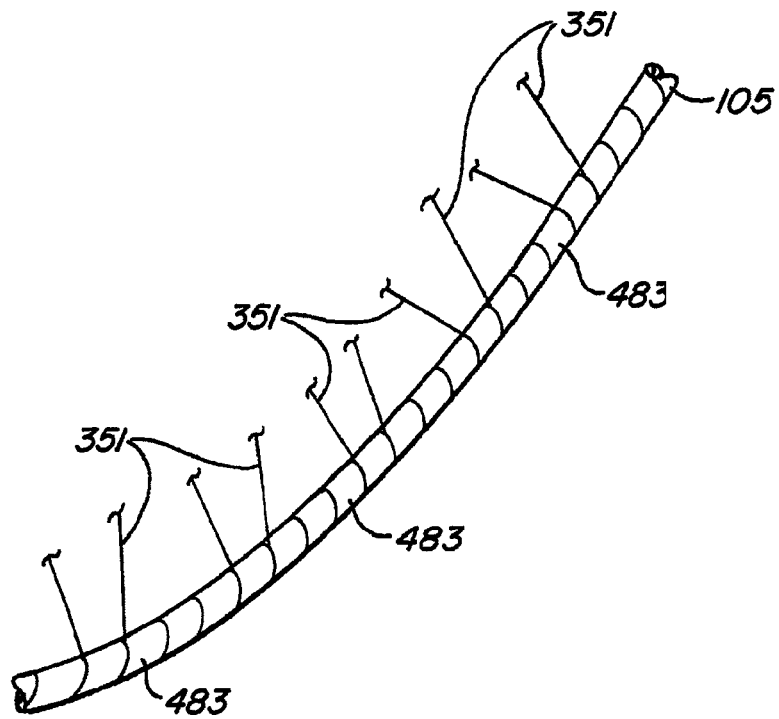
Figure 40:
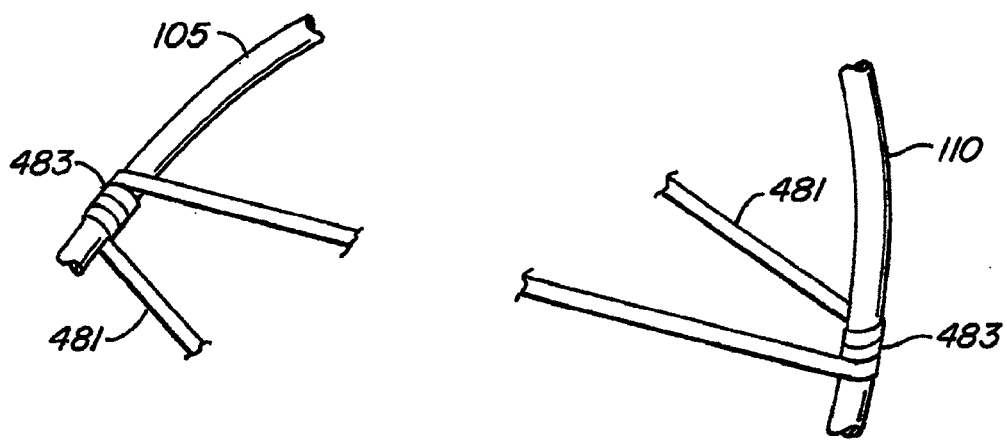

FIGS. 39 and 40 illustrate additional alternative techniques to secure a filter support structure to a support member. As illustrated in FIG. 39, there is illustrated a technique to secure a material capture structure securing line 351 to a support frame 105 using a material 481 wrapped around the support frame 105. In this manner, the material capture structure (not shown but attached to the lines 351) is attached to a material 481 that at least partially covers the first support structure 105. The lines 351 are passed between the material 481 and the support structure 105 as the material 481 as wraps 483 are formed along the support structure 105. The lines 351 are omitted in the embodiment illustrated in FIG. 40 as the material 481 forms wraps 483 and is used to secure the material capture structure (not shown). In one embodiment, the material 481 forms a tissue ingrowth minimizing coating over at least a portion of support structure. Alternatively, the filtering structure (not shown) is attached to the support structure 105 using a tissue ingrowth minimizing coating 481.

Figure 41:
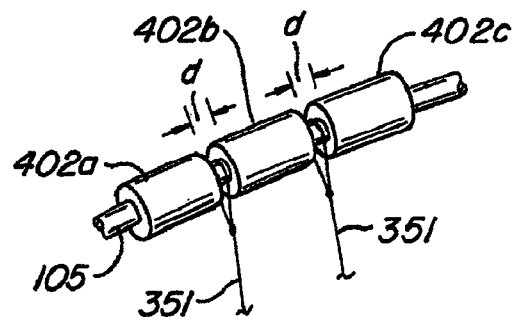
Figure 42:
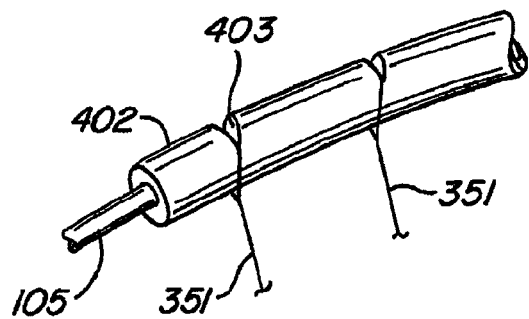
Figure 43:
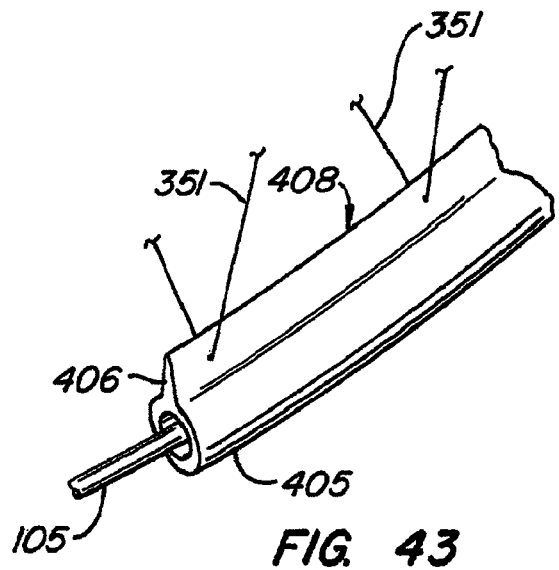

FIGS. 41, 42 and 43 relate to securing the material capture structure to a lumen disposed around the support member. FIG. 41 illustrates a lumen 402 that has been cut into segments 402a, 402b, 402c that are spaced by a distance "d." Lines 351 are attached around the support member and in the space "d" between adjacent segments. The segments may remain apart or be pushed together to reduce or eliminated the spacing "d." In contrast the segments in FIG. 41, the lumen 402 in FIG. 42 provides notches 403 for securing line 351. FIG. 43 illustrates a lumen 405 having a tissue growth inhibiting feature 408 extending away from the support member 105. As seen in section view 406 the inhibiting feature 408 has a different cross section shape than the support member 105. In addition, in some embodiments, the lumen 405 is selected from a suitable tissue ingrowth minimizing material so that is acts like a tissue ingrowth minimizing coating on the support structure. In other embodiments, the cross section shape 406 is configured to inhibit tissue growth over the tissue ingrowth minimizing coating.

Figure 44:
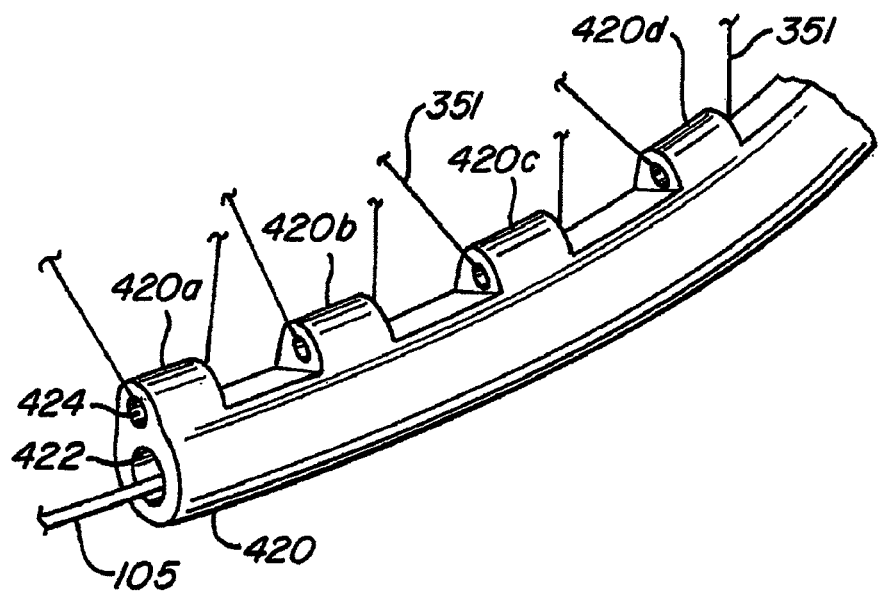
Figure 45:
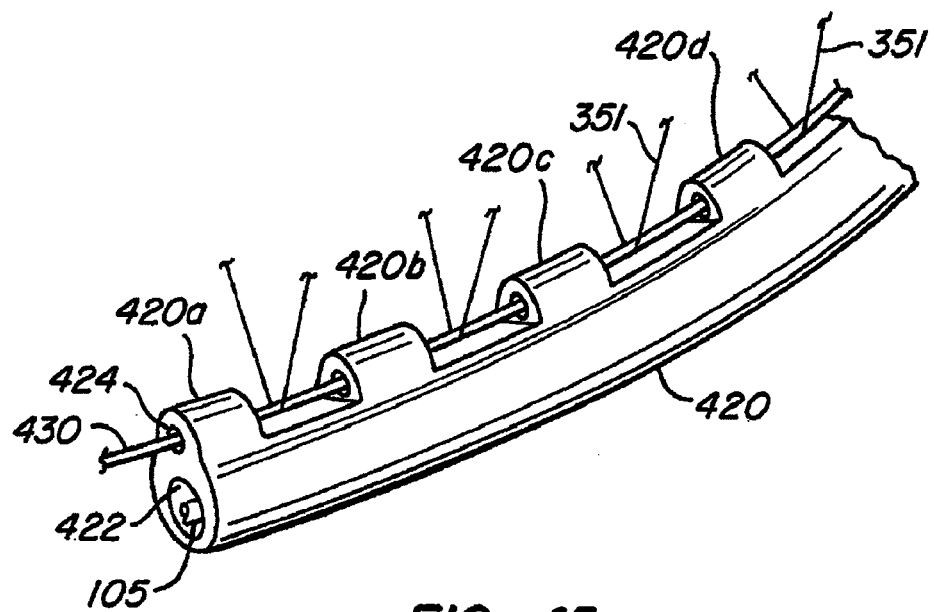

FIGS. 44 and 45 illustrate filter device embodiments utilizing dual lumen structures. The dual lumen structure 420 includes a lumen 422 and a lumen 424 and has a generally teardrop shaped cross section area. In this illustrative embodiment, the support structure 105 is disposed in the lumen 422 and the second lumen 424 is used to hold lines 351 and secure a material capture device (not shown). In the illustrative embodiment, the lumen structure 420 has been cut to form a number of segments 420*a, b, c* and *d* in the lumen 424. The connection rings formed by the segments 420*a-d* are used to secure lines 351 as needed. FIG. 45 illustrates an alternative configuration for the lumen structure 420. In this alternative configuration, a release line 430 extends through the notched lumen 424. The lines 351 extend about the release line 430 and hence to secure the material capture structure (not shown). Since the lines 351 are connected using the release line, removal of the release line from lumen 424 will allow the material capture structure secured using the lines 351 to be released from the support structure and removed from the lumen. A configuration such as that shown in FIG. 45 provides a filtering structure that would be releasably attached to an open loop (i.e., an open loop frame formed by the support structure). The embodiment illustrated in FIG. 45 provides a release line 430 positioned along the open loop (formed by member 105) and a filtering structure (not shown) is attached to the open loop using the release line.

In another embodiment, a filter device of the present invention is configured to be a coated endoluminal filter. In addition to coating all or a portion of the support structures or filter elements of this device, the coating on the support members may also be used to secure a filtering structure to the support structure. In one embodiment, a coated endoluminal filter has a support structure, a filtering structure attached to the support structure and a coating over at least a portion of support structure. In one aspect, the coated support structure may form a rounded support frame, an open loop or other structure to support a filtering structure described herein. In one embodiment, the coating over at least a portion of support structure is used to secure a plurality of loops (i.e., flexible form or rigid form) to the support structure. The plurality of loops are then used to secure a filtering structure such as a material capture structure, for example, within the coated endoluminal filter. In one embodiment, the coating is a tissue ingrowth minimizing coating.

It is to be appreciated that a filtering structure may also be attached to the support structure using the tissue ingrowth minimizing coating. In some embodiments, the tissue ingrowth minimizing coating is wrapped around the support structure or, alternatively, it may take the form of a tube. If a tube is used, the tube may be a continuous tube or comprise a plurality of tube segments. The tube segments may be in contact or spaced apart. The tube may have the same or different cross section shape than the support member. In another embodiment, the tissue ingrowth minimizing coating is in the shape of a tube and the support structure is in the interior of the tube.

In some other embodiments, a bonding material is provided between the tissue ingrowth minimizing coating and the support structure. The bonding material may be wrapped around the support structure or may take the form of a tube. If a tube is used, the tube may be a continuous tube or comprise a plurality of tube segments. The tube segments may be in contact or spaced apart. The bonding material tube may have the same or different cross section shape than the support member or the coating about the bonding material. In one embodiment, the bonding material is in the shape of a tube with the support member extending through the bonding material tube lumen. In one embodiment, a plurality of loops (i.e., flexible form or rigid form) are secured to the support structure by sandwiching the line used to form the loops between a bonding material around the support member and a coating around the bonding material. In one embodiment, the bonding material has a lower reflow temperature than the coating around the boding material. In this embodiment, the line used to form the loops is secured at least in part by reflowing the bonding material to secure the line between the coating around the bonding material and the support structure. In another alternative, the coating around the bonding material is a shrink fit coating that also shrinks around the bonding structure and the support member during or after a process that reflows the bonding material. In any of the above alternatives, the plurality of loops may be used to secure a filtering structure such as a material capture structure, for example, within the coated endoluminal filter.

Some embodiments of the coated endoluminal filter include some or all of the other features described herein such as, for example, a retrieval feature on the support structure, a retrieval feature on each end of the support structure, a support structure having two elongate bodies that are joined together to form a rounded frame, and a support structure having two spiral shaped elongate bodies. In addition, some coated endoluminal filters have a support structure that is generally symmetrical about a plane that is orthogonal to the flow direction of the filter and contains a crossover point. In another alternative coated endoluminal filter embodiment, the support structure of the coated endoluminal filter is generally symmetrical about a plane that is parallel to the flow direction of the filter and contains both ends of the support structure.

Figure 46:
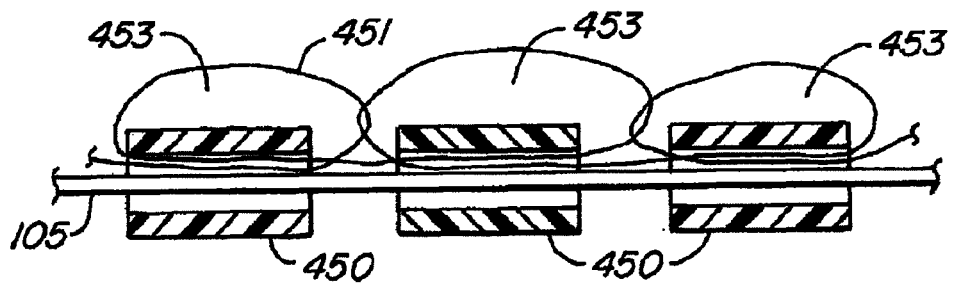
Figure 47:
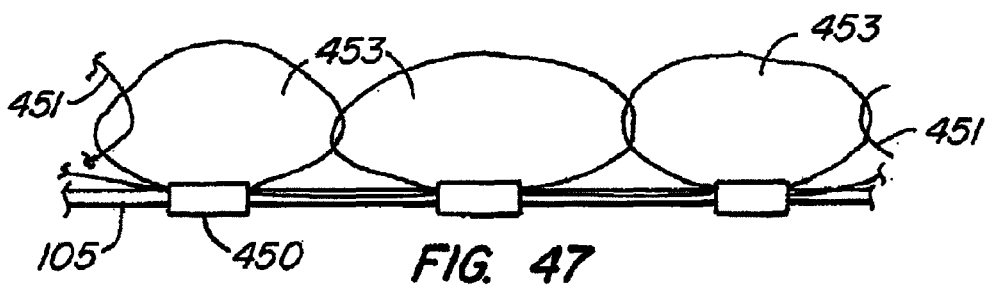

FIGS. 46-51B illustrate several aspects of coated endoluminal filter embodiments. These figures are not to scale and have exaggerated dimensions to make clear certain details. FIG. 46 illustrates a number of segments 450 of a coating placed about the support member 105. One or more lines 451 extend between the segment 450 and the support member 105 and form a plurality of loops 453. In one embodiment, the line 451 is a single continuous line. Once formed, the segments 450 undergo suitable processing to shrink the segment diameter around the line 451 and the support member 105 thereby securing the line 451 and loops 453 against the support structure (FIG. 47). The segment 450 is secured about the support member 105 as illustrated in the end view of FIG. 51A. The segments 450 in the embodiment shown in FIG. 47 are spaced apart. In other embodiments, the segments 450 may be in contact or have spacing different from that illustrated in FIG. 47. The sizes of the various components illustrated in FIGS. 46, 47 and 51A are exaggerated to show detail. The dimensions of one specific embodiment are: the support member 105 is a NiTi wire having an outside diameter of between 0.011" and 0.015"; the segments 450 are 0.2" long cut from a PTFE heat-shrink tubing having and a pre-shrunk outside diameter of 0.018" and a wall thickness of 0.002"; the line 451 is monofilament ePTFE of an outer diameter of 0.003" and the loops 453 have a nominal diameter of between about 0.1" to about 0.4".

Figure 48:
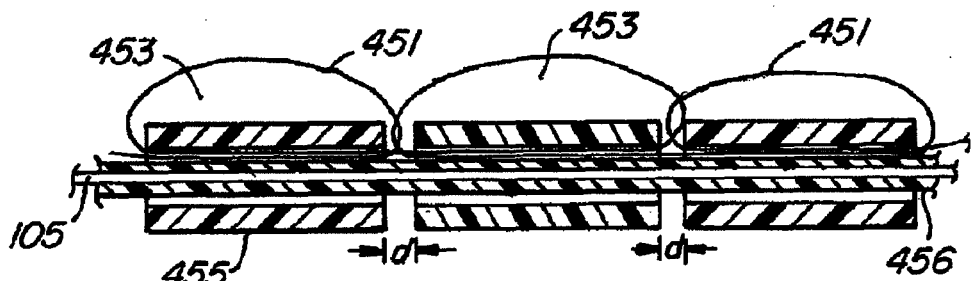
Figure 49:
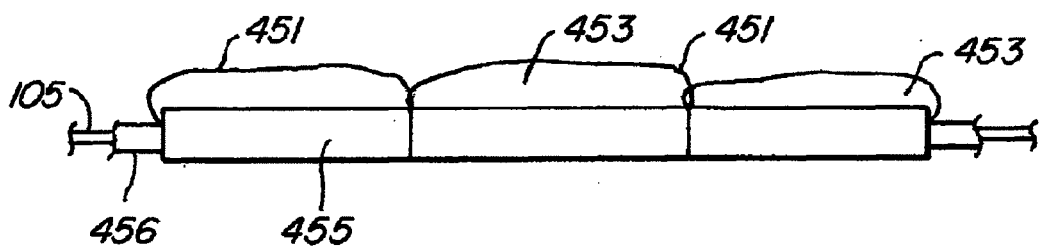
Figure 51A:
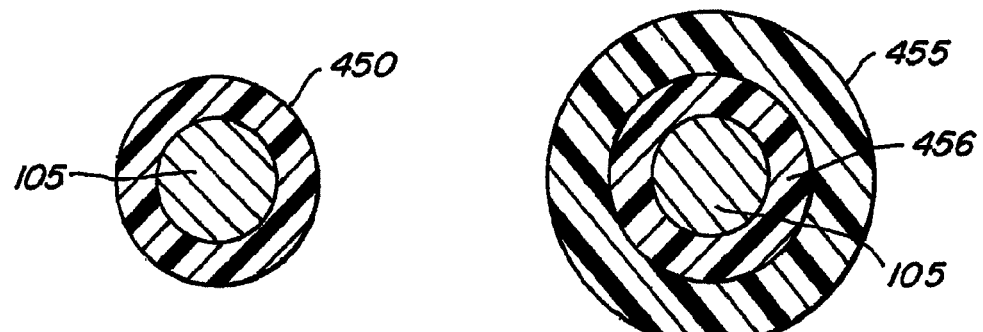
Figure 51B:
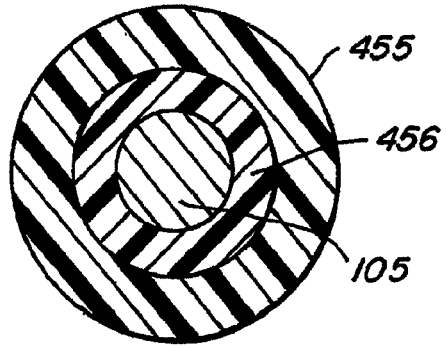

FIGS. 48, 49 and 51B illustrate a bonding material 456 about the support member 105 and a number of segments 455 about the bonding material 456. One or more lines 451 extend between the segments 455 and the bonding material 456 and form a plurality of loops 453. In one embodiment, the line 451 is a single continuous line. Once formed, bonding material 456 and/or the segments 450 undergo suitable processing to secure the line 451 between the bonding material 456 and the coating 455 thereby securing the line 451 and loops 453 against the support structure (FIG. 49). The coating segment 450 and the bonding material 456 is secured about the support member 105 as illustrated in the end view of FIG. 51B. The segments 455 in the embodiment shown in FIG. 48 are spaced apart by spacing "d." In other embodiments, the segments 455 may be in contact after processing (FIG. 49) or have spacing different from that illustrated in FIG. 48. In a preferred embodiment, the spacing between the segments 455 is removed by a portion of the boding material 456 flowing between and securing adjacent segments 455. The sizes of the various components illustrated in FIGS. 48, 49 and 51B are exaggerated to show detail. The dimensions of one specific embodiment are: the support member 105 is a NiTi wire having an outside diameter of between 0.011" and 0.015"; the segments 455 are 0.3" long cut from a PTFE heat-shrink tubing having a pre-shrunk outside diameter of 0.022" and a wall thickness of 0.002"; the bonding material is a tube of FEP heat shrink tubing having a pre-shrunk outside diameter of 0.018" and a wall thickness of 0.001"; line 451 is 0.002" outer diameter PET monofilament and the loops 453 have a nominal diameter of between about 0.1" to about 0.4". It is to be appreciated that the segments 450, 455 and bonding material 456 may be formed, for example, from: ePTFE, PTFe, PET, PVDF, PFA, FEP and other suitable polymers. Moreover, embodiments of strands, lines, fibers and filaments described herein may also be formed from ePTFE, PTFe, PET, PVDF, PFA, FEP and other suitable polymers.

Figure 50:
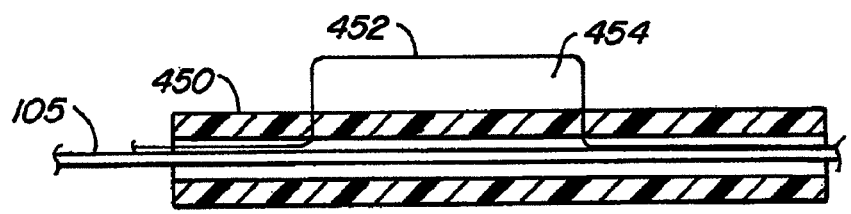

FIG. 50 illustrates the use of a continuous flexible line 452 passed through a continuous coating segment 450 forming loops 454. The loops 454 are disposed along the length of the coating 450 at regular intervals; the continuous coating segment 450 are uniform in length to the support members 105 using a PTFE heat shrink tubing having pre-shrunk diameter of 0.018" and a wall thickness of 0.002". The line 452 is monofilament ePTFE of an outer diameter of 0.003" and the loops 454 have a nominal diameter of between about 0.1" to about 0.4".

Figure 52A:
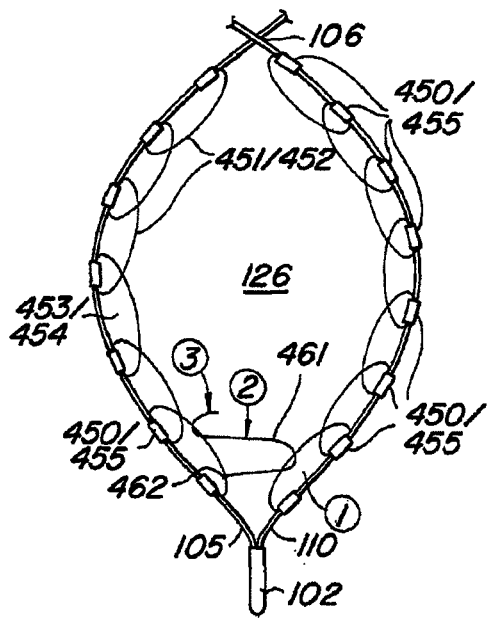
Figure 52B:
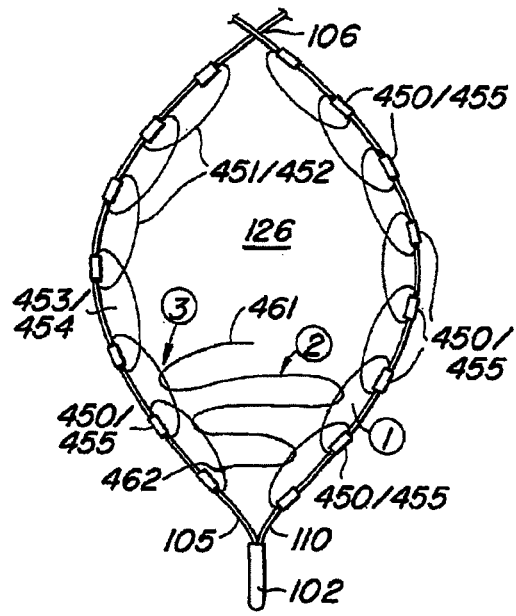
Figure 52C:
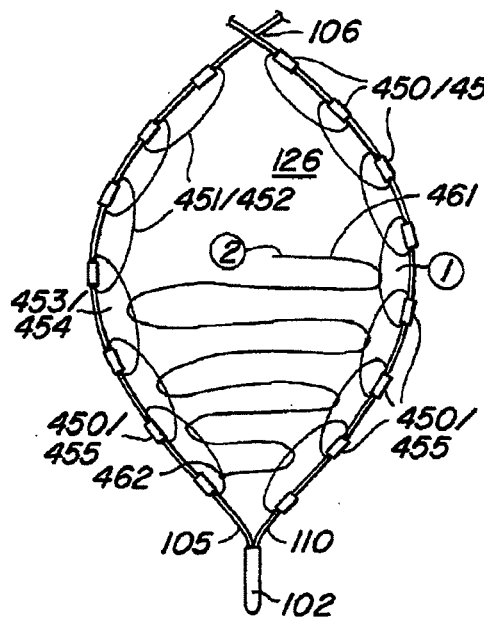
Figure 58:
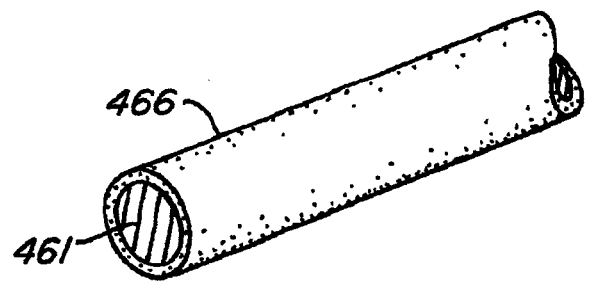

FIGS. 52A-53D illustrate alternative techniques for forming and/or attaching a filtering structure to a support structure. FIG. 52A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably attached 462 to a line 451/452 by tying, welding, gluing or by incorporating the filament 461 during the processing steps described with regard to FIGS. 46-51B. Next, the filament is traverses across the frame 126 and about the loops 453/454. In this embodiment, the lacing pattern between loops crosses a line extending between the end 102 and the crossover 106. The general pattern is that the filament extends across the frame 126 and around one right side loop (1) and back across the frame 126 (2) and around (3) a left side loop 453/454. The lacing process continues as shown in FIGS. 52B and 52C. When completed, the lacing process produces a filtering structure 465 from one or more filaments secured to loops 451/452 that are secured to the support members 105/110. The filament in the filtering structure 465 may be taut between the loops 451/452 or have some degree of sag (as illustrated in FIG. 52D). Filament 461 or other material used to form material capture structure may be coated with a pharmacological agent (coating 466 in FIG. 58). The pharmacological agent may be any of a wide variety of compounds, drugs and the like useful in the procedures performed using or the operation of various filtering device embodiments of the present invention. The pharmacological agent coating 466 may include pharmacological agents useful in preventing or reducing thrombus formation on the filtering structure, chemically lysing debris captured in the filtering structure and the like.

Figure 52D:
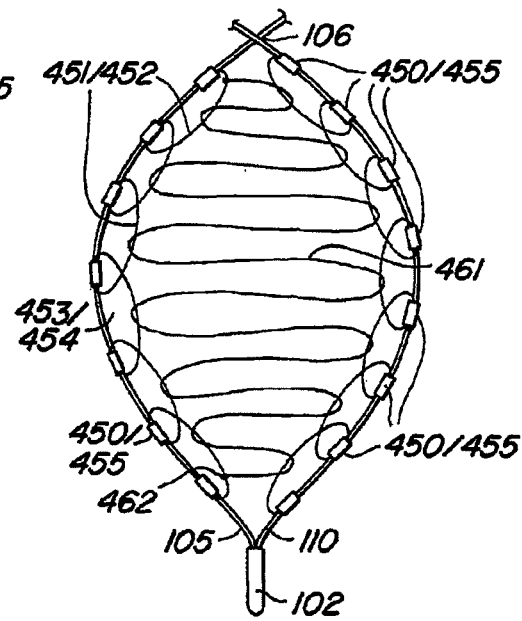
Figure 53A:
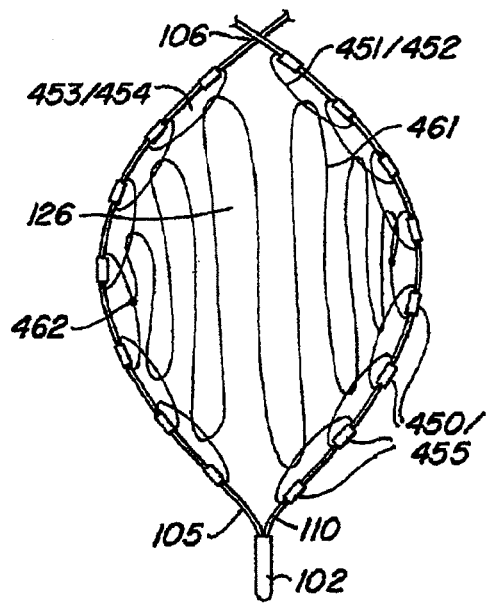
Figure 53B:
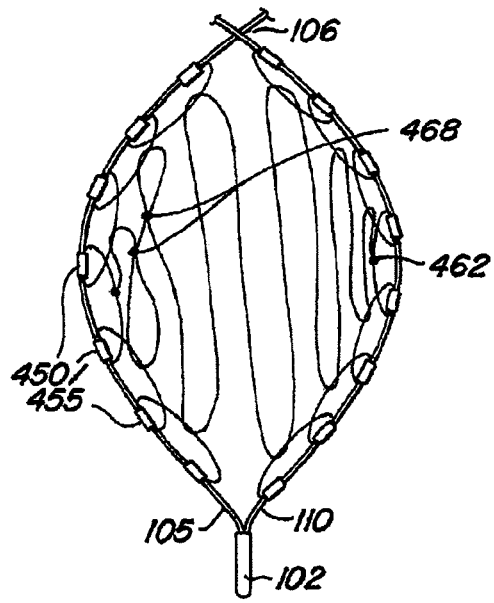
Figure 53C:
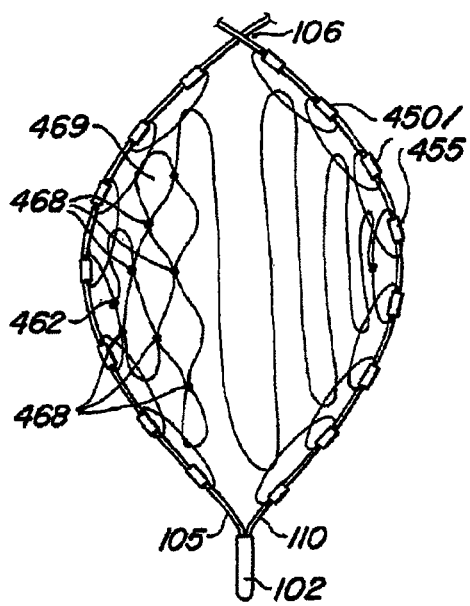
Figure 53D:
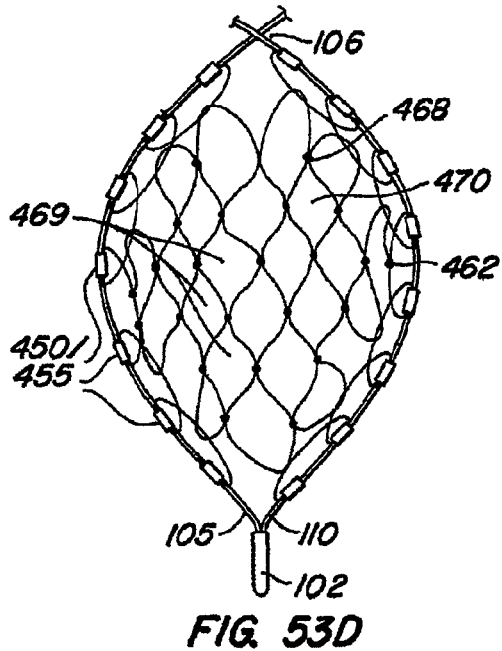

FIG. 53A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably joined 462 to a line 451/452 by tying, welding, gluing or by incorporating the filament 461 during the processing steps described with regard to FIGS. 46-51B. Next, the filament 461 was laced as described above with regard to FIG. 52A about the loops 453/454. In this embodiment, however, the lacing pattern between loops remains generally parallel to a line extending between the end 102 and the crossover 106. When completed, the lacing process produces a filtering structure from one or more filaments 461 that extend parallel to a line between the end 102 and crossover 106 and are secured to loops 451/452 secured to the support members 105/110. This filtering structure (FIG. 53A) may be used within a filter device of the present invention. In addition, the filtering structure in FIG. 53A (as well as the structure in FIG. 52D) may be further processed to join 468 adjacent filaments 461 to form filter cells 469 as part of a filtering structure 470. The process used to join 468 adjacent filaments 461 may include any conventional joining technique such as tying, welding, bonding, gluing, and the like. In addition, segments of tubing (i.e., segments 450, 455 456 described above) could be used to join 468 portions of adjacent filaments 461. In one specific embodiment, the filament 461 is ePTFE monofilament with an outer diameter of 0.003" joined 468 using a piece of FEP heat shrink tubing having a pre-shrunk outer diameter of 0.008" and a wall thickness of 0.001". The filtering structure 470 may be taut between the loops 451/452 or have some degree of sag (as illustrated in by the filtering structure in FIG. 52D). The filter cells 469 may be formed in numerous sizes and shapes as described in greater detail below.

Figure 57A:
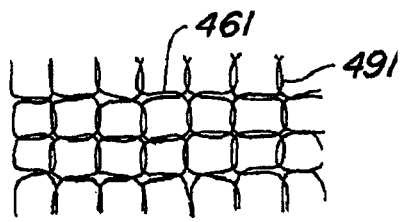

Alternatively, the filtering structures in FIG. 53A and FIG. 52D may incorporate additional loops 491 formed by looping the filament 461 as illustrated in FIG. 57A.

Alternative Filtering and/or Material Capture Structures

In some embodiments, the material capture structure contains a number of filter cells. Filter cells may be formed in a number of different ways and have a number of different shapes and sizes. The shape, size and number of filter cells in a specific filter may be selected based on the use of a particular filter. For example, a filter device of the present invention configured for distal protection may have a filter cell size on the order of tens to hundreds of microns to less than 5 millimeters formed by a selecting a filter material with a pore size (FIG. 63A, 63B) suited to the desired filtration level. In other applications, the filter cell may be formed by overlapping (i.e., joined or crossed without joining) filaments to form cells that will filter out debris in a lumen above a size of 2 mm. Various other filter sizes and filtration capacities are possible as described herein.

Figure 57B:
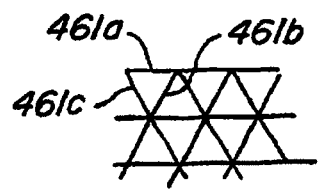

Intersecting filaments (FIG. 54C) may be used to form diamond shaped filter cells (FIG. 54A), as well as rectangular shaped filter cells (FIGS. 54B, 2A and 9B). Multiple strand patterns may also be used such as the three strand 461a, 461b and 461c array illustrated in FIG. 57B. Intersecting filaments may also be knotted, tied or otherwise joined 468 (FIGS. 55A and 55E). Intersecting filaments may form the same or different filter cell shapes such as, for example, an elongated oval in FIG. 55C, one or more joined diamonds as in FIG. 55B and an array of joined polygons as in FIG. 55D. Cells may also be formed using the techniques described above in FIGS. 52A-53D. In one embodiment, a filter cell is defined by at least three intersecting filaments 461. The filter element 461 may be formed from any of a wide variety of acceptable materials that are biocompatible and will filter debris. For example, filaments, lines and strands described herein may be in the form of a multifilament suture, a monofilament suture a ribbon, a polymer strand, a metallic strand or a composite strand. Additionally, filaments, lines and strands described herein may be formed from expanded polytetrafluoroethylene (ePTFE), polytetrafluoroethylene (PTFE), Poly(ethylene terephthalate) (PET), Polyvinylidene fluoride (PVDF), tetrafluoroethylene-co-hexafluoropropylene (FEP), or poly (fluoroalkoxy) (PFA), other suitable medical grade polymers, other biocompatible polymers and the like.

The joined polygons may have any of the shapes illustrated in FIGS. 60A-60F. It is to be appreciated that filter cells may have any, one or more, or hybrid combinations of shapes such as, for example, circular (FIG. 60A), polygonal (FIG. 60B), oval (FIG. 60C), triangular (FIG. 60D), trapezoidal or truncated conical (FIG. 60E).

Figure 56:
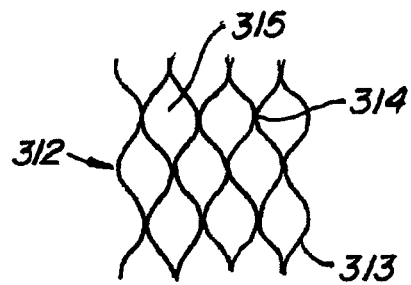

In addition, the material capture structure may have filter cells formed by extruding a material into a material capture structure. FIG. 56 illustrates an exemplary filtering structure 312 where a material is extruded into strands 313 that are joined 314 and spaced apart for form one of more filter cells 315. In one embodiment, the strands are extruded from Polypropylene material, forming diamond shaped filter cells approximately 4 mm in height and 3 mm in width.

Figure 59A:
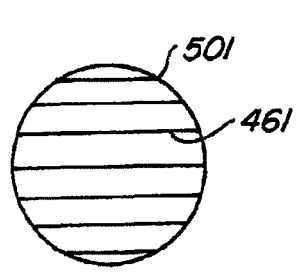
Figure 59B:
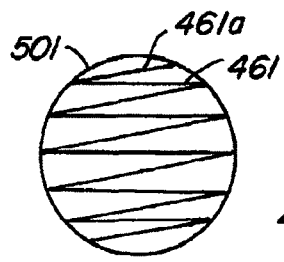
Figure 59C:
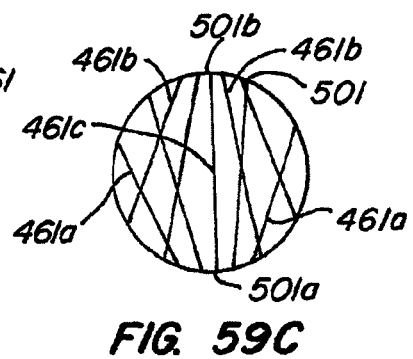
Figure 59D:
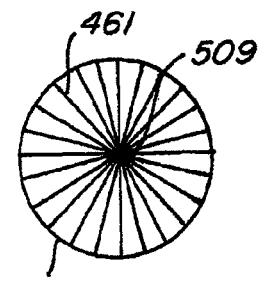
Figure 59E:
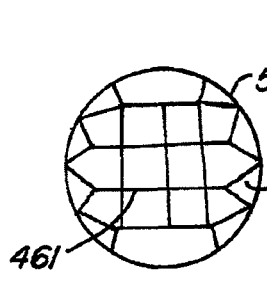

FIGS. 59A-63B illustrate several different filtering structure configurations. For simplicity of illustration, the filtering material is shown attached to a circular frame 501. It is to be appreciated that the circular frame 501 represents any of the various open loop, rounded frame or other support frames described herein. FIG. 59A illustrates a frame pattern similar to FIG. 52D. FIG. 59B adds an additional transverse filaments 461a at an angle to the filaments 461. FIG. 59C illustrates a plurality of filaments 461a extending up from the frame bottom 501a about a central filament 461c and a plurality of filaments 461b extending down from the frame top 501b about a central filament 461c. In this illustrative embodiment, the filaments 461a,b are arranged symmetrically about the central filament 461c. Other non-symmetrical configurations are possible. More than one central filament 461c may be used to form a variety of different size and shaped polygonal filter cells (e.g., FIG. 59E).

Figure 59F:
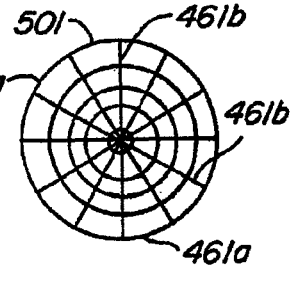
Figure 59G:
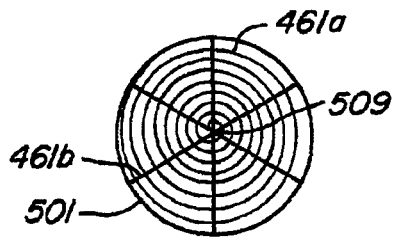

Filaments may also be arranged using a variety of radial patterns. Fr example, multiple filaments 461 may from a common point 509 out the edge of frame 501. In some embodiments, the common point is central to the frame 501 (FIG. 59D) and in other embodiments the common point 509 is in a different, non-central location. The sectors formed by the multiple filaments (FIG. 59D) may be further divided into multiple filter cell segments by winding a filament 461a about and across segment filaments 461b. In contrast to a single filament spirally out from the point 509 as in FIG. 59G, the segmented filter cells in FIG. 59F are formed by attaching single filament 461a to the segment filaments 461b.

Figure 61A:
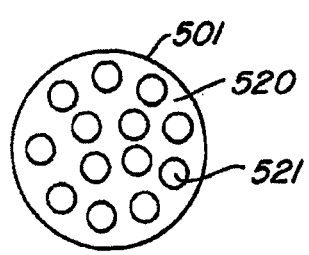
Figure 61B:
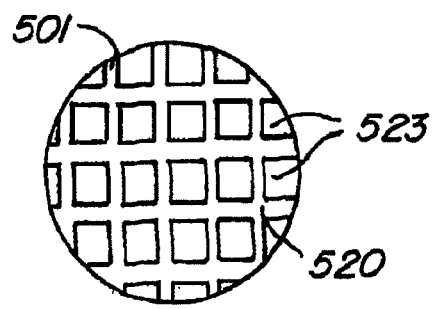
Figure 61C:
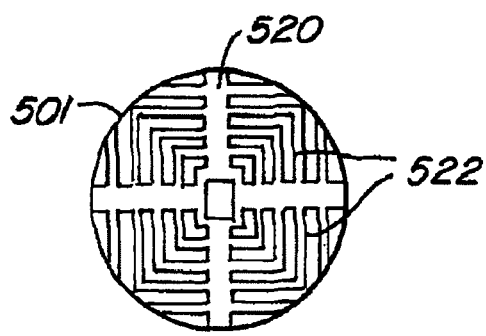
Figure 62:
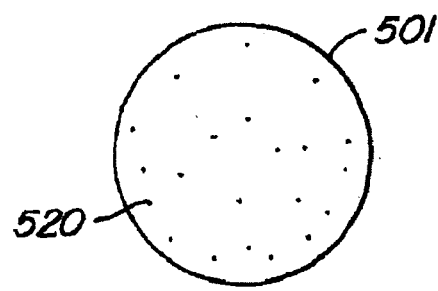
Figure 63A:
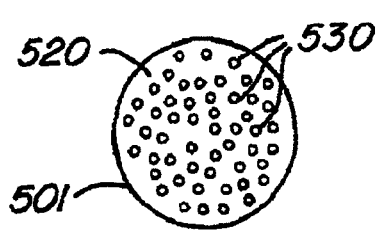
Figure 63B:
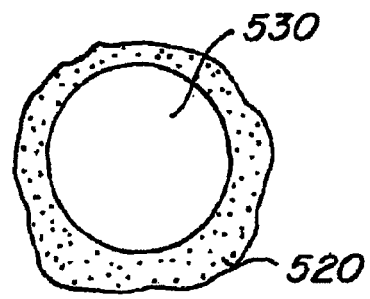

FIGS. 61A-C and FIG. 62 illustrate the use of a sheet of material 520 to form a filter structure. The material 520 may have any of a variety of shapes formed in it using any suitable process such as punching, piercing, laser cutting and the like. FIG. 61A illustrates a circular pattern 521 formed in material 520. FIG. 61B illustrates a rectangular pattern 523 formed in material 520. FIG. 61C illustrates a complex pattern 522 cut into material 522. It is to be appreciated that the material 520 may also be placed in the frame 501 without any pattern (FIG. 62). The illustrative embodiment of FIG. 62 may be useful for occluding the flow within a lumen. Suitable materials 520 for an occlusion application include for example, wool, silk polymer sheets, other material suited to prevent blood flow in a lumen when extended across a lumen and the like. Additionally, the filter material 520 may be a porous material having pores 530 (FIG. 63A). The material 520 may be selected based on the average size of individual pores 530 (FIG. 63B) depending upon the procedure or use of the filter device. For example, the material 520 may be any of the porous materials using in existing distal protection and embolic protection devices. In general, a wide variety of pore 530 sizes are available and may range from 0.010" to 0.3". Other pore sizes are also available depending upon the material 520 selected.

Figure 64A:
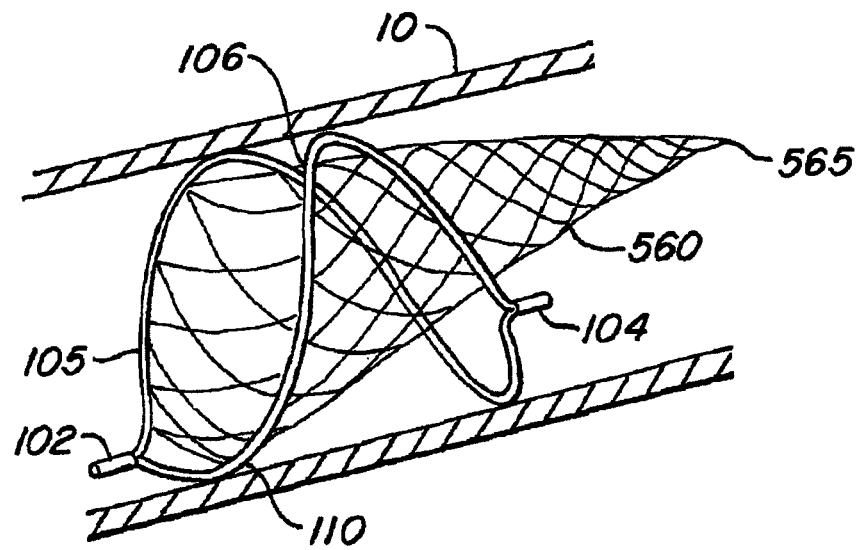
Figure 64B:
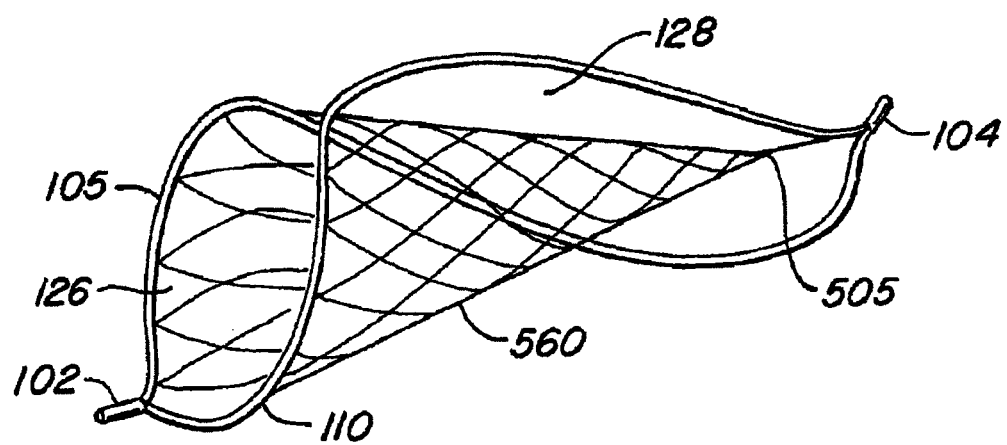
Figure 65A:
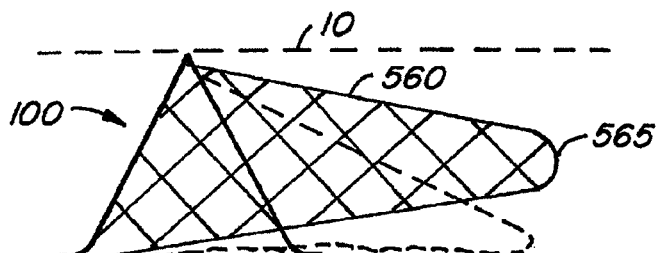
Figure 65B:
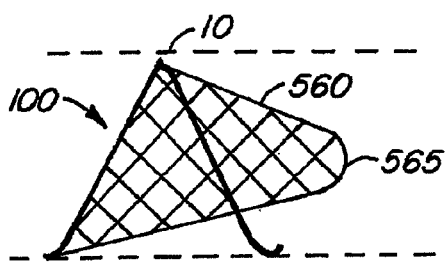
Figure 65C:
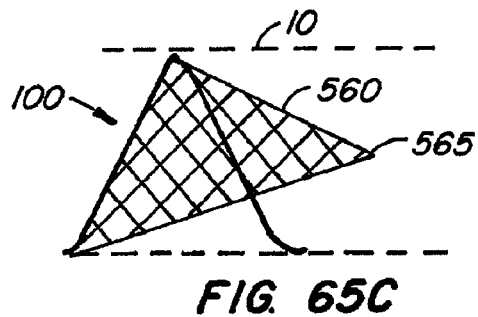
Figure 65D:
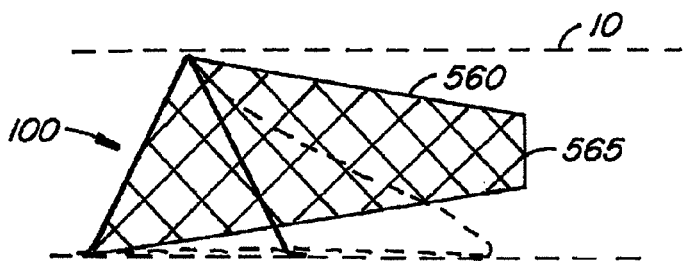
Figure 65E:
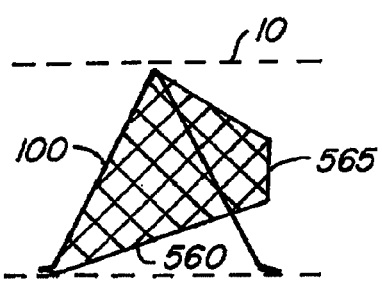
Figure 65F:
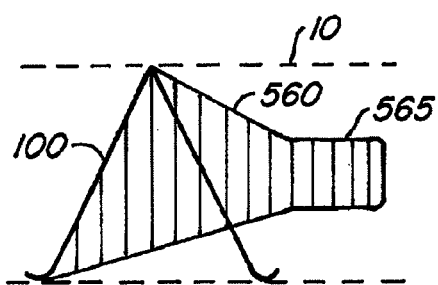

FIGS. 64-65F illustrate the use of nets or other web structures within the filtering device. The various net structure embodiments described herein are used as material capture structures within filter device embodiments of the present invention. Each of these alternative is illustrated in a support structure similar to that of device 100 in FIG. 2A and elsewhere. When deployed within the lumen 10, the material capture structure 560 has a defined shape such as a cone with a discrete apex 565 (FIG. 64A). In this embodiment, the net structure is long enough to contact the sidewall of the lumen 10 when deployed in the lumen 10. Alternatively, the apex 565 may be attached to the end 104 to keep the net 560 in the lumen flow path and out of contact with the lumen sidewall (FIG. 64B). The net 565 may also have a rounded apex 565 (FIG. 65A) or a truncated cone (flat bottom) (FIG. 65D). Alternatively, the net 560 may a discrete apex 565 so short that it will not contact the lumen sidewall when deployed (FIG. 65B). The short net may also have a rounded apex 565 (FIG. 65B), a flat apex (FIG. 65E) or a sharp apex (FIG. 65C). In addition, the net 560 may have a compound apex 565 (FIG. 65F).

Figure 66:
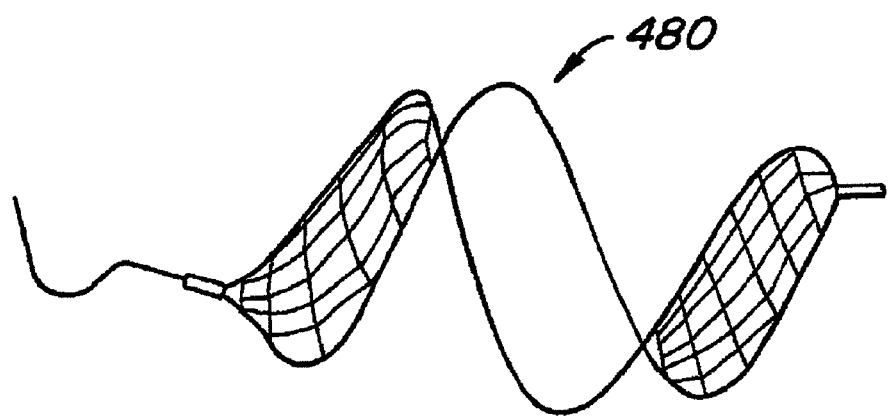
FIGS. 66 and 67 illustrate various filtering device configurations.
Figure 67:
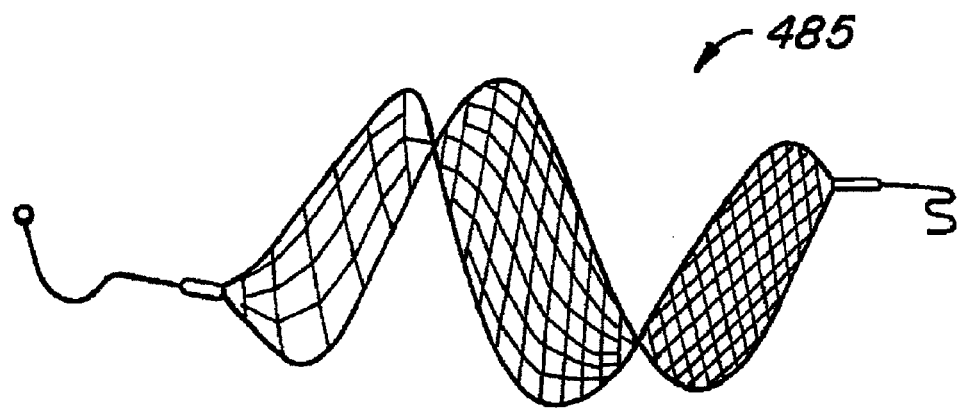

FIGS. 66 and 67 illustrate how various different features described above can be combined. For example, FIG. 66 illustrates a multi-support frame device 480 having a retrieval feature on only one end and an open frame (i.e., no filter structure). FIG. 67 illustrates an alternative multi-support frame device 485 having different retrieval features on each end, filter structures in each of the support structures and each of the filter structures having a different filter capacity. It is to be appreciated that the above described details of the construction, components, sizes, and other details of the various filter device embodiments described herein may be combined in a number of different ways to produce a wide array of alternative filter device embodiments.

Delivery, Recovery and Repositioning of a Filtering Device

Figure 68A:
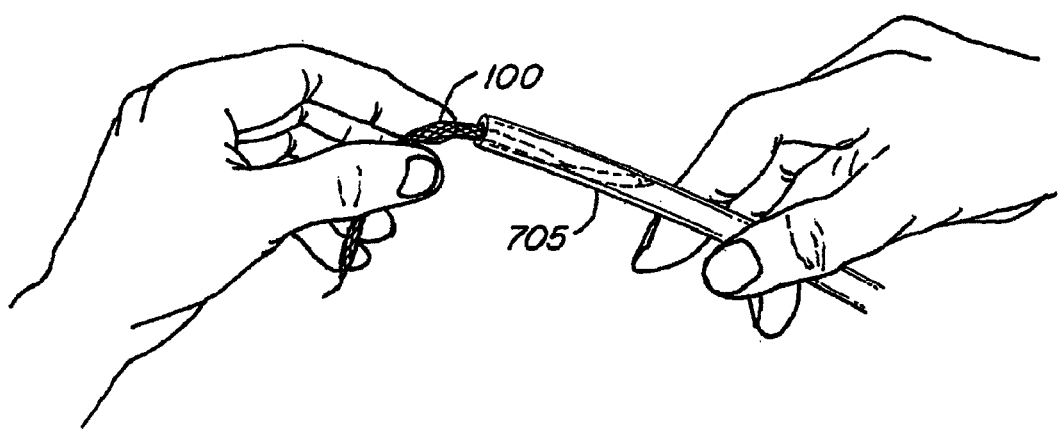
FIGS. 68A-74D illustrate various techniques related to the delivery, recovery and repositioning of filtering devices.
Figure 68B:
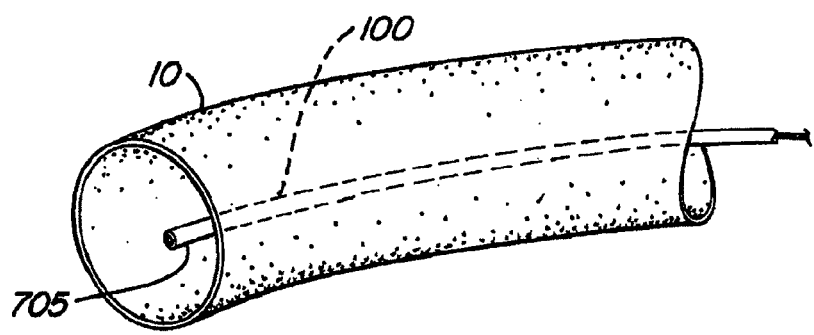

FIG. 68A illustrates an embodiment of the filter device 100 of the present invention loaded into an intravascular delivery sheath 705. The device 100 is illustrated and described above, for example, in relation to FIG. 16A. Using conventional endoluminal and minimally invasive surgical techniques, the device can be loaded into the proximal end of the sheath 705, before or after advancing the sheath 705 into the vasculature, and then advanced through the sheath using a conventional push rod. The push rod is used to advance the device 100 through the delivery sheath lumen as well as fix the position of the device (relative to the sheath 705) for device deployment. In one preferred technique, the device is loaded into the proximal end of a delivery sheath that has already been advanced into a desired position within the vasculature (FIG. 68B). The device 100 may be pre-loaded into a short segment of polymeric tubing or other suitable cartridge that allows the device 100 to be more readily advanced through a hemostasis valve.

Figure 69A:
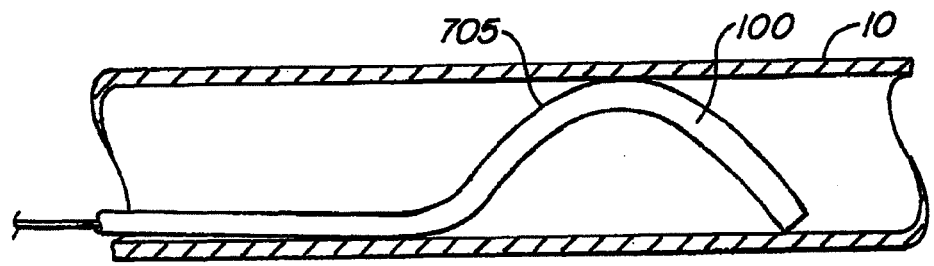
Figure 69B:
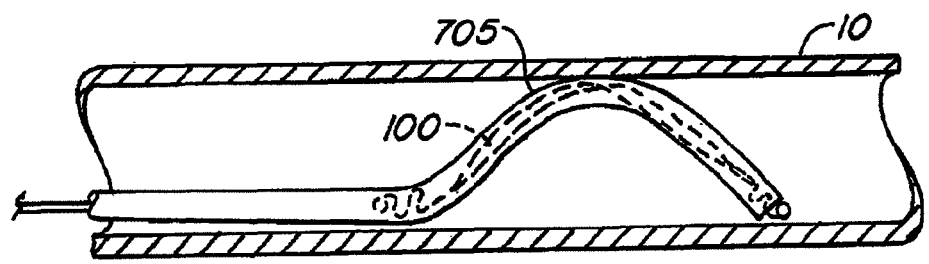
Figure 69C:
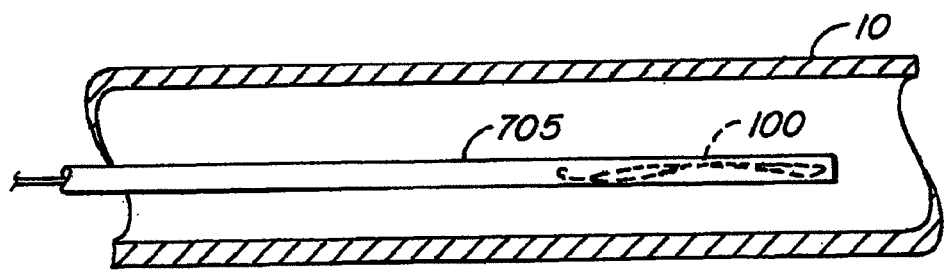
Figure 69D:
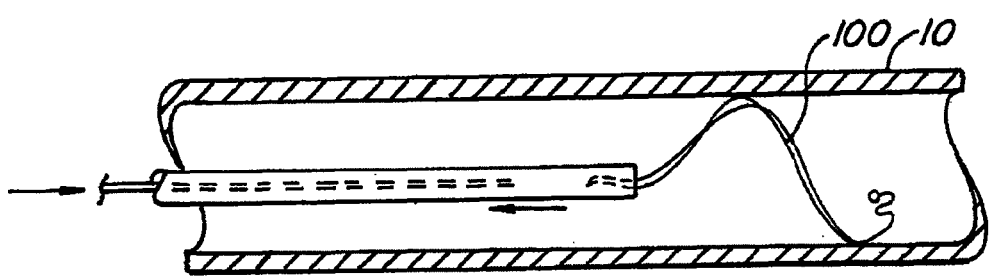

When used with a compliant delivery sheath 705, the preformed shape of the device 100 deforms the sheath to conform to the device shape (FIG. 69A, 69B). Accordingly, a flexible, compliant sheath 705 assumes the curvature of the stowed device. The deformation of the delivery sheath 705 helps stabilize the position of the sheath 705 in the vasculature and facilitates accurate deployment of the device 100 to the intended delivery site. In contrast, a non-compliant delivery sheath 705 (i.e., a sheath that is not deformed to conform to the preformed shape of the device 100) maintains a generally cylindrical appearance even through the device 100 is stowed within it (FIG. 69C). Regardless of the type of sheath used, device delivery is accomplished by using the push rod on the proximal side of the device to fix the position of the device within the sheath 705 and then withdrawing the sheath 705 proximally. As the device 100 exits the distal end of sheath 705, it assumes the pre-formed device shape (FIG. 69D).

Figure 70:
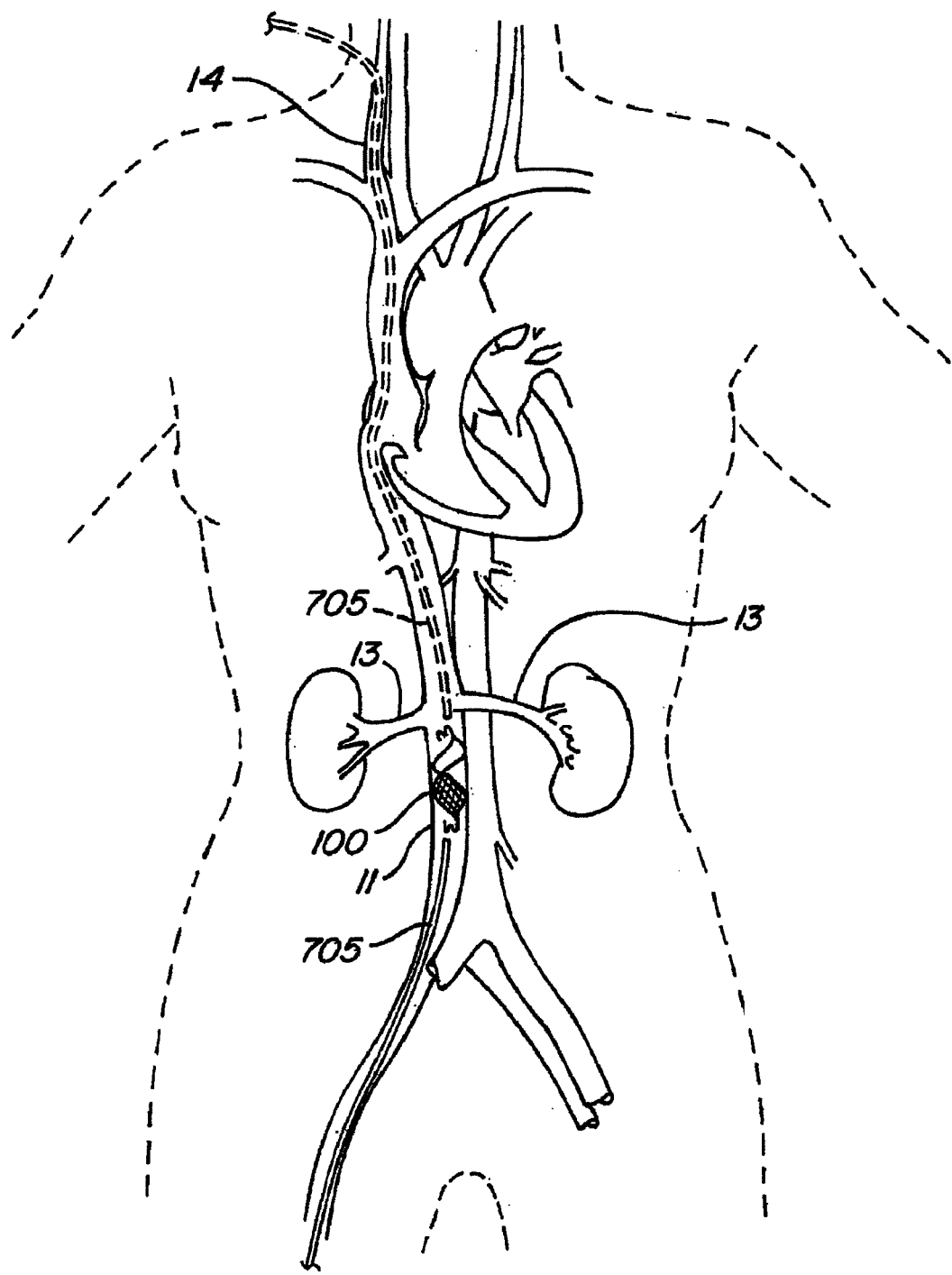

The symmetrical device shape (see e.g., devices in FIGS. 15 and 16A), facilitates the deployment and retrieval of the device from multiple access points in the vasculature. A device 100 is shown positioned in the vasculature within the inferior vena cava 11 immediately below the renal veins 13 (FIG. 70). A femoral access path (solid) and a jugular 14 access path (phantom) are illustrated. The femoral access path (solid) and a jugular access path may each be used for device deployment, repositioning and retrieval. Alternatively, the vena cava could be accessed via brachial or antecubital access for device deployment, repositioning and retrieval.

Figure 71A:
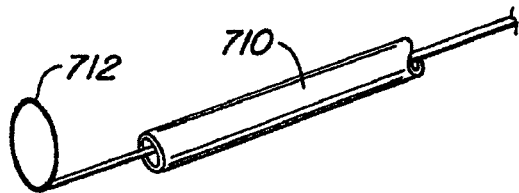
Figure 71B:
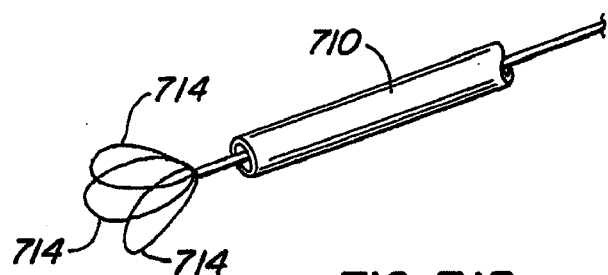

Retrieval of the devices is most preferably accomplished by endoluminal capture using one of the retrieval features described herein. (i.e., FIGS. 27A-E) The retrieval features described herein have been designed to work well using a commercially available snares two of which are illustrated in FIG. 71A and FIG. 71B. The single loop gooseneck snare 712 is illustrated in FIG. 71 inside of a recovery sheath 710. The multiple loop Ensnare 714 is illustrated in FIG. 71B inside of a recovery sheath 710. These conventional snares are controlled by a physician using a flexible, integral wire.

Figure 72A:
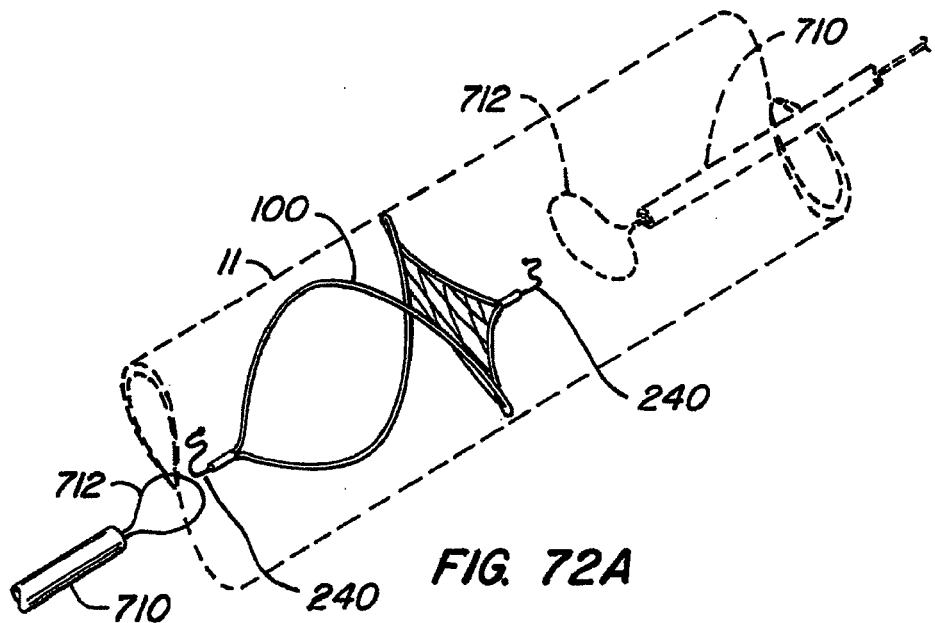
Figure 72B:
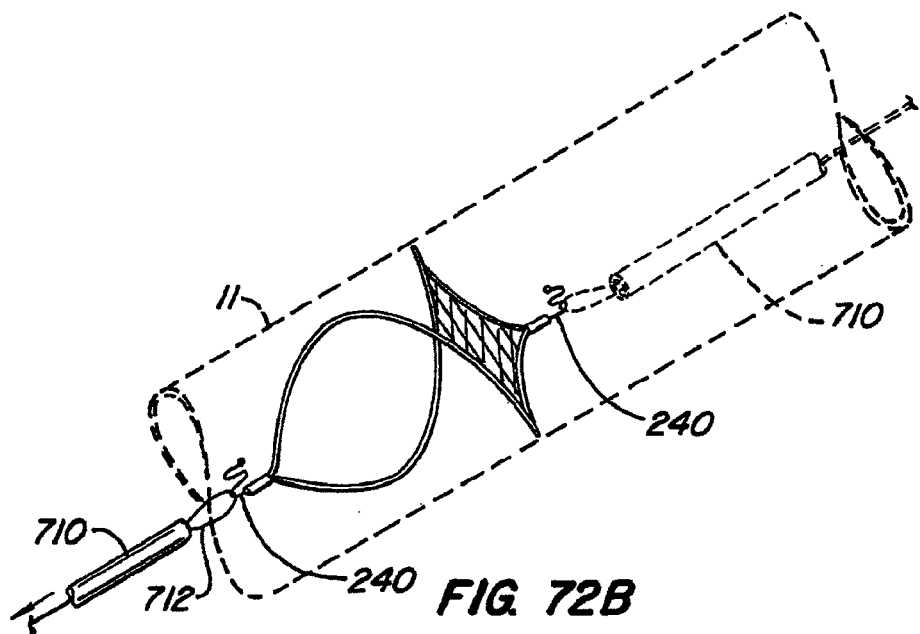
Figure 72C:
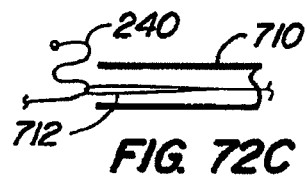
Figure 72D:
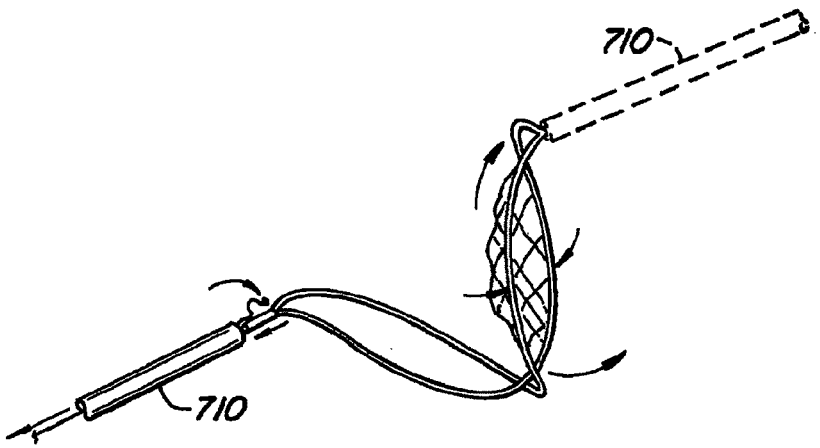

The sequence of device recapture and removal from a body lumen (here the vena cava 11) is illustrated in FIGS. 72A-C. In these figures, the solid lines are for a femoral recovery and the phantom lines are for a jugular recovery (e.g., FIG. 70). A collapsed snare is advanced via a delivery sheath to the proximity of the retrieval feature 240 (FIG. 72A). Once in place, the snare 712 is exposed and assumes a pre-defined expanded loop shape which is looped over the retrieval feature 240 as illustrated from either end in FIG. 72B.

The snared device 100 can then be either pulled into the sheath 710, or alternatively and more preferably, the recovery sheath 710 is advanced over the device 100 while maintaining positive control of the snare 712 as the sheath 710 advances over the device 100. Advancing the recovery sheath 710 over the device 100 facilitates atraumatic removal of the device 100 from any tissue that has grown in or around the device 100. The retrieval action, which tends to collapse the device radially inward (FIG. 72D), also facilitates removal from any tissue layer formed on the device. Recovering the filtering device by pulling on a flexible retrieval feature attached to the filtering device. Moreover, pulling on a portion of the filter structure (i.e., a retrieval feature) removes the opposing spiral elements from the lumen wall.

As the device is drawn into the sheath 710, the pre-formed shape of the device also urges the support members away from the lumen wall which also assists in atraumatic device removal.

Figure 72E:
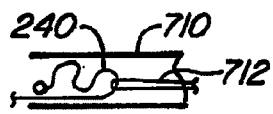
Figure 72F:
Figure 73A:
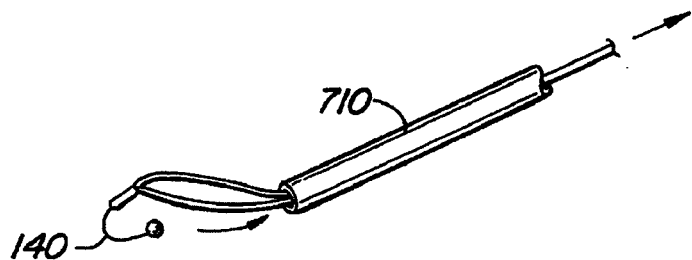
Figure 73B:
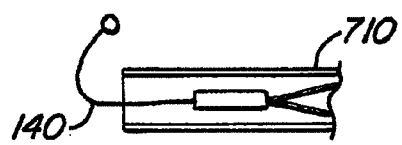
Figure 73C:
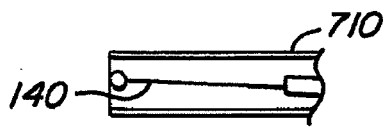
Figure 73D:
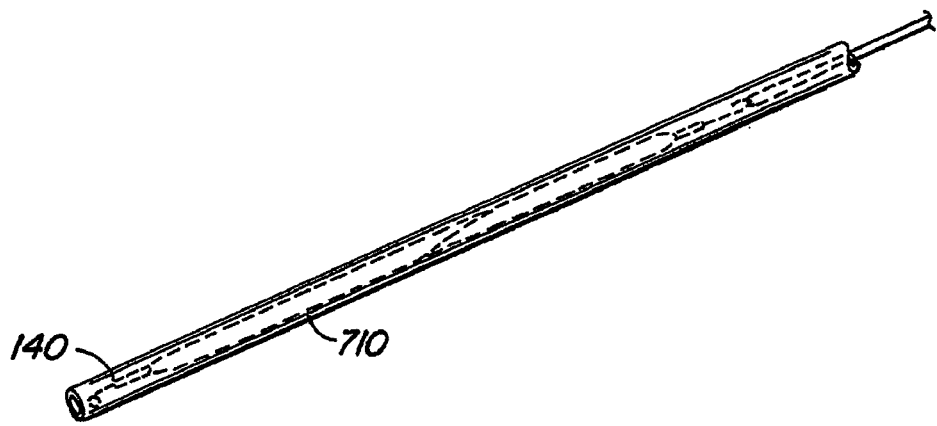

The flexible retrieval element 240 assumes a collapsed configuration as it is being drawn into the recovery sheath as illustrated in FIG. 72C and FIG. 72E. Note that the retrieval feature 240 on the opposite end of the device assumes a straightened configuration as is drawn into the recovery sheath (FIG. 72F). An additional embodiment, in which a single curved retrieval feature 140 (FIG. 27A) is withdrawn into the delivery sheath 710 as shown in FIG. 73A. The distal retrieval feature (relative to the snare) assumes a straightened configuration FIG. 73C from a curved configuration FIG. 73B as is completely withdrawn into the sheath FIG. 73D.

Additionally, repositioning the filter 100 from one lumen position to another is illustrated in FIGS. 74A-74D. Because of the atraumatic design of filter devices of the present invention, repositioning of the filter device 100 may be accomplished by fully recapturing (FIG. 74C) or only partially recapturing (FIG. 74B) the device 100 into a recovery sheath 710. The atraumatic design of the device 100 allows the device to simply secured by one end (FIG. 74B) and pulled along the lumen wall into the desired position and then released. The delivery sheath and recovery sheath are provided with the same reference numbers since filter devices of the present invention may be deployed into and recovered from the vasculature using sheaths that are about the same size. As such, devices of the present invention may be deployed into the vasculature from a delivery sheath having a first diameter. Then, the device may be retrieved from the vasculature using a recovery sheath having a second diameter no more than 2 Fr larger than the first diameter (1 Fr=0.013"=⅓ mm). Alternatively, the second diameter may be no more than 1 Fr larger than the first diameter or, alternatively, the first diameter is about the same as the second diameter.

Figure 74A:
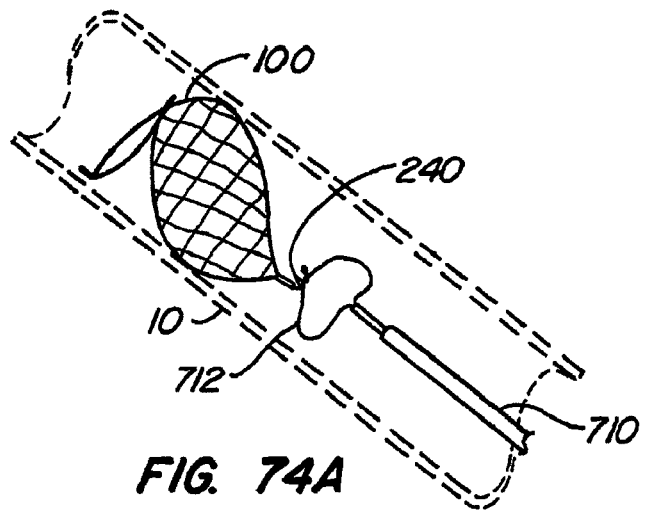
Figure 74B:
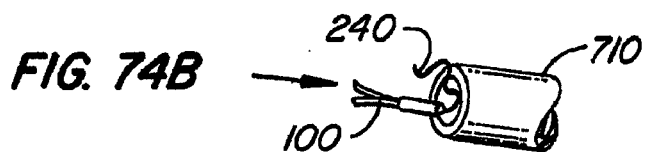
Figure 74C:
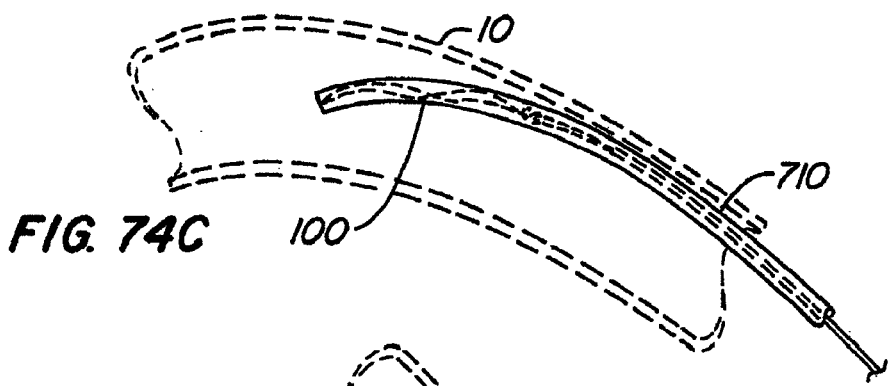
Figure 74D:
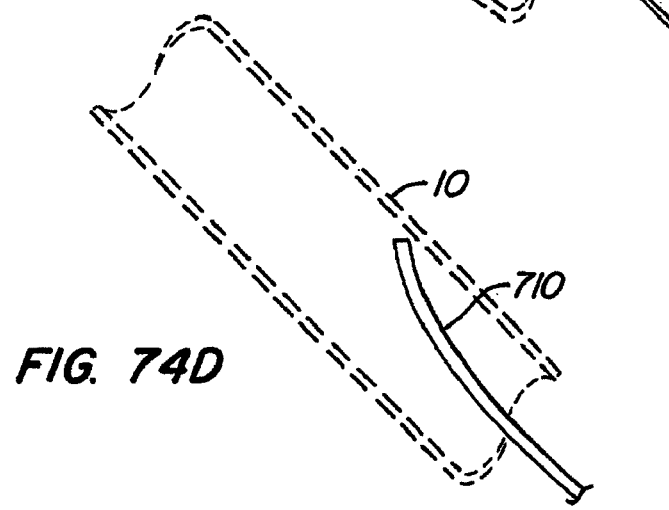

In a full recovery, the device is pulled completely into a recovery sheath (FIG. 74A), the sheath is repositioned from the original position (FIGS. 74A, 74C) to a second position (FIG. 74D) and deployed into the vasculature again (FIG. 69D). In the case where the snare wire columnar strength is insufficient to redeploy the device, the snare can be delivered within a secondary inner sheath within the retrieval sheath. This allows the positive control of the retrieval feature to be obtained, such as illustrated in FIG. 74B, the device withdrawn into the retrieval sheath and then redeployed with the inner sheath acting as a push rod.

Various Methods of Using Filtering Devices

Figure 75A:
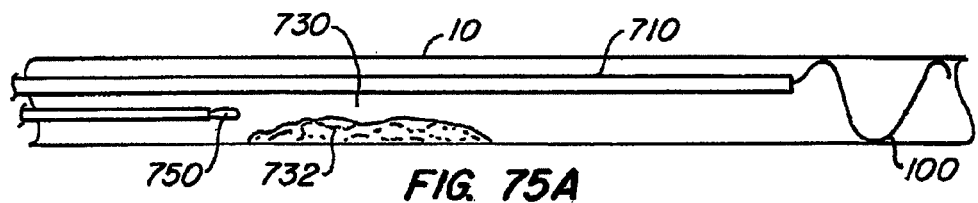
Figure 75B:
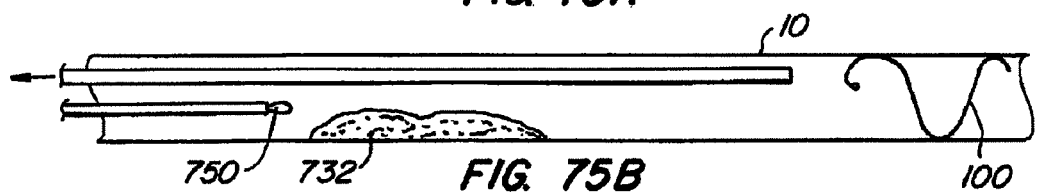
Figure 75C:
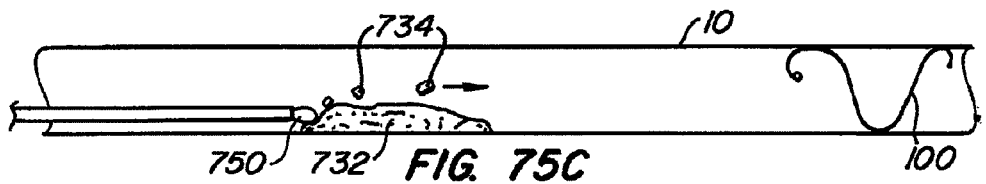
Figure 75D:
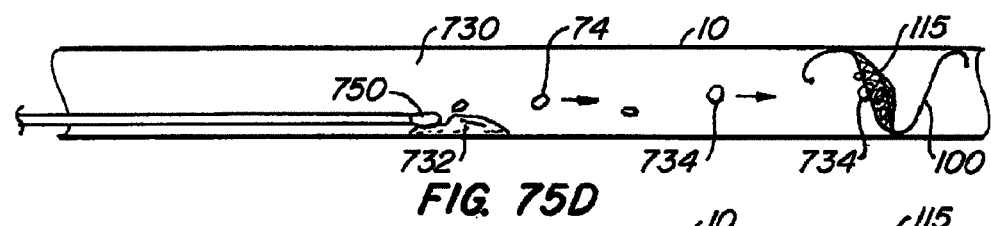
Figure 75E:
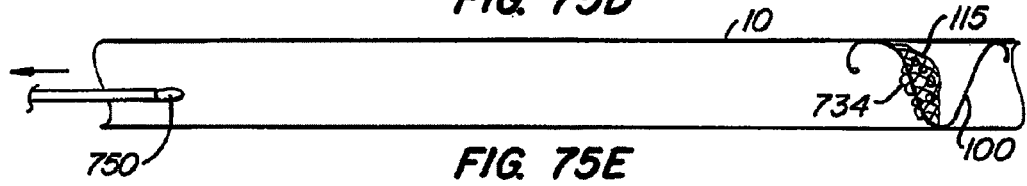
Figure 75F:
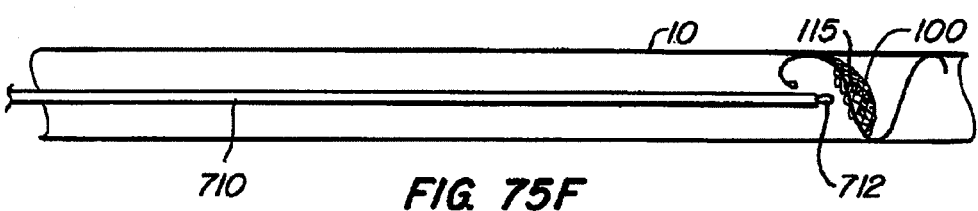

Embodiments of filter devices of the present invention may be used in methods of providing distal protection in procedures such as, for example, thrombectomy, arthrectomy, stenting, angioplasty and stent grafting. It is to be appreciated that embodiments of filter devices of the present invention may be used in veins and arteries. An exemplary procedure is illustrated in FIGS. 75A-I and FIGS. 76A-E. In each procedure, the device 100 is positioned in an un-tethered fashion adjacent to the treatment region 730. The sequence FIGS. 75A-I illustrate the delivery sheath 710 positioning FIG. 75A, complete deployment FIG. 75B into the lumen 10. A conventional treatment device 750 using mechanical, electrical energy or other suitable method is used to clear the undesired material 732 from the lumen wall (FIG. 75C). Some debris 734 removed from the lumen wall through the use of treatment device 750 is subsequently embolized into the blood stream (FIG. 75C) and trapped by the filter 100 (FIG. 75D). The conventional treatment device 750 is removed (FIG. 75E)

and thereafter the advancement of recapture sheath 710 is advanced into recovery position (FIG. 75F).

Figure 75G:
Figure 75H:
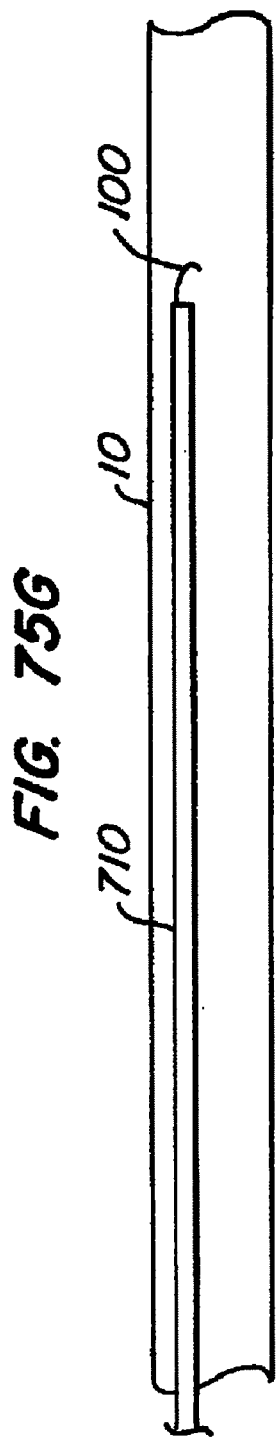
Figure 75I:

The entrapped debris 734 is then removed prior to recapturing the device with methods such as, for example, aspiration, delivery of therapeutic agents or maceration. Additionally, the device and entrapped debris can be recaptured in whole and removed via the same sheath used to recapture the device as illustrated in FIG. 75G. The device 100 and debris 734 are then withdrawn into the sheath 710 (FIG. 75H), and the sheath withdrawn from the vasculature (FIG. 75I).

Figure 76A:
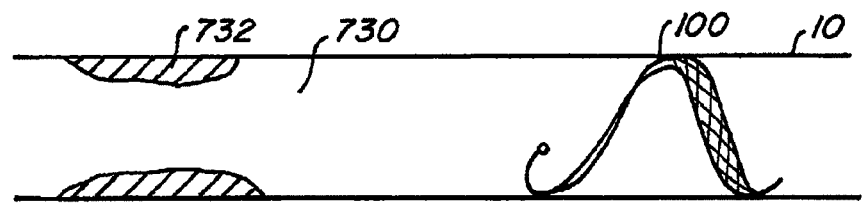
Figure 76B:
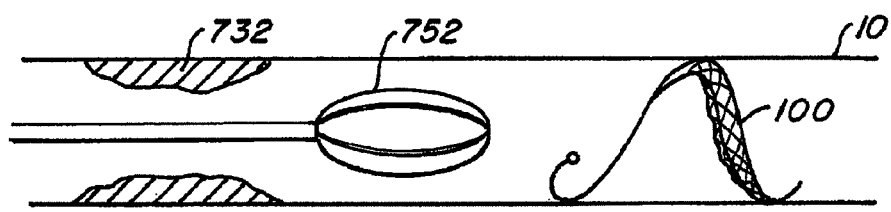
Figure 76C:
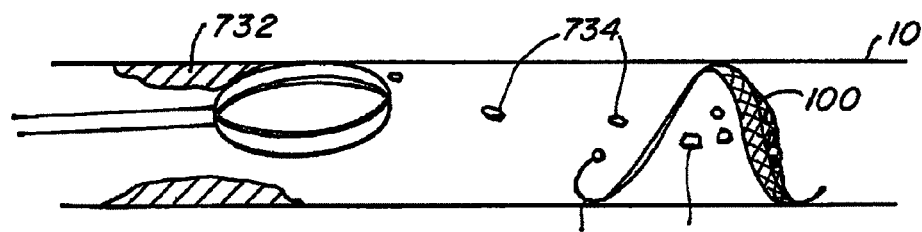
Figure 76D:
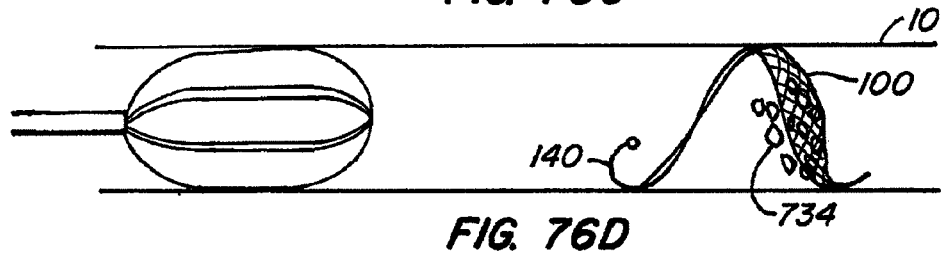
Figure 76E:
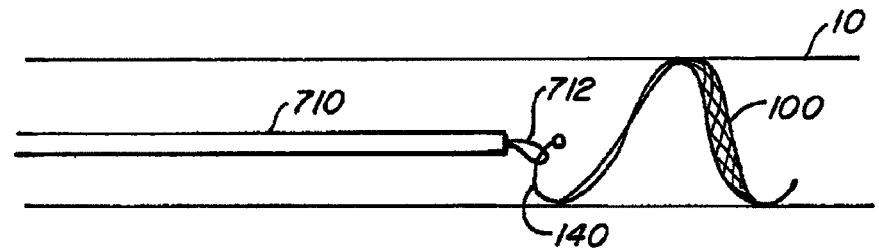

Similarly, an additional use of the invention as un-tethered distal protection is illustrated in FIGS. 76A-E, in which a balloon 751 is used to expand the lesion 732 such as in the case of balloon angioplasty, often performed prior to stenting a vessel to keep it open. For this procedure a balloon catheter is advanced to the lesion site and inflated FIG. 76 B, plaque 732 is pushed outward by the balloon (FIG. 76C), thus reestablishing normal blood flow. Any particulate matter 734 embolized by the procedure is trapped by the filter (FIG. 76D). The debris 734 can then be removed prior to filter retrieval as previously described or the device with trapped debris can be removed together.

An additional method practiced widely in the art is the use of tethered distal protection adjunctive to the previously described procedures (i.e., the device 100 remains tethered during the procedure). Embodiments of the filtering device of the present invention may also be used for this purpose as illustrated in FIGS. 77A-77E. Positive control of the filter 100 is maintained via an integral wire or snare connected to the device 100. The connection between the integral wire or snare to the device 100 is maintained during the procedure and may be, in some embodiments, used as a guidewire. As illustrated in FIG. 77B, connection to the device 100 is maintained a while performing a procedure to treat the vasculature in proximity to the location (i.e, treat the lesion 732).

An example of a tethered distal protection method is illustrated in FIGS. 77A-77E. An embodiment of a filter device 100 is deployed distal to the lesion 732 to be treated (FIG. 77A), the treatment is initiated (FIG. 77B), and embolized material 734 is captured in the filter 100 (FIG. 77C). Thereafter, the debris 734 is removed prior to filter recapture or, alternatively, with treatment in the filter 100 via a sheath as previously described. The device 100 is recovered into the sheath (FIG. 77D) and removed from the lumen 10 (FIG. 77E).

Figure 78A:
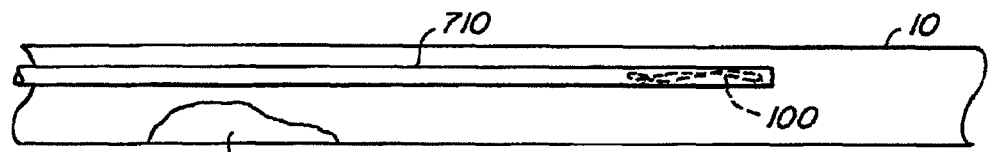
Figure 78B:
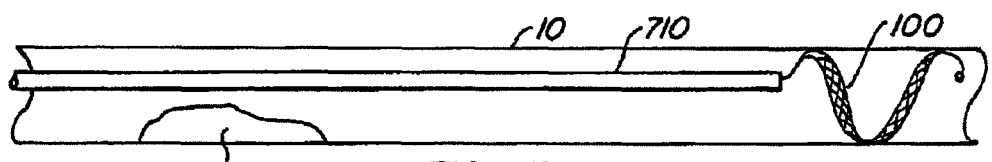
Figure 78C:
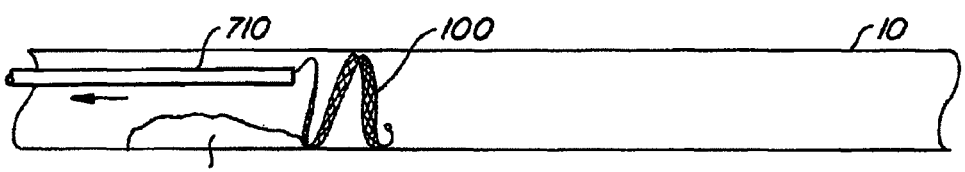
Figure 78D:
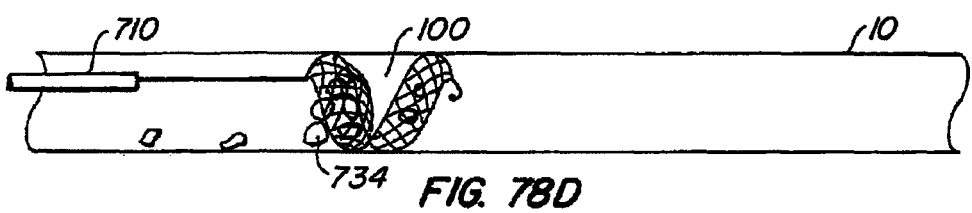
Figure 78E:
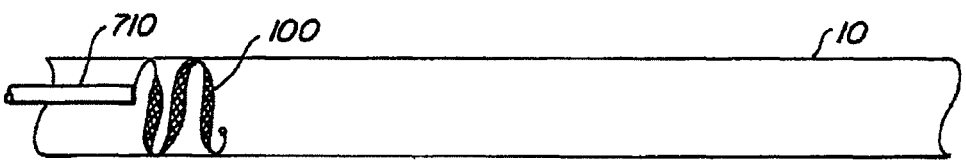
Figure 78F:
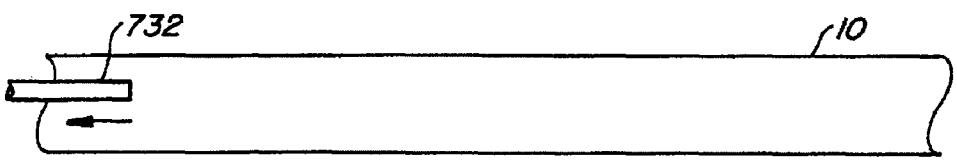

A tethered device (FIG. 77A, 78A) can also be employed to mechanically dislodge and remove embolic material 732 from a vessel 10, such as in the case of a thrombectomy. This offers a simple means of removing and trapping debris without requiring multiple devices to achieve the same goal. For this method, the tethered device is advanced downstream of the lesion site (FIG. 78A), and deployed (FIG. 78B). The tethered, deployed filter 100 is then drawn across the lesion 732 (FIG. 78C) to pull the thrombus from the vessel wall and into the filter 100 (FIG. 78D). The embolized material 734 is then removed via the methods previously described (FIG. 78E), tethered device is drawn into the sheath and removed from the lumen (FIG. 78F).

Delivery of Pharmacological Agents Using Filtering Devices

Embodiments of the filter device of the present invention may also be used for delivering a pharmacological agent within a lumen. Delivery of the a pharmacological agent within a lumen may be accomplished using any component of the filtering device. For example, the filter support structure may deliver a pharmacological agent. In one alternative, the support structure is covered by a multi-lumen structure and the multi-lumen structure is configured to release a pharmacological agent. In one alternative, a lumen of the multi-lumen structure is at least partially filled with a pharmacological agent. In another aspect, a lumen in a multi-lumen structure has ports that allow for the release of a pharmacological agent stored within the lumen. In one alternative, a cavity formed in a support member is filled with a material. In one aspect, the material in the cavity is a pharmacological agent. The filter may deliver a pharmacological agent. In one aspect the material capture structure is coated with a pharmacological agent.

Figure 33:
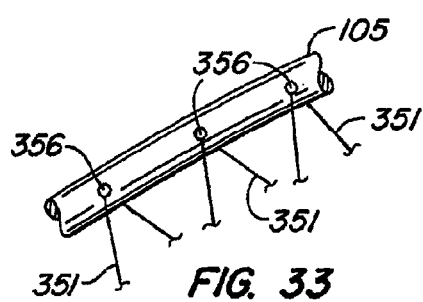
Figure 79:
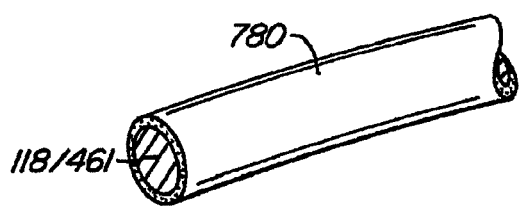
FIGS. 79-82 illustrate several alternative filtering device configurations adapted for the delivery of pharmacological agents.
Figure 80:
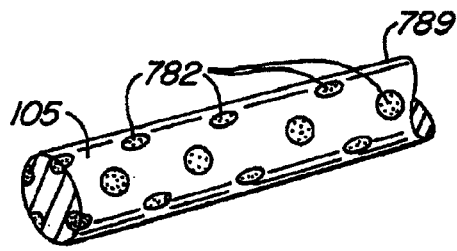

Additional embodiments of the invention provide for the ability to deliver therapeutic agents via the material capture structure as well as the support structure covering. FIG. 79 illustrates a therapeutic agent coating 780 attached to a filament 118/461. FIG. 80 illustrates a composite structure 789 formed by having one or more cavities formed in a support structure 105 filled with one or more therapeutic agents or other material. The cavities may be formed as described above with regard to FIGS. 33, 35 and 36. These composite structures can be designed to elute a therapeutic agent via a specific elution curve by varying thickness, density as well as location of the therapeutic agent on the filter device component. This therapeutic agent could be, for example, any pharmacological agent used in the treatment of the body, an anticoagulant coating (i.e., Heparin), an agent prevent or sloe fibrous tissue growth, other agents selected from those used in vascular stents including drug eluting stents.

Figure 81:
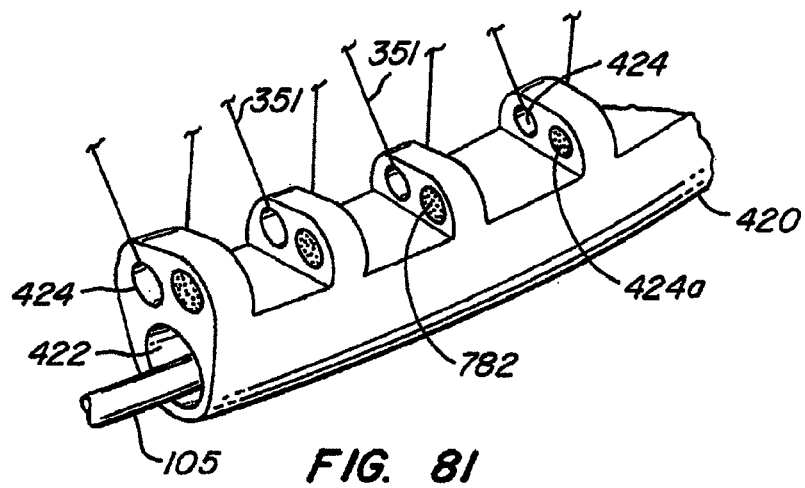
Figure 82:
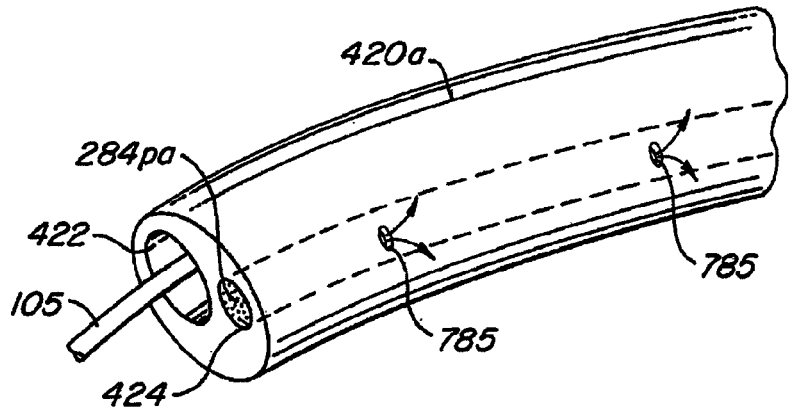
Figure 83A:
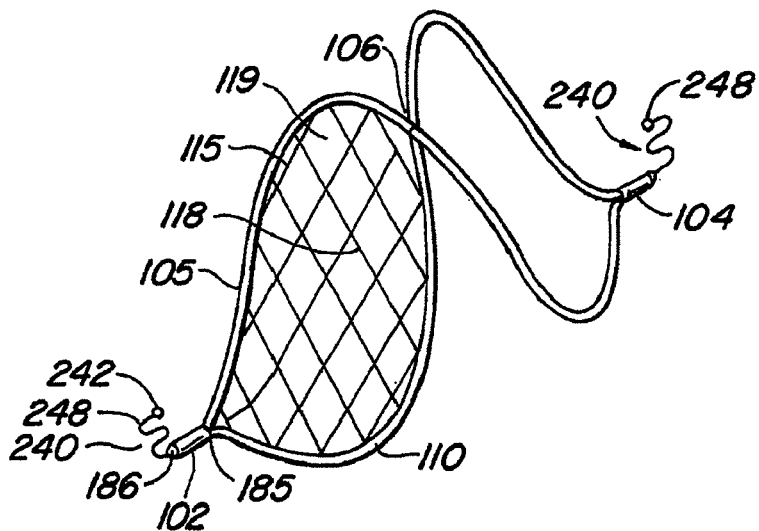
FIGS. 83A-87 illustrate several filtering device prototypes.
Figure 83B:
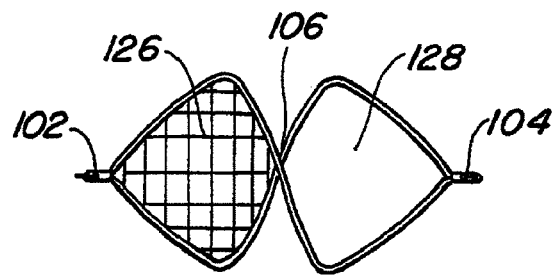
Figure 83C:
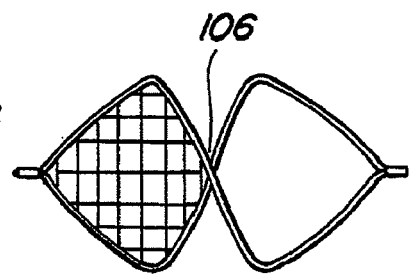
Figure 83D:
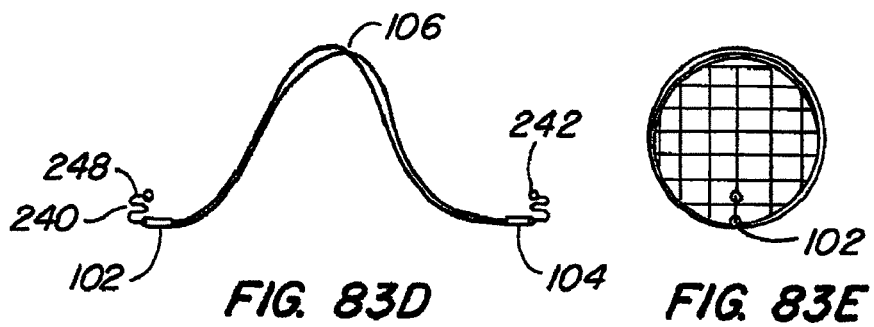
Figure 83E:
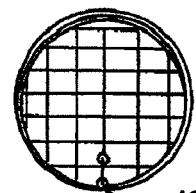
Figure 84A:
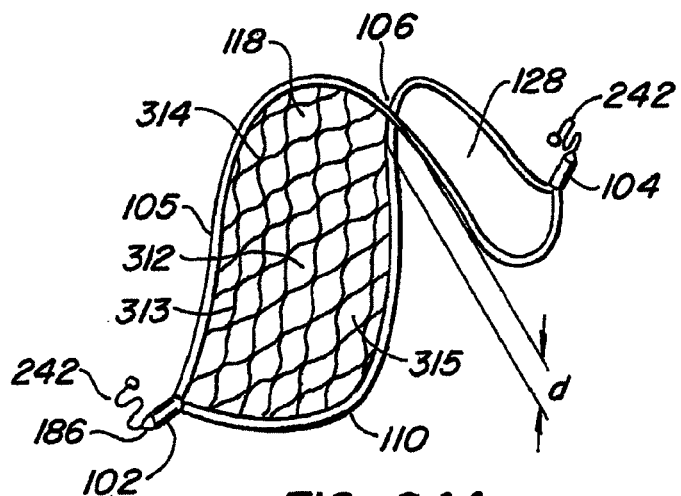
Figure 84B:
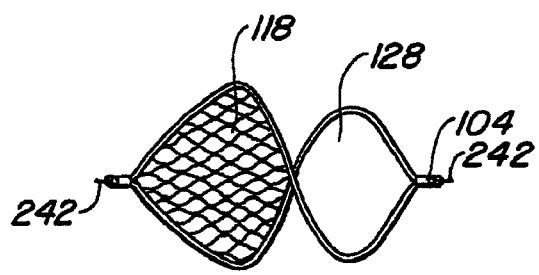
Figure 84C:
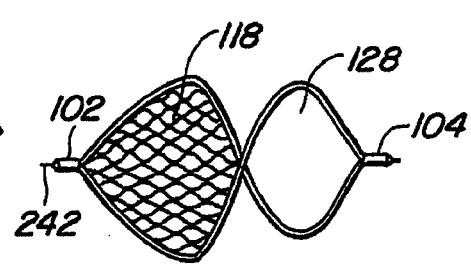
Figure 84D:
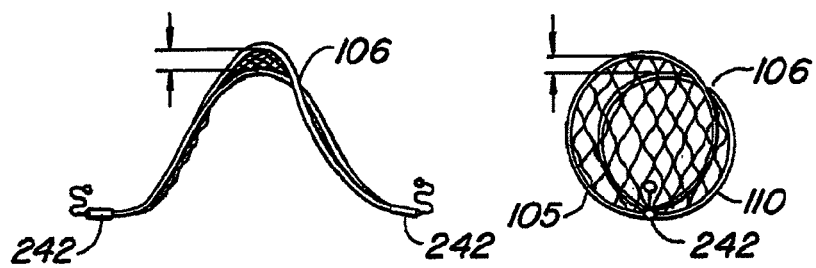
Figure 84E:
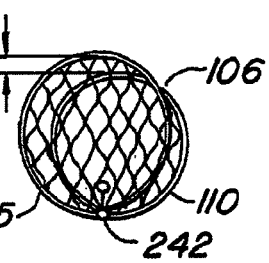
Figure 85A:
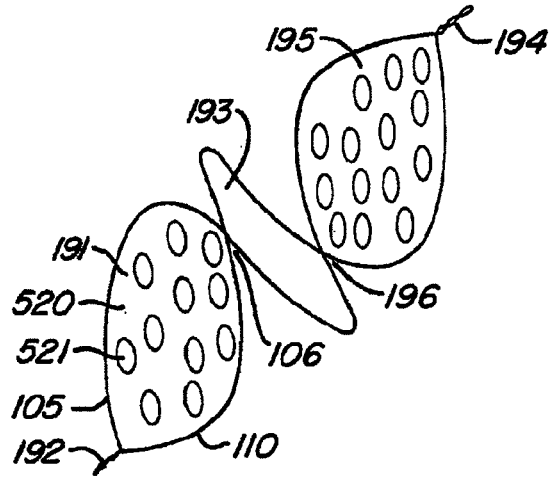
Figure 85B:
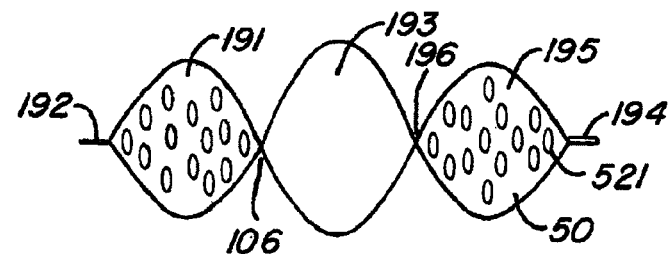
Figure 85C:
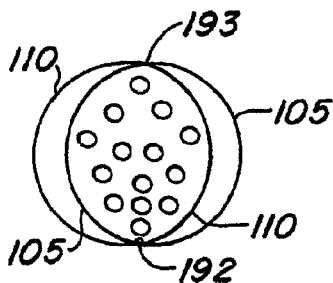
Figure 85D:
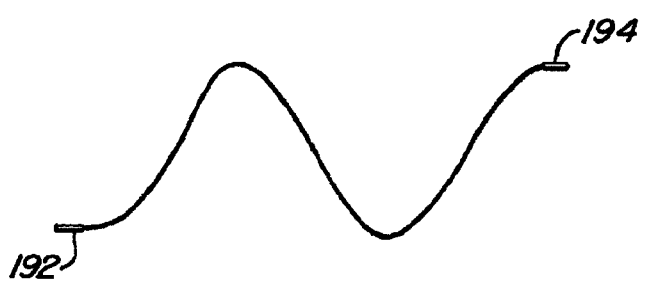
Figure 86A:
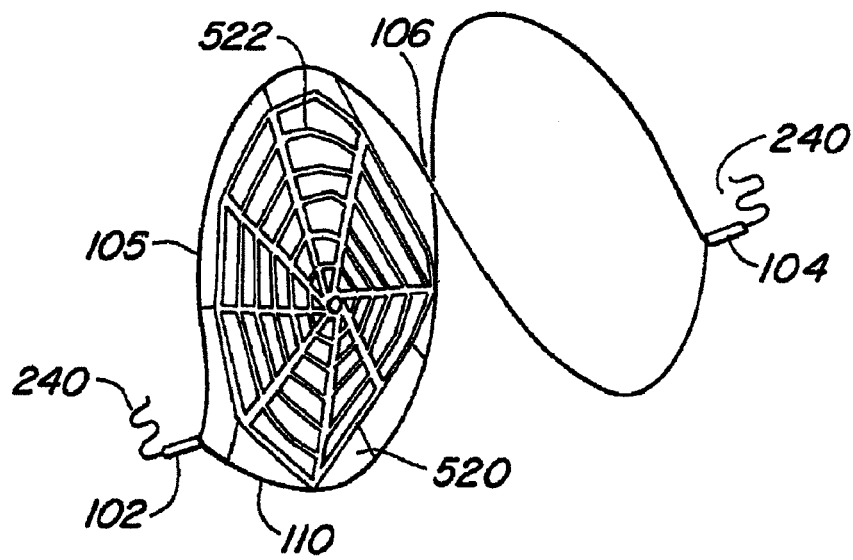
Figure 86B:
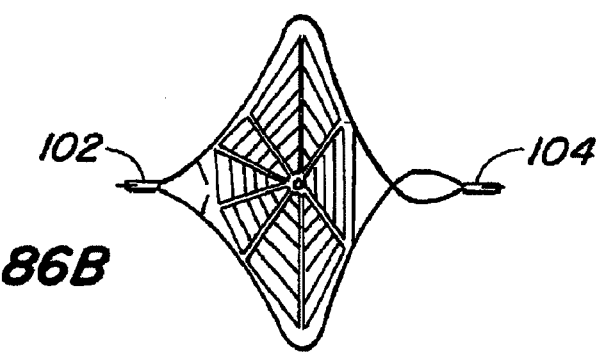
Figure 86C:
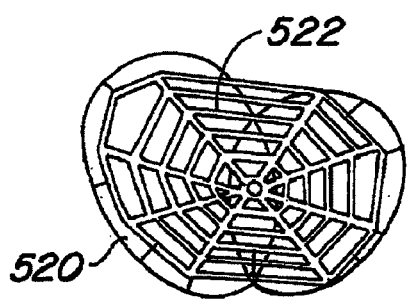
Figure 86D:
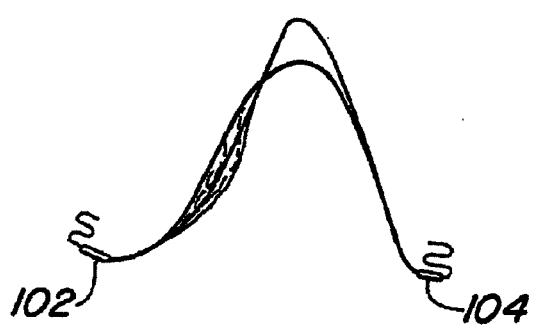

FIG. 81 and FIG. 82 illustrate the use of the covering 420, 420a positioned over a support structure as the delivery means for providing pharmacological agents into a lumen. FIG. 81 illustrates a pharmacological agent 782 in a lumen 424a of a multi-lumen structure such as described above with regard to FIGS. 44, 45. As illustrated in FIG. 82, the therapeutic agent 784 fills a lumen 424 in a multi-lumen covering 420a over the support structure 105. Release ports 785 formed in the side of lumen 424 allow delivery of the agent to the blood or tissue. Control of the therapeutic agent elution parameters could be controlled via the size or spacing of the release ports 785 and/or through the use of controlled release pharmacological agents.

Prototype Filtering Devices

FIGS. 83A-83E illustrate perspective (FIG. 83A), plan (FIG. 83B), bottom (FIG. 83C), side (FIG. 83D) and end (FIG. 83E) views of a prototype filter according to an embodiment of the present invention. The prototype has previously described features and common elements have the same reference numbers have been incorporated into these illustrations. The support structure 105, 110 was formed with electropolished 0.013" OD Nitinol wires, shape set to form two substantially equal open loops 126, 128 of approximately 1" diameter. The support structure wire used for support structure 105 was ground down to a wire diameter of 0.010" and used to form flexible retrieval feature 240 on each end (i.e., FIG. 28C). An atraumatic feature (here ball 242) is created on the end of the wire by exposing the wire to plasma. A radio opaque marker, here a Tantalum marker band 248 attached below the ball 242. The material capture structure 115 has filter cells 119 constructed with filaments 118. The filaments 118 are 7-0 ePTFE suture. The filaments are attached to the support structure using method shown in FIG. 47. The cover 185 used to join the ends is a tapered Nitinol tube 186 that is crimped around the support structures, as illustrated in FIG. 24.

FIGS. 84A-84E illustrate perspective (FIG. 84A), plan (FIG. 84B), bottom (FIG. 84C), side (FIG. 84D) and end (FIG. 84E) views of a prototype filter according to an embodiment of the present invention. This embodiment is similar to the embodiment of FIG. 83A. In this embodiment, the material capture structure 115 is replaced with material capture structure 312 an made of extruded polymeric netting described above with regard to FIG. 56. This embodiment also illustrates how the support structures 105, 110 are not in contact (i.e., separated by a distance "d") at the crossover 106.

FIGS. 85A-85E illustrate perspective (FIG. 85A), plan (FIG. 85B), side (FIG. 85D) and end (FIG. 85C) views of a prototype filter according to an embodiment of the present invention. This embodiment is similar to the filter device described in FIG. 14A and common reference numbers are used. In this embodiment, a material capture structure is constructed from a continuous sheet of polymeric material 520 into which circular holes 521 are created via mechanical or laser cutting (as described above with regard to FIG. 61A).

FIGS. 86A-86D illustrate perspective (FIG. 86A), plan (FIG. 86B), side (FIG. 86D) and end (FIG. 85C) views of a prototype filter according to another embodiment of the present invention. In this prototype filter, a material capture structure constructed from a continuous sheet of polymeric material 520 into which a pattern 522 voids are created via mechanical or laser cutting to create a net-like structure (FIG. 61C).

Figure 87:
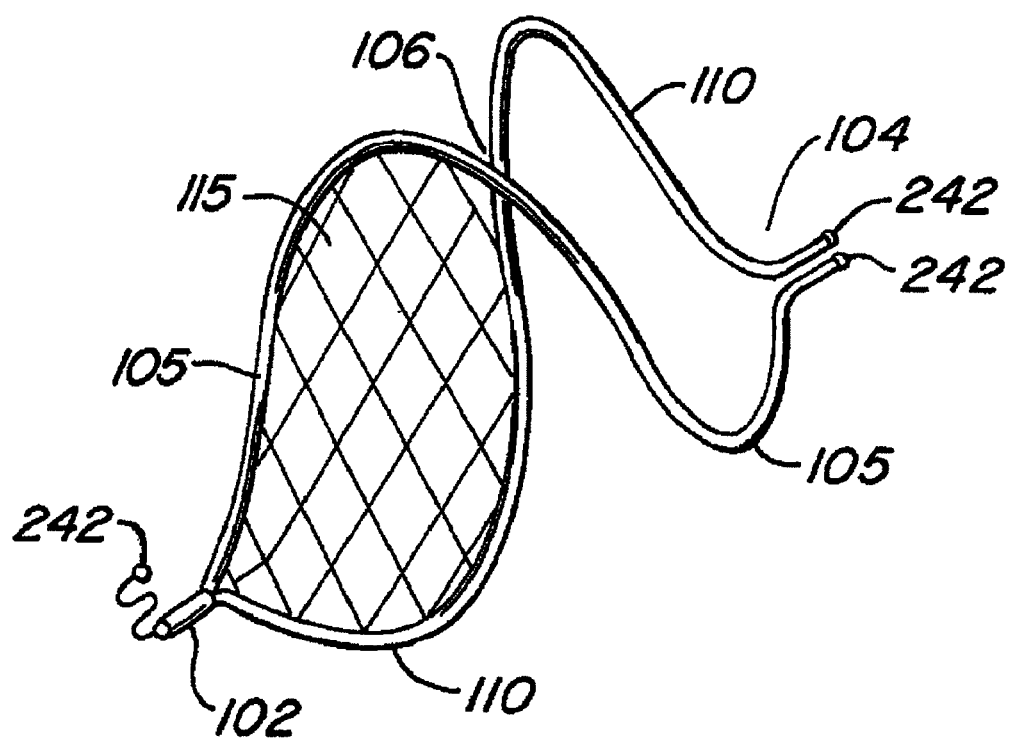

FIG. 87 is a perspective view of a prototype filter according to an embodiment of the present invention similar to the embodiment described in FIGS. 83A-83E above. In this embodiment the elongate structural members 105, 110 are joined at only one end (i.e., end 102). The support structure elements on the unconnected end are finished with plasma balls 242 to prevent vessel perforation and facilitate deployment and retrieval.

Summary of Experimental Results

The inventors are currently evaluating the performance of filter device embodiments of the present invention. Device performance is currently being evaluated in ongoing in-vivo animal and in-vitro bench studies. In particular, several device performance attributes have been evaluated, such as: device loading and advancement within a delivery sheath, deployment accuracy, thrombus capturing ability, fluoroscopic visibility, positional stability, device durability, and retrieval at three weeks following implantation. For the animal work completed to date, an ovine animal model has been used, as it is an accepted model used to study vascular implants, with anatomy and healing response similar to the adult human inferior vena cava (see, e.g., Brountzos E, et. al. "A new optional vena cava filter: retrieval at 12 weeks in an animal model", J Vasc Intery Radiol. 2003 June; 14(6):763-72; Crochet D, et. al., "Evaluation of the LGM Vena-Tech infrarenal vena cava filter in an ovine venous thromboembolism model", J Vasc Intery Radiol. 2001 June; 12(6):739-45; and Smouse B., "Second-generation optional vena cava filter" Endovascular Today. 2005 January, 4(1): 64-66, each of which is incorporated herein by reference in its entirety).

To date, thrombus trapping ability of the device has been evaluated using an in-vitro model. This model is constructed using segments of silicone "mock" vena cava connected to a flow circuit, in which fluid is pumped at approximately 3 L/min and maintained at 20 mm/Hg. Results have confirmed device stability and the "wedging" effect illustrated in FIG. 16A and FIG. 16B, when subjected to an embolic load that substantially covers the filter surface.

Initial animal study feasibility experiments have successfully demonstrated:
(a) loading and advancement of devices FIG. 68A in a compliant 6 Fr delivery sheath;
(b) compliance and positional stability of the device loaded in the sheath as shown in FIG. 69B;
(c) device visibility using both intravascular ultrasound (IVUS) and fluoroscopy;
(d) deployment accuracy;
(e) acute and sub-chronic positional stability;
(f) axial distensibility of the device (FIG. 2A-C);
(g) ability to acutely capture and reposition device (FIGS. 74A-D) using commercially available snares (FIGS. 71A-B);
(h) device durability; and
(i) the ability to easily recapture and remove a device after a three week dwell time using a 6 Fr sheath. The recapture was performed in less than 3 minutes (FIGS. 72A-F). Recaptured devices have indicated freedom from significant tissue incorporation or thrombus formation as well as in-vivo device durability.

At present, ongoing animal studies will be used to evaluate device performance and retrievability after one and two month implant durations (i.e., vessel dwell times).

It is understood that this disclosure, in many respects, is only illustrate of the numerous alternative filtering device embodiments of the present invention. Changes may be made in the details, particularly in matters of shape, size, material and arrangement of various filtering device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention.

What is claimed is:

1. A filter, comprising:
a first spiral support member;
a second spiral support member positioned adjacent the first spiral support member and joined to the first spiral support member to form a first end and a second end of the filter and at least one loop between the first end and the second end of the filter;
a first material covering a portion of the first and the second spiral support members;
a second material between the first material and the first and second spiral support members, wherein the first material is wrapped around the first and second spiral support members and the second material;
and a structure attached to the loop.

2. The filter of claim 1 wherein the structure is attached to the first material.

3. The filter of claim 1 wherein the second material is one of ePTFe, PTFE, PET, PFA, or FEP.

4. The filter of claim 1 wherein the second material covers the portion of the first and the second spiral support members covered by the first material.

5. The filter of claim 1 wherein the first material and the second material are part of a multi-lumen structure.

6. The filter of claim 1 wherein the structure is attached to the loop by the first material.

7. The filter of claim 5 wherein the structure is attached to one lumen of the multi-lumen structure.

8. The filter of claim 1 wherein the first material is a multi-lumen structure.

9. The filter of claim 8 wherein the multi-lumen structure is configured to release a pharmacological agent.

10. The filter of claim 8 wherein a lumen of the multi-lumen structure is at least partially filled with a pharmacological agent.

* * * * *